US011020476B2

(12) United States Patent
Boden et al.

(10) Patent No.: US 11,020,476 B2
(45) Date of Patent: Jun. 1, 2021

(54) METHODS AND COMPOSITIONS FOR INDUCING AN IMMUNE RESPONSE AGAINST HEPATITIS B VIRUS (HBV)

(71) Applicants: Janssen Sciences Ireland Unlimited Company, County Cork (IE); Bavarian Nordic A/S, Kvistgaard (DK)

(72) Inventors: Daniel Boden, San Mateo, CA (US); Helen Horton, Mol (BE); Jean-Marc Edmond Fernand Marie Neefs, Lier (BE); Soumitra Roy, Townsend, DE (US); Jerôme Hubertina Henricus Victor Custers, Alphen aan den Rijn (NL); Roland Christian Zahn, Rijnsburg (NL); Markus Kalla, Penzberg (DE)

(73) Assignees: JANSSEN SCIENCES IRELAND UNLIMITED COMPANY; BAVARIAN NORDIC A/S

( * ) Notice: Subject to any disclaimer, the term of this patent is extended or adjusted under 35 U.S.C. 154(b) by 0 days.

(21) Appl. No.: 16/223,400

(22) Filed: Dec. 18, 2018

(65) Prior Publication Data

US 2019/0184011 A1 Jun. 20, 2019

Related U.S. Application Data

(60) Provisional application No. 62/607,439, filed on Dec. 19, 2017.

(51) Int. Cl.
*A61K 39/29* (2006.01)
*C12N 15/86* (2006.01)
*A61K 39/12* (2006.01)
*A61K 39/00* (2006.01)

(52) U.S. Cl.
CPC ............ *A61K 39/292* (2013.01); *A61K 39/12* (2013.01); *C12N 15/86* (2013.01); *A61K 2039/545* (2013.01); *A61K 2039/70* (2013.01); *C12N 2710/10043* (2013.01); *C12N 2710/24143* (2013.01); *C12N 2730/10134* (2013.01)

(58) Field of Classification Search
None
See application file for complete search history.

(56) References Cited

U.S. PATENT DOCUMENTS

| 4,727,138 | A |   | 2/1988  | Goeddel                  |
|-----------|---|---|---------|--------------------------|
| 4,738,927 | A |   | 4/1988  | Taniguchi                |
| 4,762,791 | A |   | 8/1988  | Goeddel                  |
| 4,810,643 | A |   | 3/1989  | Souza                    |
| 4,892,743 | A |   | 1/1990  | Leibowitz                |
| 4,966,843 | A |   | 10/1990 | McCormick                |
| 4,999,291 | A |   | 3/1991  | Souza                    |
| 5,017,691 | A |   | 5/1991  | Lee                      |
| 5,116,742 | A |   | 5/1992  | Cech                     |
| 5,225,337 | A |   | 7/1993  | Robertson                |
| 5,246,921 | A |   | 9/1993  | Reddy                    |
| 5,780,036 | A | * | 7/1998  | Chisari ........... C07K 14/005 424/184.1 |
| 5,958,060 | A |   | 9/1999  | Premerlani               |
| 6,041,252 | A |   | 3/2000  | Walker                   |
| 6,110,161 | A |   | 8/2000  | Mathiesen                |
| 6,117,660 | A |   | 9/2000  | Walters                  |
| 6,224,879 | B1|   | 5/2001  | Sjoeberg                 |
| 6,261,281 | B1|   | 7/2001  | Mathiesen                |
| 6,273,525 | B1|   | 8/2001  | Erban                    |
| 6,278,895 | B1|   | 8/2001  | Bernard                  |
| 6,319,901 | B1|   | 11/2001 | Bernard                  |
| 6,697,669 | B2|   | 2/2004  | Dev                      |
| 6,873,549 | B2|   | 3/2005  | Khalid                   |
| 6,873,849 | B2|   | 3/2005  | De La Red                |
| 6,912,417 | B1|   | 6/2005  | Bernard                  |
| 6,939,862 | B2|   | 9/2005  | Bureau                   |
| 6,958,060 | B2|   | 10/2005 | Mathiesen                |
| 6,982,087 | B2|   | 1/2006  | Johnston                 |
| 7,328,064 | B2|   | 2/2008  | Mathiesen                |
| 7,419,674 | B2|   | 9/2008  | Chulay                   |
| 7,664,545 | B2|   | 2/2010  | Westersten               |
| 8,080,255 | B2|   | 12/2011 | Smith                    |
| 8,187,249 | B2|   | 5/2012  | Bernard                  |
| 8,209,006 | B2|   | 6/2012  | Smith                    |
| 8,216,589 | B2| * | 7/2012  | Yum .................... A61K 39/292 424/227.1 |
| 8,859,198 | B2| * | 10/2014 | Bartholomeusz ...... A61K 39/29 435/5 |
| 9,364,664 | B2|   | 6/2016  | Masterson                |
| 9,452,285 | B2|   | 9/2016  | Draghia-Akli             |
| 9,801,897 | B2|   | 10/2017 | Geall                    |
| 9,802,035 | B2|   | 10/2017 | Masterson                |
| 10,538,786| B2|   | 1/2020  | Kamrud                   |
| 2004/0213805 | A1 | | 10/2004 | Verheije                |
| 2005/0070700 | A1 | | 3/2005  | Giese                   |
| 2005/0277605 | A1 | | 12/2005 | Wu                      |
| 2009/0018031 | A1 | | 1/2009  | Trinklein               |
| 2009/0075384 | A1 | | 3/2009  | Kamrud                  |
| 2011/0110974 | A1 | | 5/2011  | Depla et al.            |
| 2012/0121650 | A1 | | 5/2012  | Johnston                |
| 2014/0079734 | A1 | | 3/2014  | Frolov                  |
| 2016/0166678 | A1 | | 6/2016  | Kallen                  |
| 2017/0314043 | A1 | | 11/2017 | Kamrud                  |
| 2018/0104359 | A1 | | 4/2018  | Kamrud                  |
| 2018/0171340 | A1 | | 6/2018  | Kamrud                  |

FOREIGN PATENT DOCUMENTS

KR 20080015211 A 2/2008
WO 8502862 7/1985

(Continued)

OTHER PUBLICATIONS

Boukhebza et al., "Comparative analysis of immunization schedules using a novel adenovirus-based immunotherapeutic targeting hepatitis B in naïve and tolerant mouse models" Vaccine, 32(26), pp. 3258-3263, 2014.

(Continued)

*Primary Examiner* — Agnieszka Boesen
(74) *Attorney, Agent, or Firm* — Ice Miller LLP

(57) ABSTRACT

Provided herein are Modified Vaccinia Ankara (MVA) vectors and adenovirus vectors encoding HBV antigens. Also provided are methods of enhancing an immune response in a human subject by utilizing the MVA and adenovirus vectors encoding HBV antigens in a prime/boost regimen to the enhance the immune response in the human subject.

20 Claims, 11 Drawing Sheets

Specification includes a Sequence Listing.

(56) References Cited

FOREIGN PATENT DOCUMENTS

| WO | 8504188 | | 9/1985 |
|---|---|---|---|
| WO | 9006370 | | 6/1990 |
| WO | 9503777 | A1 | 2/1995 |
| WO | 9531565 | | 11/1995 |
| WO | 9637616 | | 11/1996 |
| WO | 200224224 | A2 | 3/2002 |
| WO | 2002042480 | A2 | 5/2002 |
| WO | 2004055161 | A2 | 7/2004 |
| WO | 2005087311 | A1 | 9/2005 |
| WO | 2008/020656 | A1 | 2/2008 |
| WO | 2008093976 | A1 | 8/2008 |
| WO | 2011015656 | A2 | 2/2011 |
| WO | 2012/006376 | A2 | 1/2012 |
| WO | 2012087983 | A1 | 6/2012 |
| WO | 2012/109404 | A1 | 8/2012 |
| WO | 2012109668 | A1 | 8/2012 |
| WO | 2013007772 | A1 | 1/2013 |
| WO | 2014170493 | A2 | 10/2014 |
| WO | 2016020538 | A1 | 2/2016 |
| WO | 2016054003 | A1 | 4/2016 |
| WO | 2016184822 | A1 | 11/2016 |
| WO | 2017024000 | A1 | 2/2017 |
| WO | 2017/076988 | A1 | 5/2017 |
| WO | 2017172838 | A1 | 10/2017 |
| WO | 2017176319 | A1 | 10/2017 |
| WO | 2017180770 | A1 | 10/2017 |
| WO | 2018075235 | A1 | 4/2018 |
| WO | 2018106615 | A1 | 6/2018 |
| WO | 2018/189522 | A1 | 10/2018 |
| WO | 2018/225731 | A1 | 12/2018 |
| WO | 2019/099624 | A1 | 5/2019 |
| WO | 2019/123250 | A1 | 6/2019 |
| WO | 2019/126120 | A1 | 6/2019 |

OTHER PUBLICATIONS

Reyes-Sandoval et al, "Prime_Boost Immunization with Adenoviral and Modified Vaccinia virus Ankara Vectors Enhances the Durability and Polyfunctionality of Protective Malaria CD8 T-Cell Responses", Infection and Immunity, vol. 78, No. 1, pp. 145-153, Jan. 2010.
Martin et al., "TG1050, an immunotherapeutic to treat chronic hepatitis B, induces robust T cells and exerts an antiviral effect in HBV-persistent mice", Gut, 64, pp. 1961-1971, 2015.
Bartenschlager et al., "Expression of the P-protein of the human hepatitis B virus in a vaccinia virus system and detection of the nucleocapsid-associated P-gene product by radiolabelling at newly introduced phosphorylation sites", Nucleic Acids Research, vol. 20, No. 2, pp. 195-202, 1992.
Ramirez et at., "Biology of Attenuated Modified Vaccinia Virus Ankara Recombinant Vector in Mice: Virus Fate and Activation of B- and T-Cell Immune Responses in Comparision with the Western Reserve Strain and advantages as a Vaccine", Journal of Virology, Vo. 74, No. 2, pp. 923-933, 2000.
Jones et al., "Hepatitis B virus reverse transcriptase: diverse functions as classical and emerging targets for antiviral intervention", Emerging Microbes and Infections, 2(9), e56, 9 pages, 2013.
Obeng-Adjei et al. "DNA vaccine cocktail expressing genotype A and C HBV surface and consensus core antigens generates robust cytotoxic and antibody responses and mice and Rhesus macaques" Cancer Gene Therapy, 20, 652-662 2013.
World Health Organization, Hepatitis B: Fact sheet No. 204 [Internet] Mar. 2015. Available from https://www.who.int/news-room/fact-sheets/detail/hepatitis-b.
Cohen et al. "Is chronic hepatitis B being undertreated in the United States?" J. Viral Hepat., 18(6), 377-83, 2011.
Belloni et al. "IFN-a inhibits HBV transcription and replication in cell culture and in humanized mice by targeting the epigenetic regulation of the nuclear cccDNA minichromosome" J. Clin. Invest., 122(2), 529-537, 2012.
Michel et al. "Therapeutic vaccines and immune-based therapies for the treatment of chronic hepatitis B: perspectives and challenges." J. Hepatol., 54(6), 1286-1296, 2011.
Int'l Search Report and Written Opinion dated Mar. 26, 2018 in Int'l Application No. PCT/IB2017058148.
Int'l Search Report and Written Opinion dated Mar. 27, 2019 in Int'l Application No. PCT/IB2018/060257.
Int'l Search Report and Written Opinion dated May 22, 2018 in Int'l Application No. PCT/IB2017/058142, 17 pages.
Int'l Search Report and Written Opinion dated Apr. 17, 2019 in Int'l Application No. PCT/IB2018/060259, 16 pages.
Int'l Search Report and Written Opinion dated Jun. 25, 2018 in Int'l Application No. PCT/US2017/067269, 17 pages.
Int'l Search Report and Written Opinion dated Feb. 14, 2019 in Int'l Application No. PCT/US2018/066157, 19 pages.
Agapov et al., Noncytopathic Sindbis Virus RNA Vectors for Heterologous Gene Expression, Proc. Natl. Acad. Sci., 1998, pp. 12989-12994, vol. 95.
Altmann et al., Cotransfection of ICAM-1 and HLA-DR Reconstitutes Human Antigen-Presenting Cell Function in Mouse L Cells, Nature, 1989, pp. 512-514, vol. 338.
Altschul SF et al., "Basic Local Alignment Search Tool"; J. Mol. Biol. 215:403-410 (1990).
Atkins, G, et al. Therapeutic and Prophylactic Applications of Alphavirus Vectors, Expert Reviews in Molecular Medicine, Cambridge University Press, vol. 10, No. 1, pp. 1-18 (2008).
Attwood, T. The Babel of Bioinformatics, Science (2000) vol. 290, No. 5491, pp. 471-473 (Year: 2000).
Barbieri et al., Purification and partial characterization of another form of the antiviral protein from the seeds of *Phytolacca americana* L. (pokeweed), Biochem. J., 1982, pp. 55-59, vol. 203.
Barrette-Ng et al., Structure of Arterivirus nsp-4, J. Biol. Chem., 2002, pp. 39960-39966, vol. 277, Issue 42.
Beerens & Snijder, An RNA Pseudoknot in the 3' End of the Arterivirus Genome Has a Critical Role in Regulating Viral RNA Synthesis, J. Virol., 2007, pp. 9426-9436, vol. 81, Issue 17.
Berglund, P. et al., Enhancing Immune Response Using Suicidal DNA Vaccines,, Nature Biotechnology, vol. 16, pp. 562-565 (1998).
Besnard et al., Selection against expression of the *Escherichia coli* gene gpt in hprt+ mouse teratocarcinoma and hybrid cells, Mol. Cell. Biol., 1987, pp. 4139-4141, vol. 7.
Brakenhoff et al., Molecular cloning and expression of hybridoma growth factor in *Escherichia coli*, J. Immunol., Dec. 15, 1987, pp. 4116-4121, vol. 139, Issue 12.
Bzik et al., Molecular cloning and sequence analysis of the Plasmodium falciparum dihydrofolate reductase-thymidylate synthase gene, Proc. Natl. Acad. Sci. USA, Dec. 1987, pp. 8360-8364, vol. 84.
Calderwood et al., Nucleotide sequence of the Shiga-like toxin genes of *Escherichia coli*, Proc. Natl. Acad. Sci. USA, Jul. 1987, pp. 4364-4368, vol. 84.
Carroll and Collier, Active Site of Pseudomonas aeruginosa Exotoxin A, J. Biol. Chem., 1987, pp. 8707-8711, vol. 262.
Castillo-Olivares et al., Generation of a Candidate Live Marker Vaccine for Equine Arteritis Virus by Deletion of the Major Virus Neutralization Domain, J. Virol., 2003, pp. 8470-8480, vol. 77, Issue 15.
Chen et al., The complete primary structure of abrin-a B chain. FEBS Letters, 1992, pp. 115-118, vol. 309.
Cheng, W. et al. Enhancement of Sindbis Virus Self-Replicating RNA Vaccine Potency by Linkage of *Mycobacterium tuberculosis* Heat Shock Protein 70 Gene to an Antigen Gene, Journal of Immunology, vol. 166, pp. 6218-6226 (2001).
Chin et al., Tissue-specific Expression of Hepatic Functions Genetic Aspects, Ann. N.Y. Acad. Sci., Oct. 1986, pp. 120-130, vol. 478.
Collins et al., Primary Amino Acid Sequence of α-Trichosanthin and Molecular Models for Abrin A-chain and α-Trichosanthin, J. Biol. Chem., 1990, pp. 8665-8669, vol. 265.
Coussens et al., Tyrosine kinase receptor with extensive homology to EGF receptor shares chromosomal location with neu oncogene, Science, 1985, pp. 1132-1139, vol. 230.

(56) References Cited

OTHER PUBLICATIONS

Davis, N. et al., In Vitro Synthesis of Infectious Venezuelan Equine Encephalitis Virus RNA from a cDNA Clone: Analysis of a Viable Deletion Mutant Virology, vol. 171, pp. 189-204 (1989).
De Vries et al., Genetic Manipulation of Equine Arteritis Virus Using Full-Length cDNA Clones: Separation of Overlapping Genes and Expression of a Foreign Epitope. Virology, 2000, pp. 84-97, vol. 270.
De Vries et al., Recombinant Equine Arteritis Virus Expression Vector, Virology, Jun. 5, 2001, pp. 259-276, vol. 284, Issue 2.
De Wilde et al., Cyclophilin Inhibitors Block Arterivirus Replication by Interfering with Viral RNA Synthesis, J. Virol., 2013, pp. 1454-1464, vol. 87, Issue 3.
Den Boon et al., Equine Arteritis Virus Subgenomic RNA Transcription: UV Inactivation and Translation Inhibition Studies, Virology, 1995, pp. 364-372, vol. 213.
Deng et al., Structural Basis for the Regulatory Function of a Complex Zinc-binding Domain in a Replicative Arterivirus Helicase Resembling a Nonsense-Mediated mRNA Decay Helicase, Nucl. Acids Res., 2013, pp. 3464-3477, vol. 42, Issue 5.
Ding et al., In Vivo Genome-Wide Profiling of RNA Secondary Structure Reveals Novel Regulatory Features, Nature, 2014, pp. 696-700 (and Methods), vol. 505.
Dowdy et al., Efficient Generation of Human iPSCs by a Synthetic Self-Replicative RNA, Cell Stem Cell, 2013, pp. 246-254, vol. 13.
Dubensky, T. et al. Sindbis Virus DNA-Based Expression Vectors: Utility for in Vitro and in Vivo Gene Transfer, Journal of Virology, vol. 70, No. 1, pp. 508-519 (1996).
Evensen et al., Direct Molecular Cloning and Expression of Two Distinct Abrin A-chains, J. Biol. Chem., Apr. 15, 1991, pp. 6848-6852, vol. 266, Issue 11.
Fainstein et al., Nucleotide sequence analysis of human abl and bcr-abl cDNAs, Oncogene, Dec. 1, 1989, pp. 1477-1481, vol. 4. Issue 12.
Faktor et al., The identification of hepatitis B virus X gene responsive elements reveals functional similarity of X and HTLV-I tax, Oncogene, Jun. 1, 1990, pp. 867-872, vol. 5, Issue 6.
Familletti et al., A convenient and rapid cytopathic effect inhibition assay for interferon, Methods in Enz., 1981, pp. 387-394, vol. 78.
Fang et al., Efficient-2 Frameshifting by Mammalian Ribosomes to Synthesize an Additional Arterivirus Protein, PNAS, 2012, pp. E2920-E2928.
Field et al., Isolation and Characterization of Acyclovir-Resistant Mutants of Herpes Simplex Virus, J. Genl. Virol., 1980, pp. 115-124, vol. 49.
Finter et al., The Use of Interferon-α in Virus Infections, Drugs, 1991, pp. 749-765, vol. 42.
Firth et al., Discovery of a Small Arterivirus Gene that Overlaps the GP5 Coding Sequence and is Important for Virus Production, J. Genl. Virol., 2011, pp. 1097-1106, vol. 92.
Frolov, I. et al. Cis-acting RNA elements at the 5' end of Sindbis virus genome RNA regulate minus- and plus-strand RNA synthesis, RNO, vol. 7, pp. 1638-1651 (2001).
Frolov, I et al., Translation of Sindbis Virus mRNA: analysis of sequences downstream of the initiating AUG codon that enhance translation. Journal of Virology, vol. 70, No. 2, pp. 1182-1190 (1996).
Frolov, I et al.Translation of Sindbis Virus mRNA: Effects of Sequences Downstream of the Initiating Codon, Journal of Virology, vol. 68, No. 12, pp. 8111-8117, (1994).
Gansbacher et al., Retroviral Vector-mediated γ-Interferon Gene Transfer into Tumor Cells Generates Potent and Long Lasting Antitumor Immunity, Cancer Res., Dec. 15, 1999, pp. 7820-7825, vol. 50.
Gansbacher et al., Interleukin 2 Gene Transfer into Tumor Cells Abrogates Tumorigenicity and Includes Protective Immunity, J. Ex. Med., The Rockefeller University Press, Oct. 1990, pp. 1217-1224, vol. 172.

Gibson et al., Enzymatic assembly of DNA molecules up to several hundred kilobases, Nature Methods, Apr. 12, 2009, pp. 343-345, vol. 6.
Maruggi Giulietta et al, "Engineered alphavirus replicon vaccines based on known attenuated viral mutants show limited effects on immunogenicity", Virology, (Oct. 5, 2013), vol. 447, No. 1, doi:10.1016/J.VIROL.2013.07.021, ISSN 0042-6822, pp. 254-264, XP028754361.
Glaser AL et al., An infectious cDNA clone of equine arteritis virus: a tool for future fundamental studies and vaccine development. Proceedings of the 8th International Conference on Equine Infectious Diseases, Dubai 1998; 1999, pp. 166-176.
Golumbek et al., Treatment of established renal cancer by tumor cells engineered to secrete interleukin-4, Science, Nov. 1, 1991, pp. 713-716, vol. 254.
Gorchakov, R. et al., Selection of Functional 5 cis-Acting Elements Promoting Efficient Sindbis Virus Genome Replication, Journal of Virology, vol. 78, No. 1, pp. 61-75 (2004).
Grabstein et al., Cloning of a T cell growth factor that interacts with the beta chain of the interleukin-2 receptor. Science, 1994, pp. 965-968, vol. 264.
Hardy, R. et al Requirements at the 3 End of the Sindbis Virus Genome for Efficient Synthesis of Minus-Strand RNA, Journal of Virology, pp. 4630-4639 (2005).
Hooper et al., Molecular Smallpox Vaccine Delivered by Alphavirus Replicons Elicits Protective Immunity in Mice and Non-Human Primates, Vaccine, 2009, pp. 494-511, vol. 28, Issue 2.
Horikawa et al., Molecular cloning and nucleotide sequence of cDNA encoding the human liver S-adenosylmethionine synthetase, Biochem. Intl., Sep. 1, 1991, pp. 81-90, vol. 25, Issue 1.
Hyde, J. et al., The 5' and 3' ends of alphavirus RNAs—non-coding is not non-functional, Virus Res., vol. 206, pp. 99-107 (2015).
Irvin JD, Purification and partial characterization of the antiviral protein from Phytolacca americana which inhibits eukaryotic protein synthesis, Arch. Biochem & Biophys, Aug. 1975, pp. 522-528, vol. 169, Issue 2.
Irvin JD, Pokeweed antiviral protein, Pharmac. Ther., 1983, pp. 371-387, vol. 21, Issue 3.
Irvin JD et al., Purification and properties of a second antiviral protein from Phytolacca americana which inactivates eukaryotic ribosomes, Arch. Biochem. & Biophys., Apr. 1, 1980, pp. 418-425, vol. 200, Issue 2.
Jackson et al., Nucleotide sequence analysis of the structural genes for Shiga-like toxin I encoded by bacteriophage 933J from *Escherichia coli*. Microb. Path., Feb. 1987, pp. 147-153, vol. 2, Issue 2.
Jayaraman et al., Enhancement of in vivo cell-mediated immune responses by three distinct cytokines, J. Immunol., 1990, pp. 942-951, vol. 144.
Kamrud et al., Alphavirus Replicon Approach to Promoterless Analysis of IRES Elements, Virology, 2007, pp. 376-387, vol. 360.
Karlin & Altschul, Applications and statistics for multiple high-scoring segments in molecular sequences Proc. Nat’l. Acad. Sci. USA 90:5873-87 (1993).
Karupiah et al., Elevated natural killer cell responses in mice infected with recombinant vaccinia virus encoding murine IL-2, J. Immunol., Jan. 1, 1990, pp. 290-298, vol. 144, Issue 1.
Kelly, B. et al. Potential of Alphavirus Vectors in the Treatment of Advanced Solid Tumors, Recent Patents on Anti-Drug Discovery, vol. 2, No. 2, pp. 159-166 (2007).
Kerr et al., Anti-penicillin-V-amidase conjugates kill antigen-positive tumor cells when combined with doxorubicin phenoxyacetamide, Cancer. Immunol. Immunother.,1990, pp. 202-206, vol. 31, Issue 4.
Kim et al. 2014. Enhancement of protein expression by alphavirus replicons by designing self-replicating subgenomic RNAs. Proceedings National Academy of Sciences, 111 (29):10708-10713.
Klimstra et al., Adaptation of Sindbis Virus to BHK Cells Selects for Use of Heparan Sulfate as an Attachment Receptor. J. Virol. 72: pp. 7357 (1988), 10 pages.
Kinney, R. et al., Attenuation of Venezuelan Equine Encephalitis Virus Strain TC-83 Is Encoded by the 5'-Noncoding Region and the E2 Envelope Glycoprotein, Journal of Virology, vol. 67, No. 3, pp. 1269-1277, (1993).

(56) References Cited

OTHER PUBLICATIONS

Knoops et al., Ultrastructural Characterization of Arterivirus Replication Structures: Reshaping the Endoplasmic Reticulum to Accommodate Viral RNA Synthesis, J. Virol., 2011, pp. 2474-2487, vol. 86, Issue 5.

Kofler R. et al., Mimicking live flavivirus immunization with a noninfectious RNA vaccine, PNAS, vol. 101, No. 7, pp. 1951-1956, (2004).

Kulasegaran-Shylini et al., Structural and Functional Elements of Promoter Encoded by the 5' Untranslated Region of the Venezuelan Equine Encephalitis Virus Genome J. Virol. 83:17 p. 8327-8339 (2009).

Kulasegaran-Shylini et al., The 5'UTR-specific mutation in VEEV TC-83 genome has a strong effect on RNA replication and subgenomic RNA synthesis, but not on translation of the encoded proteins. Virology, 387(1): 211-221 (2009).

Lamb et al., Nucleotide sequence of cloned cDNA coding for preproricin, Eur. J. Biochem.,1985, pp. 265-270, vol. 148.

Lee et al., Multiagent Vaccines Vectored by Venezuelan Equine Encephalitis Virus Replicon Elicits Immune Responses to Marburg Virus and Protection against Anthrax and Botulinum Neurotoxin in Mice, Vaccine, 2006, pp. 6886-6892, vol. 24.

Lehmann et al., Arterivirus nsp12 Versus the Coronavirus nsp16 2'-O-Methyltransferase: Comparison of the C-terminal Cleavage Products of Two Nidovirus pp1ab Polyproteins, J. Genl. Virol., 2015, pp. 2643-2655, vol. 96.

Lehmann et al., Arterivirus RNA-Dependent RNA Polymerase: Vital Enzymatic Activity remains Elusive, Virology, 2016, pp. 68-74, vol. 487.

Linsley et al., Binding of the B Cell activation antigen B7 to CD28 costimulates T cell proliferation and Interleukin 2 mRNA accumulation, J. Exp. Med., Mar. 1991, pp. 721-730, vol. 173.

Linsley et al., CTLA-4 Is a second receptor for the B Cell activation antigen B7, J. Exp. Med., Sep. 1991, pp. 561-570, vol. 174.

Luo, R., et al., Antiviral activity of type I and type III interferons against porcine reproductive and respiratory syndrome virus (PRRSV), Antiviral Research, vol. 91, pp. 99-101 (2011).

Maher and Dolinick, Specific hybridization arrest of dihydrofolate reductase mRNA in vitro using anti-sense RNA or anti-sense oligonucleotides, Arch. Biochem & Biophys., Feb. 15, 1987, pp. 214-220, vol. 253, Issue 1.

Maio, et al., Modulation by cytokines of HLA antigens, intercellular adhesion molecule 1 and high molecular weight melanoma associated antigen expression and of immune lysis of clones derived from the melanoma cell line MeM 50-10. Can. Immunol. Immunother., Jan. 1989, pp. 34-42, vol. 30, Issue 1.

Manolaridis, et al., Structure and Genetic Analysis of the Arterivirus Nonstructural Protein 7α, J. Virol., 2011, pp. 7449-7453, vol. 85, Issue 14.

McKnight et al., Deduced consensus sequence of Sindbis virus strain AR339: mutations contained in laboratory strains which affect cell culture and in vivo phenotypes. Virol. 70:1981 (1996), 9 pages.

McLoughlin, M. et al. Alphavirus infections in salmonids—a review, Journal of Fish Diseases, vol. 30, pp. 511-531 (2007).

Mekalanos et al., Cholera toxin genes: nucleotide sequence, deletion analysis and vaccine development, Nature, 1983, pp. 551-557, vol. 306.

Mogler, M. et al., RNA-based viral vectors, Expert Rev. Vaccines, pp. 1-30 (2014).

Molenkamp R et al, "The arterivirus replicase is the only viral protein required for genome replication and subgenomic mRNA transcription.", The Journal of General Virology Oct. 2000, (Oct. 2000), vol. 81, No. Pt 10, ISSN 0022-1317, pp. 2491-2496, XP002771366.

Molenkamp et al., Isolation and Characterization of an Arterivirus Defective Interfering RNA Genome, J. Virol., 2000, pp. 3156-3165, vol. 74, Issue 7.

Molenkamp et al., Characterization of an Arterivirus Defective Interfering RNA, 2001, pp. 519-525. In the Nidoviruses (Coronaviruses and Arteriviruses), Ehud Lavi et al. (ed.), Kluwer Academic/Plenum Publishers.

Mullen, Transfer of the bacterial gene for cytosine deaminase to mammalian cells confers lethal sensitivity to 5-fluorocytosine: A negative selection system, Proc. Natl. Acad. Sci. USA, Jan. 1992, pp. 33-37, vol. 89.

Muraggi, G et al. Engineered Alphavirus Replicon Vaccines Based on Known Attenuated Viral Mutants Show Limited Effects on Immunogenicity, Virology, vol. 44, pp. 254-264 (2013).

Nagata, et al., Synthesis in E. coli of a polypeptide with human leukocyte interferon activity, Nature, 1980, pp. 316-320, vol. 284.

Nedialkova, et al., Biochemical Characterization of Arterivirus Nonstructural Protein 11 Reveals the Nidovirus-Wide Conservation of a Replicative Endoribonuclease, J. Virol., 2009, pp. 5671-5682, vol. 83, Issue 11.

Nedialkova et al., Arterivirus Nsp1 Modulates the Accumulation of Minus-Strand Templates to Control the Relative Abundance of Viral mRNAs, PLoS Pathogens, 2010, e1000772, pp. 1-15, vol. 6, Issue 2.

Needleman, S. et al., A general method applicable to the search for similarities in the amino acid sequence of two proteins J. Mol. Biol. 48:443-53 (1970).

Nolz, J et al. Strategies and Implications for Prime-Boost Vaccination to Generate Memory CD8 T Cells, Advances in Experimental Medicine and Biology, pp. 69-83, (2011).

Pasternak, Genetic Manipulation of Arterivirus Alternative mRNA Leader-Body Junction Sites Reveals Tight Regulation of Structural Protein Expression, J. Virol., Dec. 2000, pp. 11642-11653, vol. 74, Issue 24.

Pasternak, Sequence requirements for RNA strand transfer during nidovirus discontinuous subgenomic RNA synthesis, EMBO J., 2001, pp. 7220-7228, vol. 20, Issue 24.

Pasternak, The stability of the duplex between sense and antisense transcription-regulating sequences is a crucial factor in arterivirus subgenomic mRNA synthesis, J. Virol., 2003, pp. 1175-1183, vol. 77, Issue 2.

Pasternak, Regulation of Relative Abundance of Arterivirus Subgenomic mRNAs, J. Virol., Aug. 2004, pp. 8102-8113, vol. 78, Issue 15.

Pearson, W. et al., Improved tools for biological sequence comparison, Proc. Natl. Acad. Sci. US, vol. 85, pp. 2444-2448 (1988).

Pedersen et al., Open Reading Frame 1a-Encoded Subunits of the Arterivirus Replicase induce Endoplasmic Reticulum-Derived Double-Membrane Vesicles which carry the Viral Replication Complex, J. Virol., 1999, pp. 2016-2026, vol. 73, Issue 3.

Perri et al., Replicon Vectors Derived from Sindbis Virus and Semliki Forest Virus that Establish Persistent Replication in Host Cells, J. Virol., 2000, pp. 9802-9807, vol. 74, Issue 20.

Pijlman, G. et al., Kunjin virus replicons: an RNA-based, noncytopathic viral vector system for protein production, vaccine and gene therapy applications, Expert Opin. Biol. Ther, vol. 6, No. 2, pp. 135-145 (2006).

Posthuma et al., Site-Directed Mutagenesis of the Nidovirus Replicative Endoribonuclease NendoU Exerts Pleiotropic Effects on the Arterivirus Life Cycle, J. Virol., 2006, pp. 1653-1661, vol. 80, Issue 4.

Posthuma et al., Formation of the Arterivirus Replication/Transcription Complex: a Key Role for Nonstructural Protein 3 in the Remodeling of Intracellular Membranes, J. Virol., 2008, pp. 4480-4491, vol. 82, Issue 9.

Pushko et al., Individual and Bivalent Vaccines Based on Alphavirus Replicons Protect Guinea Pigs against Infection with Lassa and Ebola Viruses, J. Virol., 2001, pp. 11677-11685, vol. 75, Issue 23.

Pushko et al., Replicon-Helper Systems from Attenuated Venezuelan Equine Encephalitis Virus: Expression of Heterologous Genes in Vitro and Immunization against Heterologous Pathogens in Vivo, Virology, Dec. 22, 1997, pp. 389-401, vol. 239, Issue 2.

Radford et al., Cell-Type Specificity of Interferon-γ-Mediated HLA Class I Gene Transcription in Human Hematopoietic Tumor Cells. American Society of Hepatology, 1991, pp. 2008-2015.

(56) References Cited

OTHER PUBLICATIONS

Rice, C. et al., Production of Infectious RNA Transcripts from Sindbis Virus cDNA Clones: Mapping of Lethal Mutations, Rescue of a Temperature-Sensitive Marker, and in Vitro Mutagenesis to Generate Defined Mutants, Journal of Virology, vol. 61, No. 12, pp. 3809-3819 (1987).

Rogne et al., The isolation and characterisation of a cDNA clone for human lecithin:cholesterol acyl transferase and its use to analyze the genes in patients with LCAT deficiency and fish eye disease, Biochem, Biophys. Res. Commun., 1987, pp. 161-169, vol. 148, Issue 1.

Sanchez and Holmgren, Recombinant system for overexpression of cholera toxin B subunit in Vibrio cholerae as a basis for vaccine development, Proc. Natl. Acad. Sci. USA, Jan. 1989, pp. 481-485, vol. 86, Issue 2.

Seif et al., Stable Antiviral Expression in BALB/c 3T3 Cells Carrying a Beta Interferon Sequence behind a Major Histocompatibility Complex Promoter Fragment, J. Virol., Oct. 1991, pp. 664-671, vol. 65, Issue 2.

Seybert et al., Biochemical Characterization of the Equine Arteritis Virus Helicase Suggests a Close Functional Relationship Between Arterivirus and Coronavirus Helicases, J. Virol., 2000, pp. 9586-9593, vol. 74, Issue 20.

Shylini, R Structure-Function Studies of the Venezuelanequine Encephalitis Virus 5'utr Promoter Element and Its Role in Attenuation of the Virus, Dissertation for Doctor of Philosophy, The University of Texas Medical Branch (2009) 147 pages.

Sjoberg,E et al., A Significantly Improved Semliki Forest Virus Expression System Based on Translation Enhancer Segments from the Viral Capsid Gene, Biotechnology, Vo,. 12, pp. 1127-1131, (1994).

Smith et al., Comparison of Biosequences, Adv. Appl. Math., 2:482-89 (1981).

Snijder, E.J., The Arterivirus Replicase, The Road from RNA to Protein(s), and Back Again, 1998, pp. 97-108. In Coronaviruses and Arteriviruses, Enjuanes et al. (ed.), Plenum Press, NY.

Snijder, E.J., Arterivirus RNA Synthesis Dissected, 2001, pp. 241-253. In the Nidoviruses (Coronaviruses and Arteriviruses), Ehud Lavi et al. (ed.), Kluwer Academic/Plenum Publishers.

Snijder et al., Proteolytic Processing of the Arterivirus Replicase, 1995, pp. 443-451. In Corona- and Related Viruses, P.J. Talbot and G.A. Levy (ed.), Plenum Press, NY.

Snijder et al., The Arterivirus Nsp2 Protease, J. Biol. Chem., 1995, pp. 16671-16676, vol. 270, Issue 28.

Snijder et al., Heterodimerization of the Two Major Envelope Proteins is Essential for Arterivirus Infectivity, J. Virol., 2003, pp. 97-104, vol. 77, Issue 1.

Snijder et al., 2005. The order Nidovirales, pp. 390-404, In Topley and Wilson's microbiology and microbial infections, B. W. Mahy and V. ter Meulen (ed.), Hodder Arnold, London, United Kingdom.

Snijder EJ et al., "Identification of a Novel Structural Protein of Arteriviruses," J. Virol, Aug. 1999, pp. 6335-6345, vol. 37, Issue 8.

Stanton et al., Nucleotide sequence comparison of normal and translocated murine c-myc genes, Nature, Aug. 1984, pp. 423-425, vol. 310.

Strauss etal., The AlpahViruses: Gene Expression, Replication and Evolution, Microbiological Reviews, pp. 491-562, Sep. 1994.

Stirpe et al., Gelonin, a New Inhibitor of Protein Synthesis, Nontoxic to Intact Cells, J. Biol. Chem., Jul. 25, 1980, pp. 6947-6953, vol. 255.

Te Velthuis, et al., Zn2+ Inhibits Coronavirus and Arterivirus RNA Polymerase Activity in Vitro and Zinc Ionophores Block the Replication of these Viruses in Cell Culture, PLoS Pathogens, 2010, e1001176, pp. 1-10, vol. 6, Issue 11.

Tepper et al., Murine interleukin-4 displays potent anti-tumor activity in vivo, Cell, May 5, 1989, pp. 503-512, vol. 57.

Thaa et al., Myristoylation of the Arterivirus E Protein: The Fatty Acid Modification is not Essential for Membrane Association but Contributes Significantly to Virus Infectivity, J. Genl. Virol., 2009, pp. 2704-2712, vol. 90.

Tijerina et al., DMS Footprinting of Structured RNAs and RNA-Protein Complexes, Nat. Protoc., 2007, pp. 2608-2623, vol. 2, Issue 10.

Tijms et al., A zinc finger-containing papain-like protease couples subgenomic mRNA synthesis to genome translation in a positive-stranded RNA virus, Proc. Natl. Acad. Sci. USA, 2001, pp. 1889-1894, vol. 98, Issue 4.

Tijms et al., Arterivirus Subgenomic mRNA Synthesis and Virion Biogenesis Depend on the Multifunctional nsp1 Autoprotease, J. Virol., Oct. 2007, pp. 10496-10505, vol. 81, Issue 19.

Toribio et al., Inhibition of host translation by virus infection in vivo, PNAS, vol. 107, No. 21, pp. 9837-9842 (2010).

Toribio et al., An RNA Trapping Mechanism in Alphavirus MRNA Promotes Translation and Initiation Nucleic Acids Res. 19, 44(9): pp. 4368-4380 (2016).

Tweten et al., Diphtheria toxin. Effect of substituting aspartic acid for glutamic acid 148 on ADP-ribosyltransferase activity., J. Biol. Chem., Jun. 3, 1985, pp. 10392-10394, vol. 260.

Twu et al., Hepatitis B virus X gene can transactivate heterologous viral sequences, Proc Natl. Acad. Sci. USA, Mar. 1989, pp. 2046-2050, vol. 86.

Van Aken et al., Expression, Purification, and in Vitro Activity of an Arterivirus Main Proteinase, Virus Res., 2006, pp. 97-106, vol. 120.

Van Aken et al., Mutagenesis Analysis of the nsp4 Main Proteinase Reveals Determinants of Arterivirus Replicase Polyprotein Autoprocessing, J. Virol., 2006, pp. 3428-3437, vol. 80, Issue 7.

Van Den Born et al., Discontinuous Subgenomic RNA Synthesis in Arteriviruses is Guided by an RNA Hairpin Structure Located in the Genomic Leader Region, J. Virol., 2005, pp. 6312-6324, vol. 79, Issue 10.

Van Den Born, Value of routine funduscopy in patients with hypertension: systematic review, BMJ, Jul. 9, 2005, pp. 1-5, vol. 331.

Van Den Born, et al., "An infectious recombinant equine arteritis virus expressing green fluorescent protein from its replicase gene," J. Genl. Virol., Apr. 2007, pp. 1196-1205, vol. 88.

Van Der Meer et al., ORF1a-Encoded Replicase Subunits are Involved in the Membrane Association of the Arterivirus Replication Complex, J. Virol., 1998, pp. 6689-6698, vol. 72, Issue 8.

Van Dinten, An infectious arterivirus cDNA clone: Identification of a replicase point mutation that abolishes discontinuous mRNA transcription, Proc. Natl. Acad. Sci. USA, Feb. 1997, pp. 991-996, vol. 94, Issue 3.

Van Dinten et al., Proteolytic Processing of the Open Reading Framer 1b-Encoded Part of Arterivirus Replicase is Mediated by nsp4 Serine Protease and is Essential for Virus Replication, J. Virol., 1999, pp. 2027-2037, vol. 73, Issue 3.

Van Dinten et al., The Predicted Metal-Binding Region of the Arterivirus Helicase Protein is Involved in Subgenomic mRNA Synthesis, Genome Replication, and Virion Biogenesis, J. Virol., 2000, pp. 5213-5223, vol. 74, Issue 11.

Van Hemert et al., The in Vitro RNA Synthesizing Activity of the Isolated Arterivirus Replication/Transcription Complex is Dependent on a Host Factor, J. Biol. Chem., 2008, pp. 16525-16536, vol. 283, Issue 24.

Van Kasteren et al., Arterivirus and Nairovirus Ovarian Tumor Domain-Containing Deubiquitinases Target Activated RIG-I to Control Innate Immune Signaling, J. Virol., 2011, pp. 773-785, vol. 82, Issue 2.

Van Kasteren et al., Deubiquitinase Function of Arterivirus Papain-Like Protease 2 Suppresses the Innate Immune Response in Infected Host Cells, PNAS, 2013, pp. E838-E847.

Van Marle, et al., Characterization of an Equine Arteritis Virus Replicase Mutant Defective in Subgenomic mRNA Synthesis, J. Virol., 1999, pp. 5274-5281, vol. 73, Issue 7.

Van Marle et al., Arterivirus discontinuous mRNA transcription is guided by base pairing between sense and antisense transcription-regulating sequences, Pro. Natl. Acad. Sci. USA, Aug. 6, 1999, pp. 12056-12061, vol. 96, Issue 21.

Ventoso, I., Adaptive Changes in Alphavirus mRNA Translation Allowed Colonization of Vertebrate Hosts, Journal of Virology, vol. 86, No. 17, pp. 9484-9494 (2012).

(56) References Cited

OTHER PUBLICATIONS

Ventoso, I. et al. Translational resistance of late alphavirus mRNA to eIF2 phosphorylation: a strategy to overcome the antiviral effect of protein kinase PKR, Genes and Development, vol. 20, pp. 87-100 (2006).
Vrudhula et al., Prodrugs of doxorubicin and melphalan and their activation by a monoclonal antibody-penicillin-G amidase conjugate, J. Med. Chem., 1993, pp. 919-923, vol. 36, Issue 7.
Ward, S. et al., Generation of CTL responses using Kunjin replicon RNA, Immunology and Cell Biology, vol. 81, pp. 73-78 (2003).
Warner et al. Induction of the HIV-Specific and Antibody Responses in Mice Using Retroviral Vector-Transduced Cells, AIDS Res. and Human Retroviruses, vol. 7, No. 8, pp. 645-655 (1991).
Wassenaar, et al., Alternative Proteolytic Processing of the Arterivirus Replicase ORF1a Polyprotein: Evidence that NSP2 Acts as a Cofactor for the NSP4 Serine Protease, J. Virol., 1997, pp. 9313-9322, vol. 71, Issue 12.
Watanabe, et al., Exogenous expression of mouse interferon gamma cDNA in mouse neuroblastoma C1300 cells results in reduced tumorigenicity by augmented anti-tumor immunity, Proc. Natl. Acad. Sci. USA, Dec. 1989, pp. 9456-9460, vol. 86.
Weber et al., Immunotherapy of a murine tumor with interleukin 2. J. Exp. Med., 1987, pp. 1716-1733, vol. 166.
White, L. et al., Role of Alpha/Beta Interferon in Venezuelan Equine Encephalitis Virus Pathogenesis: Effect of an Attenuating Mutation in the 59 Untranslated Region, Journal of Virology, vol. 75, No. 8, pp. 3706-3718 (2001).
Wilson et al., Prospects for gene therapy of familial hypercholesterolemia, Mol. Biol. Med., Jun. 1, 1990, pp. 223-232, vol. 7, Issue 3.
Wood et al., Preproabrin: genomic cloning, characterisation and the expression of the A-chain in *Escherichia coli*, Eur. J. Biochem., 1991, pp. 723-732, vol. 198.
Yamamoto et al., The human LDL receptor: a cysteine-rich protein with multiple Alu sequences in its mRNA, Cell, Nov. 1984, pp. 27-38, vol. 39, Issue 1.
Zhou, X. et al. Self-replicating Semliki Forest virus RNA as recombinant vaccine, Vaccine, vol. 12, No. 16, pp. 1510-1514 (1994).
GenBank/NCBI accession No. J02363, dated Oct. 25, 2000; accessed Jul. 16, 2018, 7 pages.
GenBank accession # JX473847, dated Dec. 22, 2012; accessed Apr. 17, 2019, 6 pages.
GenBank/NCBI accession No. L01443.1., dated Nov. 17, 2014; accessed Oct. 3, 2016, 7 pages.
GenBank/NCBI accession No. L04653, dated Jun. 1, 2001; accessed Jul. 16, 2018, 6 pages.
GenBank/NCBI accession No. NC_001449, dated Feb. 10, 2015; accessed Jul. 16, 2018, 7 pages.
GenBank/NCBI accession No. NC_003215, dated Feb. 10, 2015; accessed Jul. 16, 2018, 6 pages.
GenBank/NCBI accession No. U38304; dated Feb. 10, 2015; accessed Jul. 16, 2018, 5 pages.
GenBank/NCBI accession No. U38305, dated Jan. 30, 2016, accessed Jul. 16, 2018, 5 pages.
GenBank/NCBI accession No. X04129, dated Mar. 13, 2001; accessed Jul. 16, 2018, 5 pages.
International Search Report and Written Opinion, dated Dec. 1, 2017, in International Application No. PCT/US2017/054928, 18 pages.
International Search Report and Written Opinion, dated Jul. 10, 2017, in International Patent Application No. PCT/US2017/027249, filed Apr. 12, 2017, 16 pages.
International Search Report and Written Opinion, dated Jul. 3, 2018, in International Application No. PCT/US2017/064561, 22 pages.
Kim, et al., "New World and Old World Alphaviruses Have Evolved to Exploit Different Components of Stress Granules, FXR and G3BP Proteins, for Assembly of Viral Replication Complexes", PLOS Pathogens, vol. 12, No. 8, p. 1-31, (Aug. 2016).
Foy, et al., "Hypervariable domains of nsP3 proteins of New World and Old World alphaviruses mediate formation of distinct, virus-specific protein complexes", J. Virol., vol. 87, No. 4, p. 1997-2010, (Dec. 2012).
Gotte, et al., "The Enigmatic Alphavirus Non-Structural Protein 3 (nsP3) Revealing Its Secrets at Last", Viruses, vol. 10, No. 3, p. 105, 1/26 to 26/26, (Feb. 2018).
Meshram, et al., "Multiple Host Factors Interact with the Hypervariable Domain of Chikungunya Virus nsP3 and Determine Viral Replication in Cell-Specific Mode", J. Virol., vol. 92, No. 16, p. 1-24, (Aug. 2018).
International Search Report and Written Opinion dated Dec. 13, 2019 in International Appl. No. PCT/US2019/055125, 15 pages.
Frolov et al, (Journal of Virology, 1999, p. 3854-3865).
Bolz et al.: "Use of Recombinant Virus Replicon Particles for Vaccination against *Mycobacterium ulcerans* Disease"; PLoS Negl Trop Dis,, Aug. 14, 2015, vol. 9(8):e0004011., PDF File: p. 1-18.
International Search Report dated Apr. 23, 2019, regarding PCT/US2019/014210, 13 pages.
Lundstrom, Kenneth L: "Replicon RNA Viral Vectors as Vaccines"; Vaccines, 2016, vol. 4(4). pii: E39. PDF File: p. 1-23.
Uematsu et al.: "Lack of Interference with Immunogenicity of a Chimeric Alphavirus Replicon Particle-Based Influenza Vaccine by Preexisting Antivector Immunity"; Clin Vaccine Immunol., Jul. 2012, vol. 19(7), p. 991-998.
Xu et al.: "Type-specific and cross-reactive antibodies induced by human papillomavirus 31 L1/L2 virus-like particle";, J Med Microbiol. 2007, vol. 56(Pt 7), p. 907-13.
Tian et al. Arterivirus minor envelope proteins are a major determinant of viral tropism in cell culture. J Virol. Apr. 2012;86(7):3701-12. (Year: 2012).
Baker et al., Protein Structure Predication and Structural Genomics, Science (2001) vol. 294, No. 5540, pp. 93-96 (Year: 2001).
Huang et al. Development of a vaccine vector based on a subgenomic replicon of porcine reproductive and respiratory syndrome virus. J Virol Methods. Sep. 2009;160(1-2):22-8. (Year: 2009).
Obeng-Adjei et al., "Synthetic DNA immunogen encoding hepatitis B core antigen drives immune response in liver," Cancer Gene Therapy, 2012, 19:779-787.

\* cited by examiner

METHODS AND COMPOSITIONS FOR INDUCING AN IMMUNE RESPONSE AGAINST HEPATITIS B VIRUS (HBV)

CROSS-REFERENCE TO RELATED APPLICATIONS

This application claims priority to U.S. Provisional Patent Application No. 62/607,439, filed Dec. 19, 2017, the disclosure of which is incorporated herein by reference in its entirety.

REFERENCE TO SEQUENCE LISTING SUBMITTED ELECTRONICALLY

This application contains a sequence listing, which is submitted electronically via EFS-Web as an ASCII formatted sequence listing with a file name "688097-413 Sequence Listing" and a creation date of Dec. 14, 2018, and having a size of 49.6 KB. The sequence listing submitted via EFS-Web is part of the specification and is herein incorporated by reference in its entirety.

FIELD OF THE INVENTION

This invention relates to biotechnology. More particularly, the invention relates to methods and compositions for enhancing an immune response to Hepatitis B Virus (HBV) in a subject in need thereof.

BACKGROUND OF THE INVENTION

Hepatitis B virus (HBV) is a small 3.2-kb hepatotropic DNA virus that encodes four open reading frames and seven proteins. About two billion people are infected with HBV, and approximately 240 million people have chronic hepatitis B infection (chronic HBV), characterized by persistent virus and subvirus particles in the blood for more than 6 months (1). Persistent HBV infection leads to T-cell exhaustion in circulating and intrahepatic HBV-specific CD4+ and CD8+ T-cells through chronic stimulation of HBV-specific T-cell receptors with viral peptides and circulating antigens. As a result, T-cell polyfunctionality is decreased (i.e., decreased levels of IL-2, tumor necrosis factor (TNF)-α, IFN-γ, and lack of proliferation).

A safe and effective prophylactic vaccine against HBV infection has been available since the 1980s and is the mainstay of hepatitis B prevention (3). The World Health Organization recommends vaccination of all infants, and, in countries where there is low or intermediate hepatitis B endemicity, vaccination of all children and adolescents (<18 years of age), and of people of certain at risk population categories. Due to vaccination, worldwide infection rates have dropped dramatically. However, prophylactic vaccines do not cure established HBV infection.

Chronic HBV is currently treated with IFN-α and nucleoside or nucleotide analogs, but there is no ultimate cure due to the persistence in infected hepatocytes of an intracellular viral replication intermediate called covalently closed circular DNA (cccDNA), which plays a fundamental role as a template for viral RNAs, and thus new virions. It is thought that induced virus-specific T-cell and B-cell responses can effectively eliminate cccDNA-carrying hepatocytes. Current therapies targeting the HBV polymerase suppress viremia, but offer limited effect on cccDNA that resides in the nucleus and related production of circulating antigen. The most rigorous form of a cure may be elimination of HBV cccDNA from the organism, which has neither been observed as a naturally occurring outcome nor as a result of any therapeutic intervention. However, loss of HBV surface antigens (HBsAg) is a clinically credible equivalent of a cure, since disease relapse can occur only in cases of severe immunosuppression, which can then be prevented by prophylactic treatment. Thus, at least from a clinical standpoint, loss of HBsAg is associated with the most stringent form of immune reconstitution against HBV.

For example, immune modulation with pegylated interferon (pegIFN)-α has proven better in comparison to nucleoside or nucleotide therapy in terms of sustained off-treatment response with a finite treatment course. Besides a direct antiviral effect, IFN-α is reported to exert epigenetic suppression of cccDNA in cell culture and humanized mice, which leads to reduction of virion productivity and transcripts (4). However, this therapy is still fraught with side-effects and overall responses are rather low, in part because IFN-α has only poor modulatory influences on HBV-specific T-cells. In particular, cure rates are low (<10%) and toxicity is high. Likewise, direct acting HBV antivirals, namely the HBV polymerase inhibitors entecavir and tenofovir, are effective as monotherapy in inducing viral suppression with a high genetic barrier to emergence of drug resistant mutants and consecutive prevention of liver disease progression. However, cure of chronic hepatitis B, defined by HBsAg loss or seroconversion, is rarely achieved with such HBV polymerase inhibitors. Therefore, these antivirals in theory need to be administered indefinitely to prevent reoccurrence of liver disease, similar to antiretroviral therapy for human immunodeficiency virus (HIV).

Therapeutic vaccination has the potential to eliminate HBV from chronically infected patients (5). Many strategies have been explored, but to date therapeutic vaccination has not proven successful.

BRIEF SUMMARY OF THE INVENTION

Accordingly, there is an unmet medical need in the treatment of hepatitis B virus (HBV), particularly chronic HBV, for a finite well-tolerated treatment with a higher cure rate. The application satisfies this need. Provided are Modified Vaccinia Ankara (MVA) vectors. An MVA vector of the application comprises a non-naturally occurring nucleic acid molecule comprising a first polynucleotide sequence encoding an HBV polymerase antigen comprising an amino acid sequence that is at least 98% identical to SEQ ID NO: 4. The HBV polymerase antigen of the MVA vectors can, for example, be capable of inducing an immune response in a mammal against at least two HBV genotypes. Preferably, the HBV polymerase antigen is capable of inducing a T cell response in a mammal against at least HBV genotypes B, C, and D. More preferably the HBV polymerase antigen is capable of inducing a CD8 T cell response in a human subject against at least HBV genotypes A, B, C, and D. In an embodiment of the application, an HBV polymerase antigen comprises the amino acid sequence of SEQ ID NO: 4. In an embodiment of the application, the first polynucleotide sequence is at least 90% identical to SEQ ID NO: 3. In an embodiment of the application, the first polynucleotide sequence comprises the polynucleotide sequence of SEQ ID NO: 3.

In an embodiment of the application, an MVA vector can further comprise a polynucleotide sequence encoding a signal sequence operably linked to the HBV polymerase antigen. The signal sequence can, for example, comprise an amino acid sequence of SEQ ID NO: 6 or SEQ ID NO: 11.

Preferably, the signal sequence is encoded by the polynucleotide sequence of SEQ ID NO: 5 or SEQ ID NO: 10.

In an embodiment of the application, an MVA vector further comprises a second polynucleotide sequence encoding a truncated HBV core antigen consisting of the amino acid sequence of SEQ ID NO: 2. In an embodiment of the application, the second polynucleotide sequence is at least 90% identical to SEQ ID NO: 1. In an embodiment of the application, the second polynucleotide sequence comprises the polynucleotide sequence of SEQ ID NO: 1.

Also provided are compositions comprising an MVA vector of the application and a pharmaceutically acceptable carrier.

Also provided are methods of enhancing an immune response in a human subject in need thereof. The methods comprise (a) administering to the human subject a first composition comprising an immunologically effective amount of an adenovirus vector comprising a non-naturally occurring nucleic acid molecule comprising a first polynucleotide sequence encoding an HBV polymerase antigen comprising an amino acid sequence that is at least 98% identical to SEQ ID NO:4; and (b) administering to the human subject a second composition comprising an immunologically effective amount of an MVA vector of the application; to thereby obtain an enhanced immune response against the HBV antigen in the human subject. In an embodiment of the application, the HBV polymerase antigen does not have reverse transcriptase activity and RNase H activity. In an embodiment of the application, the first composition is for priming the immune response, and the second composition is for boosting the immune response in the subject in need thereof. In an embodiment of the application, step (b) is conducted 1-12 weeks after step (a). In an embodiment of the application, step (b) is conducted 2-12 weeks after step (a). In an embodiment of the application, step (b) is conducted at least 1 week after step (a). In an embodiment of the application, step (b) is conducted at least 2 weeks after step (a).

In an embodiment of the application, an HBV polymerase antigen of the first composition is capable of inducing an immune response in the human subject against at least two HBV genotypes, preferably the HBV polymerase antigen is capable of inducing a T cell response in the human subject against at least HBV genotypes B, C, and D, and more preferably the HBV polymerase antigen is capable of inducing a CD8 T cell response in the human subject against at least HBV genotypes A, B, C, and D.

In an embodiment of the application, the HBV polymerase antigen of the first composition comprises the amino acid sequence of SEQ ID NO: 4. The first polynucleotide sequence of the first composition can, for example, be at least 90% identical to SEQ ID NO: 19. In an embodiment of the application, the first polynucleotide sequence of the first composition comprises the polynucleotide sequence of SEQ ID NO: 19.

In an embodiment of the application, the nucleic acid molecule of the adenovirus vector in the first composition further comprises a second polynucleotide sequence encoding a truncated HBV core antigen consisting of the amino acid sequence of SEQ ID NO: 2. The second polynucleotide sequence of the first composition can, for example, be at least 90% identical to SEQ ID NO: 17. In an embodiment of the application, the second polynucleotide sequence of the first composition comprises the polynucleotide sequence of SEQ ID NO: 17.

In an embodiment of the application, the first and second polynucleotide sequences of the first composition encode a fusion protein comprising the truncated HBV core antigen operably linked to the HBV polymerase antigen. The fusion protein of the first composition can, for example, comprise the truncated HBV core antigen operably linked to the HBV polymerase antigen via a linker. The linker of the first composition can, for example, comprise the amino acid sequence of $(AlaGly)_n$, wherein n is an integer of 2 to 5. Preferably the linker is encoded by a polynucleotide sequence comprising SEQ ID NO:14. In an embodiment of the application, the fusion protein of the first composition comprises the amino acid sequence of SEQ ID NO: 12.

In an embodiment of the application, the enhanced immune response comprises an enhanced antibody response against the HBV antigen in the human subject. The enhanced immune response can, for example, comprise an enhanced CD8+ T cell response against the HBV antigen in the human subject. The enhanced immune response can, for example, comprise an enhanced CD4+ T cell response against the HBV antigen in the human subject.

In an embodiment of the application, the adenovirus vector is an rAd26 or rAd35 vector.

In an embodiment of the application, a method of enhancing an immune response in a human subject comprises (a) administering to the human subject a first composition comprising an immunologically effective amount of a first plasmid comprising a first non-naturally occurring nucleic acid molecule comprising a first polynucleotide sequence encoding an HBV polymerase antigen comprising an amino acid sequence that is at least 98% identical to SEQ ID NO: 4 and a second plasmid comprising a second non-naturally occurring nucleic acid molecule comprising a second polynucleotide sequence encoding a truncated HBV core antigen consisting of the amino acid sequence of SEQ ID NO: 2; and (b) administering to the human subject a second composition comprising an immunologically effective amount of the MVA vector of the application; to thereby obtain an enhanced immune response against the HBV antigen in the human subject. In an embodiment of the application, the HBV polymerase antigen of the first composition does not have reverse transcriptase activity and RNase H activity. In an embodiment of the application, the first composition is for priming the immune response and the second composition is for boosting the immune response. In an embodiment of the application, step (b) is conducted 1-12 weeks after step (a). In an embodiment of the application, step (b) is conducted 2-12 weeks after step (a). In an embodiment of the application, step (b) is conducted at least 1 week after step (a). In an embodiment of the application, step (b) is conducted at least 2 weeks after step (a).

In an embodiment of the application, the HBV polymerase antigen of the first composition is capable of inducing an immune response in the human subject against at least two HBV genotypes, preferably the HBV polymerase antigen is capable of inducing a T cell response in the human subject against at least HBV genotypes B, C, and D, and more preferably the HBV polymerase antigen is capable of inducing a CD8 T cell response in the human subject against at least HBV genotypes A, B, C, and D.

In an embodiment of the application, the HBV polymerase antigen of the first composition comprises the amino acid sequence of SEQ ID NO: 4. The first polynucleotide sequence of the first composition can, for example, be at least 90% identical to SEQ ID NO: 19. In an embodiment of the application, the first polynucleotide sequence of the first composition comprises the polynucleotide sequence of SEQ ID NO:19.

In an embodiment of the application, the HBV polymerase antigen of the first composition comprises the amino acid sequence of SEQ ID NO: 4. In an embodiment of the application, the first polynucleotide sequence of the first composition is at least 90% identical to SEQ ID NO: 20. The first polynucleotide sequence of the first composition can, for example, comprise SEQ ID NO: 20.

In an embodiment of the application, the nucleic acid molecule of the first plasmid of the first composition further comprises a polynucleotide sequence encoding a signal sequence operably linked to the HBV polymerase antigen of the first composition. The signal sequence can, for example, comprise the amino acid sequence of SEQ ID NO: 6 or SEQ ID NO: 11, preferably the signal sequence is encoded by the polynucleotide sequence of SEQ ID NO: 5 or SEQ ID NO: 10.

In an embodiment of the application, the second polynucleotide sequence of the first composition is at least 90% identical to SEQ ID NO: 18. The second polynucleotide sequence of the first composition can, for example, comprise the polynucleotide sequence of SEQ ID NO: 18.

In an embodiment of the application, the first and second polynucleotide sequences of the first composition further comprise a promoter sequence, optionally one or more additional regulatory sequences, preferably the promoter sequence comprises the polynucleotide sequence of SEQ ID NO: 7, and the additional regulatory sequence is selected from the group consisting of an enhancer sequence of SEQ ID NO: 8 or SEQ ID NO: 15, and a polyadenylation signal sequence of SEQ ID NO: 16.

In an embodiment of the application, the enhanced immune response comprises an enhanced antibody response against the HBV antigen in the human subject. The enhanced immune response can, for example, comprise an enhanced CD8+ T cell response against the HBV antigen in the human subject. The enhanced immune response can, for example, comprise an enhanced CD4+ T cell response against the HBV antigen in the human subject.

Other aspects, features and advantages of the invention will be apparent from the following disclosure, including the detailed description of the invention and its preferred embodiments and the appended claims.

BRIEF DESCRIPTION OF THE DRAWINGS

The foregoing summary, as well as the following detailed description of the invention, will be better understood when read in conjunction with the appended drawings. It should be understood that the invention is not limited to the precise embodiments shown in the drawings.

In the drawings:

FIG. 1A is a diagram of the genome of hepatitis B virus (HBV); in the native virus, the polymerase protein (Pol) contains the coding sequence for the envelope proteins in a different open reading frame; the envelope proteins (pre-S1, pre-S2, and S) are in the same open reading frame; FIG. 1B shows the viral life cycle of HBV;

FIG. 2A shows the expression cassette for a truncated HBV core antigen, which contains a CMV promoter, an intron (a fragment derived from the human ApoAI gene—GenBank accession X01038 base pairs 295-523, harboring the ApoAI second intron), a human immunoglobulin secretion signal, followed by a coding sequence for a truncated HBV core antigen and a SV40 polyadenylation signal; FIG. 2B shows the expression cassette for a fusion protein of a truncated HBV core antigen operably linked to a HBV polymerase antigen, which is otherwise identical to the expression cassette for the truncated HBV core antigen except the HBV antigen; FIG. 2C shows an expression cassette comprising a HBV core antigen operably linked to a Pr13.5 long promoter and an expression cassette comprising a HBV polymerase antigen operably linked to a PrHyb promoter;

DETAILED DESCRIPTION OF THE INVENTION

Figure 1A:
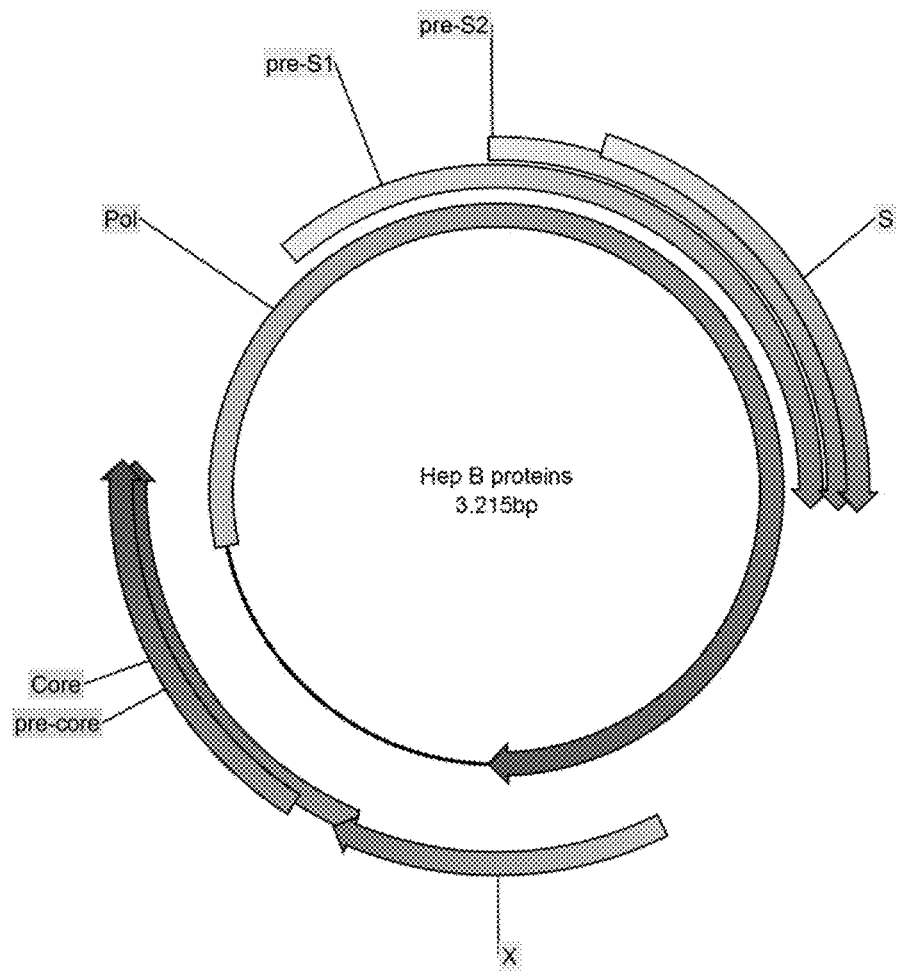
FIGS. 1A-1B depict the genome and viral life cycle of hepatitis B virus.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. Any of the aforementioned terms of "comprising," "containing," "including," and "having," whenever used herein in the context of an aspect or embodiment of the invention can be replaced with the term "consisting of" or "consisting essentially of" to vary scopes of the disclosure.

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, "subject" means any animal, preferably a mammal, most preferably a human, to whom will be or has been treated by a method according to an embodiment of the application. The term "mammal" as used herein, encompasses any mammal. Examples of mammals include, but are not limited to, cows, horses, sheep, pigs, cats, dogs, mice, rats, rabbits, guinea pigs, non-human primates (NHPs), such as monkeys or apes, humans, etc., more preferably a human.

The terms "adjuvant" and "immune stimulant" are used interchangeably herein, and are defined as one or more substances that cause stimulation of the immune system. In this context, an adjuvant is used to enhance an immune response to the adenovirus and/or MVA vectors of the application.

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

The terms "identical" or percent "identity," in the context of two or more nucleic acids or polypeptide sequences (e.g., HBV antigenic polypeptides and polynucleotides that encode them), refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1997) *Nucleic Acids Res.* 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased.

Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

As used herein, the term "enhanced" when used with respect to an immune response, such as a CD4+ T cell response, an antibody response, or a CD8+ T cell response, refers to an increase in the immune response in a subject administered with a prime-boost combination of MVA and adenovirus vectors according to the application, relative to the corresponding immune response observed from the subject administered with an MVA vector or an adenovirus of the application alone.

As used herein, the term "CD4+ or CD8+ T cell response" refers to a T cell immune response that is characterized by observing a high proportion of immunogen-specific CD4+ T cells or CD8+ T cells within the population of total responding T cells following vaccination. The total immunogen-specific T-cell response can be determined by an IFN-gamma ELISPOT assay. The immunogen-specific CD4+ or CD8+ T cell immune response can be determined by an ICS assay.

As used herein, the term "enhanced antibody response" refers to an increased antibody response in a subject administered with a prime-boost combination of MVA and adenovirus vectors according to the application, relative to the corresponding immune response observed from the subject administered with an MVA vector or an adenovirus of the application alone.

The term "adjuvant" is defined as one or more substances that cause stimulation of the immune system. In this context, an adjuvant is used to enhance an immune response to the plasmid, adenovirus, and/or MVA vectors of the application.

As used herein, the term "antigenic gene product or fragment thereof" or "antigenic protein" can include a bacterial, viral, parasitic, or fungal protein, or a fragment thereof. Preferably, an antigenic protein or antigenic gene product is capable of raising in a host a protective immune response, e.g., inducing an immune response against a disease or infection (e.g., a bacterial, viral, parasitic, or fungal disease or infection), and/or producing an immunity in (i.e., vaccinating) a subject against a disease or infection, that protects the subject against the disease or infection.

In an attempt to help the reader of the application, the description has been separated in various paragraphs or sections, or is directed to various embodiments of the application. These separations should not be considered as disconnecting the substance of a paragraph or section or embodiments from the substance of another paragraph or section or embodiments. To the contrary, one skilled in the art will understand that the description has broad application and encompasses all the combinations of the various sections, paragraphs and sentences that can be contemplated. The discussion of any embodiment is meant only to be exemplary and is not intended to suggest that the scope of the disclosure, including the claims, is limited to these examples. For example, while embodiments of HBV vectors of the application (e.g., plasmid DNA or viral vectors) described herein may contain particular components, including, but not limited to, certain promoter sequences, enhancer or regulatory sequences, signal peptides, coding sequence of an HBV antigen, polyadenylation signal sequences, etc. arranged in a particular order, those having ordinary skill in the art will appreciate that the concepts disclosed herein may equally apply to other components arranged in other orders that can be used in HBV vectors of the application. The application contemplates use of any of the applicable components in any combination having any sequence that can be used in HBV vectors of the application, whether or not a particular combination is expressly described.

Hepatitis B Virus (HBV)

As used herein "hepatitis B virus" or "HBV" refers to a virus of the hepadnaviridae family. HBV is a small (e.g., 3.2 kb) hepatotropic DNA virus that encodes four open reading frames and seven proteins. See FIG. 1A. The seven proteins encoded by HBV include small (S), medium (M), and large (L) surface antigen (HBsAg) or envelope (Env) proteins, pre-Core protein, core protein, viral polymerase (Pol), and HBx protein. HBV expresses three surface antigens, or envelope proteins, L, M, and S, with S being the smallest and L being the largest. The extra domains in the M and L proteins are named Pre-S2 and Pre-S1, respectively. Core protein is the subunit of the viral nucleocapsid. Pol is needed for synthesis of viral DNA (reverse transcriptase, RNaseH, and primer), which takes place in nucleocapsids localized to the cytoplasm of infected hepatocytes. PreCore is the core protein with an N-terminal signal peptide and is proteolytically processed at its N and C termini before secretion from infected cells, as the so-called hepatitis B e-antigen (HBeAg). HBx protein is required for efficient transcription of covalently closed circular DNA (cccDNA). HBx is not a viral structural protein. All viral proteins of HBV have their own mRNA except for core and polymerase, which share an mRNA. With the exception of the protein pre-Core, none of the HBV viral proteins are subject to post-translational proteolytic processing.

Figure 1B:
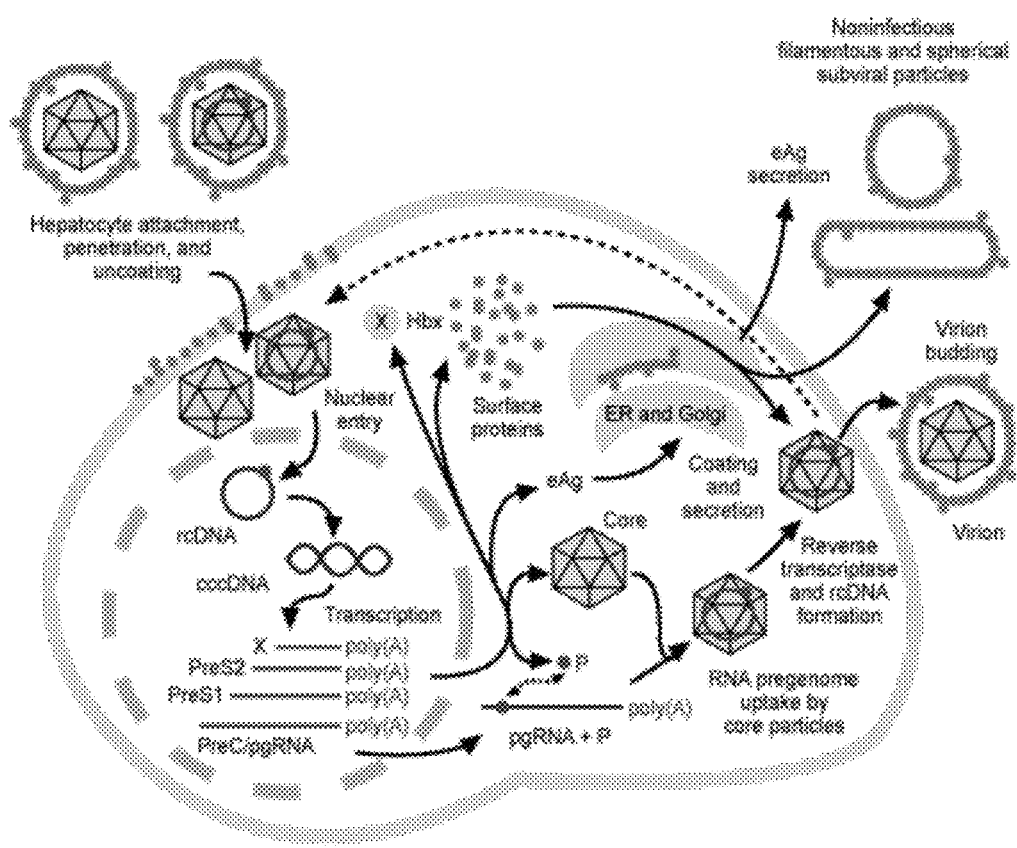

The HBV virion contains a viral envelope, nucleocapsid, and single copy of the partially double-stranded DNA genome. The nucleocapsid comprises 120 dimers of core protein and is covered by a capsid membrane embedded with the S, M, and L viral envelope or surface antigen proteins. After entry into the cell, the virus is uncoated and the capsid-containing relaxed circular DNA (rcDNA) with covalently bound viral polymerase migrates to the nucleus. During that process, phosphorylation of the Core protein induces structural changes, exposing a nuclear localization signal enabling interaction of the capsid with so-called importins. These importins mediate binding of the core protein to nuclear pore complexes upon which the capsid disassembles and polymerase/rcDNA complex is released into the nucleus. Within the nucleus the rcDNA becomes deproteinized (removal of polymerase) and is converted by host DNA repair machinery to a covalently closed circular DNA (cccDNA) genome from which overlapping transcripts encode for HBeAg, HBsAg, Core protein, viral polymerase and HBx protein. Core protein, viral polymerase, and pre-genomic RNA (pgRNA) associate in the cytoplasm and self-assemble into immature pgRNA-containing capsid particles, which further convert into mature rcDNA-capsids and function as a common intermediate that is either enveloped and secreted as infections virus particles or transported back to the nucleus to replenish and maintain a stable cccDNA pool. See FIG. 1B.

To date, HBV is divided into four serotypes (adr, adw, ayr, ayw) based on antigenic epitopes present on the envelope proteins, and into eight genotypes (A, B, C, D, E, F, G, and H) based on the sequence of the viral genome. The HBV genotypes are distributed over different geographic regions. For example, the most prevalent genotypes in Asia are genotypes B and C. Genotype D is dominant in Africa, the Middle East, and India, whereas genotype A is widespread in Northern Europe, sub-Saharan Africa, and West Africa.

HBV Antigens

As used herein, the terms "HBV antigen," "antigenic polypeptide of HBV," "HBV antigenic polypeptide," "HBV antigenic protein," "HBV immunogenic polypeptide," and "HBV immunogen" all refer to a polypeptide capable of inducing an immune response, e.g., a humoral and/or cellular mediated response, against an HBV in a subject. The HBV antigen can be a polypeptide of HBV, a fragment or epitope thereof, or a combination of multiple HBV polypeptides, portions or derivatives thereof. An HBV antigen is capable of raising in a host a protective immune response, e.g., inducing an immune response against a viral disease or infection, and/or producing an immunity (i.e., vaccinates) a subject against a viral disease or infection, that protects the subject against the viral disease or infection. For example, an HBV antigen can comprise a polypeptide or immunogenic fragment(s) thereof from any HBV protein, such as HBeAg, pre-core protein, HBsAg (S, M, or L proteins), core protein, viral polymerase, or HBx protein derived from any HBV genotype, e.g., genotype A, B, C, D, E, F, G, and/or H, or combination thereof.

(1) HBV Core Antigen

As used herein, each of the terms "HBV core antigen," "HBcAg" and "core antigen" refers to an HBV antigen capable of inducing an immune response, e.g., a humoral and/or cellular mediated response, against an HBV core protein in a subject. Each of the terms "core," "core polypeptide," and "core protein" refers to the HBV viral core protein. Full-length core antigen is typically 183 amino acids in length and includes an assembly domain (amino acids 1 to 149) and a nucleic acid binding domain (amino acids 150 to 183). The 34-residue nucleic acid binding domain is required for pre-genomic RNA encapsidation. This domain also functions as a nuclear import signal. It comprises 17 arginine residues and is highly basic, consistent with its function. HBV core protein is dimeric in solution, with the dimers self-assembling into icosahedral capsids. Each dimer of core protein has four α-helix bundles flanked by an α-helix domain on either side. Truncated HBV core proteins lacking the nucleic acid binding domain are also capable of forming capsids.

In an embodiment of the application, an HBV antigen is a truncated HBV core antigen. As used herein, a "truncated HBV core antigen," refers to an HBV antigen that does not contain the entire length of an HBV core protein but is capable of inducing an immune response against the HBV core protein in a subject. For example, an HBV core antigen can be modified to delete one or more amino acids of the highly positively charged (arginine rich) C-terminal nucleic acid binding domain of the core antigen, which typically contains seventeen arginine (R) residues. In some embodiments of the application, an HBV core antigen is a truncated HBV core protein. A truncated HBV core antigen of the application is preferably a C-terminally truncated HBV core protein which does not comprise the HBV core nuclear import signal and/or a truncated HBV core protein from which the C-terminal HBV core nuclear import signal has been deleted. In an embodiment of the application, a truncated HBV core antigen comprises a deletion in the C-terminal nucleic acid binding domain, such as a deletion of 1 to 34 amino acid residues of the C-terminal nucleic acid binding domain, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, or 34 amino acid residues, preferably a deletion of all 34 amino acid residues. In a preferred embodiment, a truncated HBV core antigen comprises a deletion in the C-terminal nucleic acid binding domain, preferably all 34 amino acid residues.

According to embodiments of the application, an HBV core antigen can be a consensus sequence derived from multiple HBV genotypes (e.g., genotypes A, B, C, D, E, F, G, and H). As used herein, "consensus sequence" means an artificial sequence of amino acids based on an alignment of amino acid sequences of homologous proteins, e.g., as determined by an alignment (e.g., using Clustal Omega) of amino acid sequences of homologous proteins. It can be the calculated order of most frequent amino acid residues, found at each position in a sequence alignment, based upon sequences of HBV antigens (e.g., core, pol, etc.) from at least 100 natural HBV isolates. A consensus sequence can be non-naturally occurring and different from the native viral sequences. Consensus sequences can be designed by aligning multiple HBV antigen sequences from different sources using a multiple sequence alignment tool, and at variable alignment positions, selecting the most frequent amino acid. Preferably, a consensus sequence of an HBV antigen is derived from HBV genotypes B, C, and D. The term "consensus antigen" is used to refer to an antigen having a consensus sequence.

A truncated HBV core antigen according to an embodiment of the application lacks the nucleic acid binding function, and is capable of inducing an immune response in a mammal against at least two HBV genotypes. Preferably the truncated HBV core antigen is capable of inducing a T cell response in a mammal against at least HBV genotypes B, C and D. More preferably, the truncated HBV core antigen is capable of inducing a CD8 T cell response in a human subject against at least HBV genotypes A, B, C and D.

In a preferred embodiment of the application, an HBV core antigen is a consensus antigen, preferably a consensus antigen derived from HBV genotypes B, C, and D, more preferably a truncated consensus antigen derived from HBV genotypes B, C, and D. An exemplary truncated HBV core consensus antigen according to the application consists of an amino acid sequence that is at least 90% identical to SEQ ID NO: 2, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9%, or 100% identical to SEQ ID NO: 2. SEQ ID NO: 2 is a core consensus antigen derived from HBV genotypes B, C, and D. SEQ ID NO: 2 contains a 34-amino acid C-terminal deletion of the highly positively charged (arginine rich) nucleic acid binding domain of the native core antigen.

In a particular embodiment of the application, an HBV core antigen is a truncated HBV antigen consisting of the amino acid sequence of SEQ ID NO: 2.

(2) HBV Polymerase Antigen

As used herein, the term "HBV polymerase antigen," "HBV Pol antigen" or "HBV pol antigen" refers to an HBV antigen capable of inducing an immune response, e.g., a humoral and/or cellular mediated response, against an HBV polymerase in a subject. Each of the terms "polymerase," "polymerase polypeptide," "Pol" and "pol" refers to the HBV viral DNA polymerase. The HBV viral DNA polymerase has four domains, including, from the N terminus to the C terminus, a terminal protein (TP) domain, which acts as a primer for minus-strand DNA synthesis; a spacer that is nonessential for the polymerase functions; a reverse transcriptase (RT) domain for transcription; and a RNase H domain.

In an embodiment of the application, an HBV antigen comprises an HBV Pol antigen, or any immunogenic fragment or combination thereof. The HBV Pol antigen can contain further modifications to improve immunogenicity of the antigen, such as by introducing mutations into the active sites of the polymerase and/or RNase domains to decrease or substantially eliminate certain enzymatic activities.

Preferably, an HBV Pol antigen of the application does not have reverse transcriptase activity and RNase H activity, and can be capable of inducing an immune response in a mammal against at least two HBV genotypes. Preferably the HBV Pol antigen is capable of inducing a T cell response in a mammal against at least HBV genotypes B, C and D. More preferably, the HBV Pol antigen is capable of inducing a CD8 T cell response in a human subject against at least HBV genotypes A, B, C and D.

Thus, in some embodiments of the application, an HBV Pol antigen is an inactivated Pol antigen. In an embodiment of the application, an inactivated HBV Pol antigen comprises one or more amino acid mutations in the active site of the polymerase domain. In another embodiment, an inactivated HBV Pol antigen comprises one or more amino acid mutations in the active site of the RNaseH domain. In a preferred embodiment, an inactivated HBV pol antigen comprises one or more amino acid mutations in the active site of both the polymerase domain and the RNaseH domain. For example, the "YXDD" motif in the polymerase domain of the HBV pol antigen required for nucleotide/metal ion binding can be mutated, e.g., by replacing one or more of the aspartate residues (D) with asparagine residues (N), eliminating or reducing metal coordination function, thereby decreasing or substantially eliminating reverse transcriptase function. Alternatively, or in addition to mutation of the "YXDD" motif, the "DEDD" motif in the RNaseH domain of the HBV pol antigen required for Mg2+ coordination can be mutated, e.g., by replacing one or more aspartate residues (D) with asparagine residues (N) and/or replacing the glutamate residue (E) with glutamine (Q), thereby decreasing or substantially eliminating RNaseH function. In a particular embodiment, an HBV pol antigen is modified by (1) mutating the aspartate residues (D) to asparagine residues (N) in the "YXDD" motif of the polymerase domain; and (2) mutating the first aspartate residue (D) to an asparagine residue (N) and the first glutamate residue (E) to a glutamine residue (N) in the "DEDD" motif of the RNaseH domain, thereby decreasing or substantially eliminating both the reverse transcriptase and RNaseH functions of the pol antigen.

In a preferred embodiment of the application, an HBV pol antigen is a consensus antigen, preferably a consensus antigen derived from HBV genotypes B, C, and D, more preferably an inactivated consensus antigen derived from HBV genotypes B, C, and D. An exemplary HBV pol consensus antigen according to the application comprises an amino acid sequence that is at least 90% identical to SEQ ID NO: 4, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 4, preferably at least 98% identical to SEQ ID NO: 4, such as at least 98%, 98.5%, 99%, 99.1%, 99.2%, 99.3%, 99.4%, 99.5%, 99.6%, 99.7%, 99.8%, 99.9% or 100% identical to SEQ ID NO: 4. SEQ ID NO: 4 is a pol consensus antigen derived from HBV genotypes B, C, and D comprising four mutations located in the active sites of the polymerase and RNaseH domains. In particular, the four mutations include mutation of the aspartic acid residues (D) to asparagine residues (N) in the "YXDD" motif of the polymerase domain; and mutation of the first aspartate residue (D) to an asparagine residue (N) and mutation of the glutamate residue (E) to a glutamine residue (Q) in the "DEDD" motif of the RNaseH domain.

In a particular embodiment of the application, an HBV pol antigen comprises the amino acid sequence of SEQ ID NO: 4. In other embodiments of the application, an HBV pol antigen consists of the amino acid sequence of SEQ ID NO: 4.

(3) Fusion of HBV Core Antigen and HBV Polymerase Antigen

As used herein the term "fusion protein" or "fusion" refers to a single polypeptide chain having at least two polypeptide domains that are not normally present in a single, natural polypeptide.

In an embodiment of the application, an HBV antigen comprises a fusion protein comprising a truncated HBV core antigen operably linked to a HBV pol antigen, or a HBV pol antigen operably linked to a truncated HBV core antigen, preferably via a linker.

As used herein, the term "linker" refers to a compound or moiety that acts as a molecular bridge to operably link two different molecules, wherein one portion of the linker is operably linked to a first molecule, and wherein another portion of the linker is operably linked to a second molecule. For example, in a fusion protein containing a first polypeptide and a second heterologous polypeptide, a linker serves primarily as a spacer between the first and second polypeptides. In one embodiment, the linker is made up of amino acids linked together by peptide bonds, preferably from 1 to 20 amino acids linked by peptide bonds, wherein the amino acids are selected from the 20 naturally occurring amino acids. In one embodiment, the 1 to 20 amino acids are selected from glycine, alanine, proline, asparagine, glutamine, and lysine. Preferably, a linker is made up of a majority of amino acids that are sterically unhindered, such as glycine and alanine. Exemplary linkers are polyglycines, particularly (Gly)5, (Gly)8; poly(Gly-Ala), and polyalanines. One exemplary suitable linker as shown in the Examples below is (AlaGly)$_n$, wherein n is an integer of 2 to 5.

Preferably, a fusion protein of the application is capable of inducing an immune response in a mammal against HBV core and HBV Pol of at least two HBV genotypes. Preferably the fusion protein is capable of inducing a T cell response in a mammal against at least HBV genotypes B, C and D. More preferably, the fusion protein is capable of inducing a CD8 T cell response in a human subject against at least HBV genotypes A, B, C and D.

In an embodiment of the application, a fusion protein comprises a truncated HBV core antigen having an amino acid sequence at least 90%, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9%, or 100% identical to SEQ ID NO: 2, a linker, and a HBV pol antigen having an amino acid sequence at least 90%, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9%, or 100%, identical to SEQ ID NO: 4.

In a preferred embodiment of the application, a fusion protein comprises a truncated HBV core antigen consisting of the amino acid sequence of SEQ ID NO: 2, a linker comprising (AlaGly)$_n$, wherein n is an integer of 2 to 5, and a HBV Pol antigen having the amino acid sequence of SEQ ID NO: 4. More preferably, a fusion protein according to an embodiment of the application comprises the amino acid sequence of SEQ ID NO: 12.

In an embodiment of the application, a fusion protein further comprises a signal sequence. Preferably, the signal sequence has the amino acid sequence of SEQ ID NO: 6 or SEQ ID NO: 11. More preferably, the fusion protein comprises the amino acid sequence of SEQ ID NO: 13.

Polynucleotides and Vectors

In another general aspect, the application provides a non-naturally occurring nucleic acid molecule encoding an HBV antigen according to an embodiment of the application, and a vector comprising the non-naturally occurring nucleic acid. A non-naturally occurring nucleic acid molecule can comprise any polynucleotide sequence encoding an HBV antigen of the application, which can be made using methods known in the art in view of the present disclosure. Preferably, a polynucleotide encodes at least one of an HBV core antigen and an HBV polymerase antigen of the application. A polynucleotide can be in the form of RNA or in the form of DNA obtained by recombinant techniques (e.g., cloning) or produced synthetically (e.g., chemical synthesis). The DNA can be single-stranded or double-stranded, or can contain portions of both double-stranded and single-stranded sequence. The DNA can, for example, comprise genomic DNA, cDNA, or combinations thereof. The polynucleotide can also be a DNA/RNA hybrid. The polynucleotides and vectors of the application can be used for recombinant protein production, expression of the protein in a host cell, or the production of viral particles. Preferably, a polynucleotide is DNA.

In an embodiment of the application, a non-naturally occurring nucleic acid molecule comprises a polynucleotide encoding a truncated HBV core antigen consisting of an amino acid sequence that is at least 90% identical to SEQ ID NO: 2, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 2, preferably at least 98%, 99% or 100% identical to SEQ ID NO: 2. In a particular embodiment of the application, a non-naturally occurring nucleic acid molecule encodes a truncated HBV core antigen comprising the amino acid sequence of SEQ ID NO: 2.

Examples of polynucleotide sequences of the application encoding a truncated HBV core antigen comprising the amino acid sequence of SEQ ID NO: 2 include, but are not limited to, a polynucleotide sequence at least 90% identical to SEQ ID NO: 1, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 1, preferably at least 98%, 99% or 100% identical to SEQ ID NO: 1. In particular embodiments of the application, the non-naturally occurring nucleic acid molecule encoding a truncated HBV core antigen comprises the polynucleotide sequence of SEQ ID NOs: 1, 17, or 18.

In an embodiment of the application, a non-naturally occurring nucleic acid molecule encodes a HBV polymerase antigen comprising an amino acid sequence that is at least 90% identical to SEQ ID NO: 4, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 4, preferably 100% identical to SEQ ID NO: 4. In a particular embodiment of the application, a non-naturally occurring nucleic acid molecule encodes a HBV polymerase antigen comprising the amino acid sequence of SEQ ID NO: 4.

Examples of polynucleotide sequences of the application encoding a HBV Pol antigen comprising the amino acid sequence of SEQ ID NO: 4 include, but are not limited to, a polynucleotide sequence at least 90% identical to SEQ ID NO:3, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 3, preferably at least 98%, 99% or 100% identical to SEQ ID NO: 3. In particular embodiments of the application, the non-naturally occurring nucleic acid molecule encoding a HBV pol antigen comprises the polynucleotide sequence of SEQ ID NOs: 3, 19, or 20.

In another embodiment of the application, a non-naturally occurring nucleic acid molecule encodes a fusion protein comprising a truncated HBV core antigen operably linked to a HBV Pol antigen, or a HBV Pol antigen operably linked to a truncated HBV core antigen. In a particular embodiment, a non-naturally occurring nucleic acid molecule of the application encodes a truncated HBV core antigen consisting of an amino acid sequence that is at least 90% identical to SEQ ID NO: 2, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 2, preferably 100% identical to SEQ ID NO: 2; a linker; and a HBV polymerase antigen comprising an amino acid sequence that is at least 90% identical to SEQ ID NO: 4, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 4, preferably at least 98%, 99% or 100% identical to SEQ ID NO: 4. In a particular embodiment of the application, a non-naturally occurring nucleic acid molecule encodes a fusion protein comprising a truncated HBV core antigen consisting of the amino acid sequence of SEQ ID NO: 2, a linker comprising (AlaGly)n, wherein n is an integer of 2 to 5; and a HBV Pol antigen comprising the amino acid sequence of SEQ ID NO: 4. In a particular embodiment of the application, a non-naturally occurring nucleic acid molecule encodes a fusion protein comprising the amino acid sequence of SEQ ID NO: 12.

Examples of polynucleotide sequences of the application encoding a fusion protein include, but are not limited to, a polynucleotide sequence at least 90% identical to SEQ ID NO: 1, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 1, preferably at least 98%, 99% or 100% identical to SEQ ID NO: 1, operably linked to a linker coding sequence at least 90% identical to SEQ ID NO: 14, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 14, preferably at least 98%, 99% or 100% identical to SEQ ID NO: 14, which is further operably linked a polynucleotide sequence at least 90% identical to SEQ ID NO: 3, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 3, preferably at least 98%, 99% or 100% identical to SEQ ID NO: 3. In particular embodiments of the application, a non-naturally occurring nucleic acid molecule encoding a fusion protein comprises SEQ ID NO: 1, operably linked to SEQ ID NO:14, which is further operably linked to SEQ ID NO: 3.

In another general aspect, the application relates to a vector comprising an isolated polynucleotide encoding an HBV antigen. As used herein, a "vector" is a nucleic acid molecule used to carry genetic material into another cell, where it can be replicated and/or expressed. Any vector known to those skilled in the art in view of the present disclosure can be used. Examples of vectors include, but are not limited to, plasmids, viral vectors (bacteriophage, animal viruses, and plant viruses), cosmids, and artificial chromosomes (e.g., YACs). Preferably, a vector is a DNA plasmid. A vector can be a DNA vector or an RNA vector. One of skill in the art can construct a vector of the application through standard recombinant techniques in view of the present disclosure.

According to embodiments of the application, a vector can be an expression vector. As used herein, the term "expression vector" refers to any type of genetic construct comprising a nucleic acid coding for an RNA capable of being transcribed. Expression vectors include, but are not limited to, vectors for recombinant protein expression, such as a DNA plasmid or a viral vector, and vectors for delivery of nucleic acid into a subject for expression in a tissue of the subject, such as a DNA plasmid or a viral vector. It will be appreciated by those skilled in the art that the design of the expression vector can depend on such factors as the choice of the host cell to be transformed, the level of expression of protein desired, etc.

Vectors according to embodiments of the application can contain a variety of regulatory sequences. As used herein, the term "regulatory sequence" refers to any sequence that allows, contributes or modulates the functional regulation of the nucleic acid molecule, including replication, duplication, transcription, splicing, translation, stability and/or transport of the nucleic acid or one of its derivative (i.e. mRNA) into the host cell or organism. In the context of the disclosure, this term encompasses promoters, enhancers and other expression control elements (e.g., polyadenylation signals and elements that affect mRNA stability).

In some embodiments, of the application, a vector is a non-viral vector. Examples of non-viral vectors include, but are not limited to, DNA plasmids, bacterial artificial chromosomes, yeast artificial chromosomes, bacteriophages, etc. Preferably, a non-viral vector is a DNA plasmid. A "DNA plasmid," which is used interchangeably with "DNA plasmid vector," "plasmid DNA" or "plasmid DNA vector," refers to a double-stranded and generally circular DNA sequence that is capable of autonomous replication in a suitable host cell. DNA plasmids used for expression of an encoded polynucleotide typically comprise an origin of replication, a multiple cloning site, and a selectable marker, which for example, can be an antibiotic resistance gene. Examples of DNA plasmids suitable for use in the application include, but are not limited to, commercially available expression vectors for use in well-known expression systems (including both prokaryotic and eukaryotic systems), such as pSE420 (Invitrogen, San Diego, Calif.), which can be used for production and/or expression of protein in *Escherichia coli*; pYES2 (Invitrogen, Thermo Fisher Scientific), which can be used for production and/or expression in *Saccharomyces cerevisiae* strains of yeast; MAXBAC® complete baculovirus expression system (Thermo Fisher Scientific), which can be used for production and/or expression in insect cells; pcDNA™ or pcDNA3™ (Life Technologies, Thermo Fisher Scientific), which can be used for high level constitutive protein expression in mammalian cells; and pVAX or pVAX-1 (Life Technologies, Thermo Fisher Scientific), which can be used for high-level transient expression of a protein of interest in most mammalian cells. The backbone of any commercially available DNA plasmid can be modified to optimize protein expression in the host cell, such as to reverse the orientation of certain elements (e.g., origin of replication and/or antibiotic resistance cassette), replace a promoter endogenous to the plasmid (e.g., the promoter in the antibiotic resistance cassette), and/or replace the polynucleotide sequence encoding transcribed proteins (e.g., the coding sequence of the antibiotic resistance gene), by using routine techniques and readily available starting materials. (See e.g., Sambrook et al., Molecular Cloning a Laboratory Manual, Second Ed. Cold Spring Harbor Press (1989)).

In a preferred embodiment of the application, a DNA plasmid is an expression vector suitable for protein expression in mammalian host cells. Expression vectors suitable for protein expression in mammalian host cells include, but are not limited to, pcDNA™, pcDNA3TM, pVAX, pVAX-1, ADVAX, NTC8454, etc. Preferably, the expression vector is based on pVAX-1, which can be further modified to optimize protein expression in mammalian cells. pVAX-1 is a commonly used plasmid in DNA vaccines, and contains a strong human immediate early cytomegalovirus (CMV-IE) promoter followed by the bovine growth hormone (bGH)-derived polyadenylation sequence (pA). pVAX-1 further contains a pUC origin of replication and kanamycin resistance gene driven by a small prokaryotic promoter that allows for bacterial plasmid propagation.

In an embodiment of the application, a vector is a viral vector. In general, viral vectors are genetically engineered viruses carrying modified viral DNA or RNA that has been rendered non-infectious, but still contains viral promoters and transgenes, thus allowing for translation of the transgene through a viral promoter. Because viral vectors are frequently lacking infectious sequences, they require helper viruses or packaging lines for large-scale transfection. Examples of viral vectors suitable for use with the application include, but are not limited to adenoviral vectors, Modified Vaccinia Ankara (MVA) vectors, adeno-associated virus vectors, pox virus vectors, enteric virus vectors, Venezuelan Equine Encephalitis virus vectors, Semliki Forest Virus vectors, Tobacco Mosaic Virus vectors, lentiviral vectors, etc.

According to embodiments of the application, a vector, e.g., a DNA plasmid or a viral vector, can comprise any regulatory elements to establish conventional function(s) of the vector, including but not limited to replication and expression of the HBV antigen(s) encoded by the polynucleotide sequence of the vector. Regulatory elements include, but are not limited to, a promoter, an enhancer, a polyadenylation signal, translation stop codon, a ribosome binding element, a transcription terminator, selection markers, origin of replication, etc. A vector can comprise one or more expression cassettes. An "expression cassette" is part of a vector that directs the cellular machinery to make RNA and protein. An expression cassette typically comprises three components: a promoter sequence, an open reading frame, and a 3'-untranslated region (UTR) optionally comprising a polyadenylation signal. An open reading frame (ORF) is a reading frame that contains a coding sequence of a protein of interest (e.g., HBV antigen) from a start codon to a stop codon. Regulatory elements of the expression cassette can be operably linked to a polynucleotide sequence encoding an HBV antigen of interest. As used herein, the term "operably linked" is to be taken in its broadest reasonable context, and refers to a linkage of polynucleotide elements in a functional relationship. A polynucleotide is "operably linked" when it is placed into a functional relationship with another polynucleotide. For instance, a promoter is operably linked to a coding sequence if it affects the transcription of the coding sequence.

In some embodiments, a vector comprises a promoter sequence, preferably within an expression cassette, to control expression of an HBV antigen of interest. The term "promoter" is used in its conventional sense, and refers to a nucleotide sequence that initiates the transcription of an operably linked nucleotide sequence. A promoter is located on the same strand near the nucleotide sequence it transcribes. Promoters can be a constitutive, inducible, or repressible. Promoters can be naturally occurring or synthetic. A promoter can be derived from sources including, viral, bacterial, fungal, plants, insects, and animals. A promoter can be a homologous promoter (i.e., derived from the same genetic source as the vector) or a heterologous promoter (i.e., derived from a different vector or genetic source). For example, if the vector to be employed is a DNA plasmid, the promoter can be endogenous to the plasmid (homologous) or derived from other sources (heterologous). Preferably, the promoter is located upstream of the polynucleotide encoding an HBV antigen within an expression cassette.

Examples of promoters suitable for use in the application include, but are not limited to, a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter (CMV-IE), Epstein Barr virus (EBV) promoter, or a Rous sarcoma virus (RSV) promoter. Additional promoters suitable for use in the application include, but are not limited to, an RSV promoter, the retrovirus LTR, the adenovirus major late promoter, and various poxvirus promoters including, but not limited to the following vaccinia virus or MVA-derived and FPV-derived promoters: the 30K promoter, the I3 promoter, the PrS promoter, the PrHyb, the PrS5E promoter, the Pr7.5K, the Pr13.5 long promoter, the 40K promoter, the MVA-40K promoter, the FPV 40K promoter, 30 k promoter, the PrSynIIm promoter, the PrLE1 promoter, and the PR1238 promoter. Additional promoters are further described in WO 2010/060632, WO 2010/102822, WO 2013/189611 and WO 2014/063832, and WO2017/021776, which are incorporated fully by reference herein.

A promoter can also be a promoter from a human gene such as human actin, human myosin, human hemoglobin, human muscle creatine, or human metalothionein. A promoter can also be a tissue specific promoter, such as a muscle or skin specific promoter, natural or synthetic.

In a preferred embodiment of the application, a promoter is a strong eukaryotic promoter, preferably a cytomegalovirus immediate early (CMV-IE) promoter. A nucleotide sequence of an exemplary CMV-IE promoter is shown in SEQ ID NO: 7.

In another preferred embodiment of the application, a promoter is a poxviral promoter, preferably a promoter selected from PrMVA 13.5 long and/or PrHyb. Nucleotide sequences for an exemplary Pr13.5 long promoter and a PrHyb promoter are shown as SEQ ID NO:25 and 26, respectively.

In some embodiments, a vector comprises additional polynucleotide sequences that stabilize the expressed transcript, enhance nuclear export of the RNA transcript, and/or improve transcriptional-translational coupling. Examples of such sequences include polyadenylation signals and enhancer sequences. A polyadenylation signal is typically located downstream of the coding sequence for a protein of interest (e.g., an HBV antigen) within an expression cassette of the vector. Enhancer sequences are regulatory DNA sequences that, when bound by transcription factors, enhance the transcription of an associated gene. An enhancer sequence is preferably located upstream of the polynucleotide sequence encoding an HBV antigen, but downstream of a promoter sequence within an expression cassette of the vector.

Any polyadenylation signal known to those skilled in the art in view of the present disclosure can be used. For example, the polyadenylation signal can be a SV40 polyadenylation signal (e.g., SEQ ID NO: 16), LTR polyadenylation signal, bovine growth hormone (bGH) polyadenylation signal, human growth hormone (hGH) polyadenylation signal, or human β-globin polyadenylation signal. In a preferred embodiment of the application, a polyadenylation signal is a bovine growth hormone (bGH) polyadenylation signal. A nucleotide sequence of an exemplary bGH polyadenylation signal is shown in SEQ ID NO:9.

Any enhancer sequence known to those skilled in the art in view of the present disclosure can be used. For example, an enhancer sequence can be human actin, human myosin, human hemoglobin, human muscle creatine, or a viral enhancer, such as one from CMV, HA, RSV, or EBV. Examples of particular enhancers include, but are not limited to, Woodchuck HBV Post-transcriptional regulatory element (WPRE), intron/exon sequence derived from human apolipoprotein A1 precursor, untranslated R-U5 domain of the human T-cell leukemia virus type 1 (HTLV-1) long terminal repeat (LTR), a splicing enhancer, a synthetic rabbit β-globin intron, or any combination thereof. In a preferred embodiment of the application, an enhancer sequence is a composite sequence of three consecutive elements of the untranslated R-U5 domain of HTLV-1 LTR, rabbit β-globin intron, and a splicing enhancer, which is referred to herein as "a triple enhancer sequence." A nucleotide sequence of an exemplary triple enhancer sequence is shown in SEQ ID NO: 8. Another exemplary enhancer sequence is an ApoAI gene fragment shown in SEQ ID NO: 15.

In some embodiments, a vector comprises a polynucleotide sequence encoding a signal peptide sequence. Preferably, the polynucleotide sequence encoding the signal peptide sequence is located upstream of the polynucleotide sequence encoding an HBV antigen. Signal peptides typically direct localization of a protein, facilitate secretion of the protein from the cell in which it is produced, and/or improve antigen expression and cross-presentation to antigen-presenting cells. A signal peptide can be present at the N-terminus of an HBV antigen when expressed from the vector, but is cleaved off by signal peptidase, e.g., upon secretion from a cell. An expressed protein in which a signal peptide has been cleaved is often referred to as the "mature protein." Any signal peptide known in the art in view of the present disclosure can be used. For example, a signal peptide can be a cystatin S signal peptide; an immunoglobulin (Ig) secretion signal, such as the Ig heavy chain gamma signal peptide SPIgG or the Ig heavy chain epsilon signal peptide SPIgE.

In a preferred embodiment of the application, a signal peptide sequence is a cystatin S signal peptide. Exemplary nucleic acid and amino acid sequences of a cystatin S signal peptide are shown in SEQ ID NOs: 5 and 6, respectively. Exemplary nucleic acid and amino acid sequences of an immunoglobulin secretion signal are shown in SEQ ID NOs: 10 and 27 and SEQ ID NO: 11, respectively.

A vector, such as a DNA plasmid, can also include a bacterial origin of replication and an antibiotic resistance expression cassette for selection and maintenance of the plasmid in bacterial cells, e.g., E. coli. Bacterial origins of replication and antibiotic resistance cassettes can be located in a vector in the same orientation as the expression cassette encoding an HBV antigen, or in the opposite (reverse) orientation. An origin of replication (ORI) is a sequence at which replication is initiated, enabling a plasmid to reproduce and survive within cells. Examples of ORIs suitable for use in the application include, but are not limited to ColE1, pMB1, pUC, pSC101, R6K, and 15A, preferably pUC. An exemplary nucleotide sequence of a pUC ORI is shown in SEQ ID NO: 21.

Expression cassettes for selection and maintenance in bacterial cells typically include a promoter sequence operably linked to an antibiotic resistance gene. Preferably, the promoter sequence operably linked to an antibiotic resistance gene differs from the promoter sequence operably linked to a polynucleotide sequence encoding a protein of interest, e.g., HBV antigen. The antibiotic resistance gene can be codon optimized, and the sequence composition of the antibiotic resistance gene is normally adjusted to bacterial, e.g., E. coli, codon usage. Any antibiotic resistance gene known to those skilled in the art in view of the present disclosure can be used, including, but not limited to, kanamycin resistance gene (Kan$^r$), ampicillin resistance gene (Amp$^r$), and tetracycline resistance gene (Tet$^r$), as well as genes conferring resistance to chloramphenicol, bleomycin, spectinomycin, carbenicillin, etc.

In another particular embodiment of the application, a vector is a viral vector, preferably an adenoviral vector, comprising an expression cassette including a polynucleotide encoding at least one of an HBV antigen selected from the group consisting of an HBV pol antigen comprising an amino acid sequence at least 98% identical to SEQ ID NO: 4, such as at least 98%, 98.5%, 99%, 99.1%, 99.2%, 99.3%, 99.4%, 99.5%, 99.6%, 99.7%, 99.8%, 99.9% or 100% identical to SEQ ID NO: 4, and a truncated HBV core antigen consisting of the amino acid sequence of SEQ ID NO: 2; an upstream sequence operably linked to the polynucleotide encoding the HBV antigen comprising, from 5' end to 3' end, a promoter sequence, preferably a CMV-IE promoter sequence of SEQ ID NO:7, an enhancer sequence, preferably a triple enhancer sequence of SEQ ID NO: 8 or an ApoA1 enhancer sequence of SEQ ID NO: 15, and a polynucleotide sequence encoding a signal peptide sequence, preferably a cystatin S signal having the amino acid sequence of SEQ ID NO: 6 or an immunoglobulin secretion signal having the amino acid sequence of SEQ ID NO: 11; and a downstream sequence operably linked to the polynucleotide encoding the HBV antigen comprising a polyadenylation signal, preferably a SV40 polyadenylation signal of SEQ ID NO: 16 or a bGH polyadenylation signal of SEQ ID NO: 9.

In another particular embodiment of the application, a vector is a viral vector, preferably a MVA vector, comprising an expression cassette including a polynucleotide encoding at least one of an HBV antigen selected from the group consisting of an HBV pol antigen comprising an amino acid sequence at least 98% identical to SEQ ID NO: 4, such as at least 98%, 98.5%, 99%, 99.1%, 99.2%, 99.3%, 99.4%, 99.5%, 99.6%, 99.7%, 99.8%, 99.9% or 100% identical to SEQ ID NO: 4, and a truncated HBV core antigen consisting of the amino acid sequence of SEQ ID NO: 2; an upstream sequence operably linked to the polynucleotide encoding the HBV antigen comprising, from 5' end to 3' end, a promoter sequence, preferably a PrMVA13.5 long promoter sequence of SEQ ID NO: 25 or a PrHyb promoter sequence of SEQ ID NO: 26, and a polynucleotide sequence encoding a signal peptide sequence, preferably a cystatin S signal having the amino acid sequence of SEQ ID NO: 6 or an immunoglobulin secretion signal having the amino acid sequence of SEQ ID NO: 11; and a downstream sequence operably linked to the polynucleotide encoding the HBV antigen comprising a polyadenylation signal or an early termination signal, wherein the early termination signal has a nucleotide sequence of SEQ ID NO: 28, or wherein the polyadenylation signal is selected from an SV40 polyadenylation signal having a polynucleotide sequence of SEQ ID NO: 16 or a bGH polyadenylation signal having a polynucleotide sequence of SEQ ID NO: 9, preferably the downstream sequence operably linked to the polynucleotide encoding the HBV antigen is an early termination signal having a nucleotide sequence of SEQ ID NO: 28.

In an embodiment of the application, a vector, such as a viral vector, encodes an HBV Pol antigen having the amino acid sequence of SEQ ID NO: 4. Preferably, the vector comprises a coding sequence for the HBV Pol antigen that is at least 90% identical to the polynucleotide sequence of SEQ ID NO: 3, such as 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 3, preferably 100% identical to SEQ ID NO: 3.

In another embodiment of the application, a vector, such as a viral vector, encodes a truncated HBV core antigen consisting of the amino acid sequence of SEQ ID NO:2. Preferably, the vector comprises a coding sequence for the truncated HBV core antigen that is at least 90% identical to the polynucleotide sequence of SEQ ID NO: 1, such as 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 1, preferably 100% identical to SEQ ID NO: 1.

In yet another embodiment of the application, a vector, such as a viral vector, encodes a fusion protein comprising an HBV Pol antigen having the amino acid sequence of SEQ ID NO: 4 and a truncated HBV core antigen consisting of the amino acid sequence of SEQ ID NO: 2. Preferably, the vector comprises a coding sequence for the fusion, which contains a coding sequence for the truncated HBV core antigen at least 90% identical to SEQ ID NO:1, such as 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO:1, preferably 98%, 99% or 100% identical to SEQ ID NO: 1, operably linked to a coding sequence for the HBV Pol antigen at least 90% identical to SEQ ID NO: 3, such as 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO:3, preferably 98%, 99% or 100% identical to SEQ ID NO: 3. Preferably, the coding sequence for the truncated HBV core antigen is operably linked to the coding sequence for the HBV Pol antigen via a coding sequence for a linker at least 90% identical to SEQ ID NO: 14, such as 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 14, preferably 98%, 99% or 100% identical to SEQ ID NO: 14. In particular embodiments of the application, the vector comprises a coding sequence for the fusion having SEQ ID NO: 1 operably linked to SEQ ID NO: 14, which is further operably linked to SEQ ID NO: 3.

The polynucleotides and expression vectors encoding the HBV antigens of the application can be made by any method known in the art in view of the present disclosure. For example, a polynucleotide encoding an HBV antigen can be introduced or "cloned" into an expression vector using standard molecular biology techniques, e.g., polymerase chain reaction (PCR), etc., which are well known to those skilled in the art.

Adenoviruses

In an aspect, the application provides a recombinant adenovirus comprising a heterologous nucleotide sequence encoding an antigenic HBV core antigen. In another aspect, the application provides a adenovirus comprising a heterologous nucleotide sequence encoding an antigenic HBV pol antigen. In another, the application provides a recombinant adenovirus vector comprising a first heterologous nucleotide sequence encoding an antigenic HBV core antigen and a second heterologous nucleotide sequence encoding an antigenic HBV pol antigen. In another aspect, the application provides a recombinant adenovirus comprising a heterologous nucleotide sequence encoding an antigenic HBV core-HBV pol fusion protein.

An adenovirus according to the application belongs to the family of the Adenoviridae and preferably is one that belongs to the genus Mastadenovirus. It can be a human adenovirus, but also an adenovirus that infects other species, including but not limited to a bovine adenovirus (e.g. bovine adenovirus 3, BAdV3), a canine adenovirus (e.g. CAdV2), a porcine adenovirus (e.g. PAdV3 or 5), or a simian adenovirus (which includes a monkey adenovirus and an ape adenovirus, such as a chimpanzee adenovirus or a gorilla adenovirus). Preferably, the adenovirus is a human adenovirus (HAdV, or AdHu; in the application a human adenovirus is meant if referred to as Ad without indication of species, e.g. the brief notation "Ad5" means the same as HAdV5, which is human adenovirus serotype 5), or a simian adenovirus such as chimpanzee or gorilla adenovirus (ChAd, AdCh, or SAdV).

Most advanced studies have been performed using human adenoviruses, and human adenoviruses are preferred according to certain aspects of the application. In certain preferred embodiments, the recombinant adenovirus according to the application is based upon a human adenovirus. In preferred embodiments, the recombinant adenovirus is based upon a human adenovirus serotype 5, 11, 26, 34, 35, 48, 49 or 50. According to a particularly preferred embodiment of the application, an adenovirus is a human adenovirus of one of the serotypes 26 or 35.

An advantage of these serotypes is a low seroprevalence and/or low pre-existing neutralizing antibody titers in the human population. Preparation of rAd26 vectors is described, for example, in WO 2007/104792 and in Abbink et al., (2007) Virol 81(9): 4654-63, both of which are incorporated by reference herein in their entirety. Exemplary genome sequences of Ad26 are found in GenBank Accession EF 153474 and in WO2007/104792 (see, e.g., SEQ ID NO:1). Preparation of rAd35 vectors is described, for example, in U.S. Pat. No. 7,270,811, in WO00/70071, and in Vogels et al., (2003) J Virol 77(15): 8263-71, all of which are incorporated by reference herein in their entirety. Exemplary genome sequences of Ad35 are found in GenBank Accession AC_000019 and in WO00/70071 (see, e.g., FIG. 6).

Simian adenoviruses generally also have a low seroprevalence and/or low pre-existing neutralizing antibody titers in the human population, and a significant amount of work has been reported using chimpanzee adenovirus vectors (e.g. U.S. Pat. No. 6,083,716; WO2005/071093; WO 2010/086189; WO 2010085984; Farina et al, 2001, J Virol 75: 11603-13; Cohen et al, 2002, J Gen Virol 83: 151-55; Kobinger et al, 2006, Virology 346: 394-401; Tatsis et al., 2007, Molecular Therapy 15: 608-17; see also review by Bangari and Mittal, 2006, Vaccine 24: 849-62; and review by Lasaro and Ertl, 2009, Mol Ther 17: 1333-39). Hence, in other preferred embodiments, the recombinant adenovirus according to the application is based upon a simian adenovirus, e.g. a chimpanzee adenovirus. In an embodiment of the application, the recombinant adenovirus is based upon simian adenovirus type 1, 3, 7, 8, 21, 22, 23, 24, 25, 26, 27.1, 28.1, 29, 30, 31.1, 32, 33, 34, 35.1, 36, 37.2, 39, 40.1, 41.1, 42.1, 43, 44, 45, 46, 48, 49, 50 or SA7P.

Adenoviral Vectors rAd26 and rAd35

In a preferred embodiment of the application, the adenoviral vectors comprise capsid proteins from two rare serotypes: Ad26 and Ad35. In the typical embodiment, the vector is an rAd26 or rAd35 virus.

Thus, the vectors that can be used in the application comprise an Ad26 or Ad35 capsid protein (e.g., a fiber, penton or hexon protein). One of skill will recognize that it is not necessary that an entire Ad26 or Ad35 capsid protein be used in the vectors of the application. Thus, chimeric capsid proteins that include at least a part of an Ad26 or Ad35 capsid protein can be used in the vectors of the application. The vectors of the application may also comprise capsid proteins in which the fiber, penton, and hexon proteins are each derived from a different serotype, so long as at least one capsid protein is derived from Ad26 or Ad35. In preferred embodiments, the fiber, penton and hexon proteins are each derived from Ad26 or each from Ad35.

One of skill will recognize that elements derived from multiple serotypes can be combined in a single recombinant adenovirus vector. Thus, a chimeric adenovirus that combines desirable properties from different serotypes can be produced. Thus, in some embodiments, a chimeric adenovirus of the application could combine the absence of pre-existing immunity of the Ad26 and Ad35 serotypes with characteristics such as temperature stability, assembly, anchoring, production yield, redirected or improved infection, stability of the DNA in the target cell, and the like.

In an embodiment of the application the recombinant adenovirus vector useful in the application is derived mainly or entirely from Ad35 or from Ad26 (i.e., the vector is rAd35 or rAd26). In some embodiments, the adenovirus is replication deficient, e.g. because it contains a deletion in the E1 region of the genome. For the adenoviruses of the application, being derived from Ad26 or Ad35, it is typical to exchange the E4-orf6 coding sequence of the adenovirus with the E4-orf6 of an adenovirus of human subgroup C, such as Ad5. This allows propagation of such adenoviruses in well-known complementing cell lines that express the E1 genes of Ad5, such as for example 293 cells, PER.C6 cells, and the like (see, e.g. Havenga et al, 2006, J Gen Virol 87: 2135-43; WO 03/104467). In an embodiment of the application, the adenovirus is a human adenovirus of serotype 35, with a deletion in the E1 region into which the nucleic acid encoding the antigen has been cloned, and with an E4 orf6 region of Ad5. In an embodiment of the application, the adenovirus is a human adenovirus of serotype 26, with a deletion in the E1 region into which the nucleic acid encoding the antigen has been cloned, and with an E4 orf6 region of Ad5. For the Ad35 adenovirus, it is typical to retain the 3' end of the E1B 55K open reading frame in the adenovirus, for instance the 166 bp directly upstream of the pIX open reading frame or a fragment comprising this such as a 243 bp fragment directly upstream of the pIX start codon, marked at the 5' end by a Bsu36I restriction site, since this increases the stability of the adenovirus because the promoter of the pIX gene is partly residing in this area (see, e.g. Havenga et al, 2006, supra; WO 2004/001032).

The preparation of recombinant adenoviral vectors is well known in the art. Preparation of rAd26 vectors is described, for example, in WO 2007/104792 and in Abbink et al., (2007) Virol 81(9): 4654-63. Exemplary genome sequences of Ad26 are found in GenBank Accession EF 153474 and in SEQ ID NO:1 of WO 2007/104792. Preparation of rAd35 vectors is described, for example, in U.S. Pat. No. 7,270,811 and in Vogels et al., (2003) J Virol 77(15): 8263-71. An exemplary genome sequence of Ad35 is found in GenBank Accession AC_000019.

In an embodiment of the application, the vectors useful in the application include those described in WO2012/082918, the disclosure of which is incorporated herein by reference in its entirety.

Typically, a vector useful in the application is produced using a nucleic acid comprising the entire recombinant adenoviral genome (e.g., a plasmid, cosmid, or baculovirus vector). Thus, the application also provides isolated nucleic acid molecules that encode the adenoviral vectors of the application. The nucleic acid molecules of the application may be in the form of RNA or in the form of DNA obtained by cloning or produced synthetically. The DNA may be double-stranded or single-stranded.

The adenovirus vectors useful in the application are typically replication defective. In these embodiments, the virus is rendered replication-defective by deletion or inactivation of regions critical to replication of the virus, such as the E1 region. The regions can be substantially deleted or inactivated by, for example, inserting the gene of interest (usually linked to a promoter). In some embodiments, the vectors of the application may contain deletions in other regions, such as the E2, E3 or E4 regions or insertions of heterologous genes linked to a promoter. For E2- and/or E4-mutated adenoviruses, generally E2- and/or E4-complementing cell lines are used to generate recombinant adenoviruses. Mutations in the E3 region of the adenovirus need not be complemented by the cell line, since E3 is not required for replication.

A packaging cell line is typically used to produce sufficient amount of adenovirus vectors of the application. A packaging cell is a cell that comprises those genes that have been deleted or inactivated in a replication-defective vector, thus allowing the virus to replicate in the cell. Suitable cell lines include, for example, PER.C6, 911, 293, and E1 A549.

As noted above, a wide variety of Hepatitis B virus (HBV) antigens (e.g., HBV core and HBV polymerase antigens) can be expressed in the vectors. If required, the heterologous gene encoding the HBV antigen can be codon-optimized to ensure proper expression in the treated host (e.g., human). Codon-optimization is a technology widely applied in the art. Typically, the heterologous gene is cloned into the E1 and/or the E3 region of the adenoviral genome.

The heterologous Hepatitis B virus gene may be under the control of (i.e., operably linked to) an adenovirus-derived promoter (e.g., the Major Late Promoter) or may be under the control of a heterologous promoter. Examples of suitable heterologous promoters include the CMV promoter and the RSV promoter. Preferably, the promoter is located upstream of the heterologous gene of interest within an expression cassette.

MVA Vectors

MVA vectors useful for the application utilize attenuated virus derived from Modified Vaccinia Ankara virus. The MVA vectors express a wide variety of HBV antigens (e.g., HBV core and HBV polymerase antigens). In an aspect, the application provides a recombinant MVA vector comprising a heterologous nucleotide sequence encoding an antigenic HBV core antigen. In another aspect, the application provides a recombinant MVA vector comprising a heterologous nucleotide sequence encoding an antigenic HBV pol antigen. In an aspect, the application provides a recombinant MVA vector comprising a first heterologous nucleotide sequence encoding an antigenic HBV core antigen and a second heterologous nucleotide sequence encoding an antigenic HBV pol antigen. In another aspect, the application provides a recombinant MVA vector comprising a heterologous nucleotide sequence encoding an antigenic HBV core-HBV pol fusion protein.

Modified Vaccinia Virus Ankara ("MVA")

The man-made attenuated modified vaccinia virus Ankara ("MVA") was generated by 516 serial passages on chicken embryo fibroblasts of the Ankara strain of vaccinia virus (CVA) (for review see Mayr, A., et al. Infection 3, 6-14 (1975)). As a consequence of these long-term passages, the genome of the resulting MVA virus had about 31 kilobases of its genomic sequence deleted and, therefore, was described as highly host cell restricted for replication to avian cells (Meyer, H. et al., J. Gen. Virol. 72, 1031-1038 (1991)). It was shown in a variety of animal models that the resulting MVA was significantly avirulent compared to the fully replication competent starting material (Mayr, A. & Danner, K., Dev. Biol. Stand. 41: 225-34 (1978)).

An MVA virus useful in the practice of the application can include, but is not limited to, MVA-572 (deposited as ECACC V94012707 on Jan. 27, 1994); MVA-575 (deposited as ECACC V00120707 on Dec. 7, 2000), MVA-I721 (referenced in Suter et al., Vaccine 2009), and ACAM3000 (deposited as ATCC® PTA-5095 on Mar. 27, 2003).

More preferably the MVA used in accordance with the application includes MVA-BN and derivatives of MVA-BN. MVA-BN has been described in International PCT publication WO 02/042480. "Derivatives" of MVA-BN refer to viruses exhibiting essentially the same replication characteristics as MVA-BN, as described herein, but exhibiting differences in one or more parts of their genomes.

MVA-BN, as well as derivatives thereof, is replication incompetent, meaning a failure to reproductively replicate in vivo and in vitro. More specifically in vitro, MVA-BN or derivatives thereof have been described as being capable of reproductive replication in chicken embryo fibroblasts (CEF), but not capable of reproductive replication in the human keratinocyte cell line HaCat (Boukamp et al (1988), J. Cell Biol. 106:761-771), the human bone osteosarcoma cell line 143B (ECACC Deposit No. 91112502), the human embryo kidney cell line 293 (ECACC Deposit No. 85120602), and the human cervix adenocarcinoma cell line HeLa (ATCC Deposit No. CCL-2). Additionally, MVA-BN or derivatives thereof have a virus amplification ratio at least two fold less, more preferably three-fold less than MVA-575 in Hela cells and HaCaT cell lines. Tests and assay for these properties of MVA-BN and derivatives thereof are described in WO 02/42480 (U.S. Patent application No. 2003/0206926) and WO 03/048184 (U.S. Patent application No. 2006/0159699).

The term "not capable of reproductive replication" or "no capability of reproductive replication" in human cell lines in vitro as described in the previous paragraphs is, for example, described in WO 02/42480, which also teaches how to obtain MVA having the desired properties as mentioned above. The term applies to a virus that has a virus amplification ratio in vitro at 4 days after infection of less than 1 using the assays described in WO 02/42480 or in U.S. Pat. No. 6,761,893.

The term "failure to reproductively replicate" refers to a virus that has a virus amplification ratio in human cell lines in vitro as described in the previous paragraphs at 4 days after infection of less than 1. Assays described in WO 02/42480 or in U.S. Pat. No. 6,761,893 are applicable for the determination of the virus amplification ratio.

The amplification or replication of a virus in human cell lines in vitro as described in the previous paragraphs is normally expressed as the ratio of virus produced from an infected cell (output) to the amount originally used to infect the cell in the first place (input) referred to as the "amplification ratio". An amplification ratio of "1" defines an amplification status where the amount of virus produced from the infected cells is the same as the amount initially used to infect the cells, meaning that the infected cells are permissive for virus infection and reproduction. In contrast, an amplification ratio of less than 1, i.e., a decrease in output compared to the input level, indicates a lack of reproductive replication and therefore attenuation of the virus.

The advantages of MVA-based vaccine include their safety profile as well as availability for large scale vaccine production. Preclinical tests have revealed that MVA-BN demonstrates superior attenuation and efficacy compared to other MVA strains (WO 02/42480). An additional property of MVA-BN strains is the ability to induce substantially the same level of immunity in vaccinia virus prime/vaccinia virus boost regimes when compared to DNA-prime/vaccinia virus boost regimes.

The recombinant MVA-BN viruses, the most preferred embodiment herein, are considered to be safe because of their distinct replication deficiency in mammalian cells and their well-established avirulence. Furthermore, in addition to its efficacy, the feasibility of industrial scale manufacturing can be beneficial. Additionally, MVA-based vaccines can deliver multiple heterologous antigens and allow for simultaneous induction of humoral and cellular immunity.

MVA vectors useful for the application can be prepared using methods known in the art, such as those described in WO/2002/042480 and WO/2002/24224, the relevant disclosures of which are incorporated herein by references.

In a preferred embodiment of the application, the MVA vector(s) comprise a nucleic acid that encodes one or more antigenic proteins selected from the group consisting of HBV core antigen, HBV pol antigen, and a HBV core-HBV pol fusion antigen.

The HBV antigen protein may be inserted into one or more intergenic regions (IGR) of the MVA. In an embodiment of the application, the IGR is selected from IGR07/08, IGR 44/45, IGR 64/65, IGR 88/89, IGR 136/137, and IGR 148/149. In an embodiment of the application, less than 5, 4, 3, or 2 IGRs of the recombinant MVA comprise heterologous nucleotide sequences encoding antigenic determinants of a HBV core antigen and/or a HBV pol antigen. The heterologous nucleotide sequences may, additionally or alternatively, be inserted into one or more of the naturally occurring deletion sites, in particular into the main deletion sites I, II, III, IV, V, or VI of the MVA genome. In an embodiment of the application, less than 5, 4, 3, or 2 of the naturally occurring deletion sites of the recombinant MVA comprise heterologous nucleotide sequences encoding antigenic determinants of a HBV core antigen and/or a HBV pol antigen.

The number of insertion sites of MVA comprising heterologous nucleotide sequences encoding antigenic determinants of a HBV protein can be 1, 2, 3, 4, 5, 6, 7, or more. In an embodiment of the application, the heterologous nucleotide sequences are inserted into 4, 3, 2, or fewer insertion sites. Preferably, two insertion sites are used. In an embodiment of the application, three insertion sites are used. Preferably, the recombinant MVA comprises at least 2, 3, 4, 5, 6, or 7 genes inserted into 2 or 3 insertion sites.

The recombinant MVA viruses provided herein can be generated by routine methods known in the art. Methods to obtain recombinant poxviruses or to insert exogenous coding sequences into a poxviral genome are well known to the person skilled in the art. For example, methods for standard molecular biology techniques such as cloning of DNA, DNA and RNA isolation, Western blot analysis, RT-PCR and PCR amplification techniques are described in Molecular Cloning, A laboratory Manual (2nd Ed.) (J. Sambrook et al., Cold Spring Harbor Laboratory Press (1989)), and techniques for the handling and manipulation of viruses are described in Virology Methods Manual (B. W. J. Mahy et al. (eds.), Academic Press (1996)). Similarly, techniques and know-how for the handling, manipulation and genetic engineering of MVA are described in Molecular Virology: A Practical Approach (A. J. Davison & R. M. Elliott (Eds.), The Practical Approach Series, IRL Press at Oxford University Press, Oxford, UK (1993)(see, e.g., Chapter 9: Expression of genes by Vaccinia virus vectors)) and Current Protocols in Molecular Biology (John Wiley & Son, Inc. (1998)(see, e.g., Chapter 16, Section IV: Expression of proteins in mammalian cells using vaccinia viral vector)).

For the generation of the various recombinant MVAs disclosed herein, different methods may be applicable. The DNA sequence to be inserted into the virus can be placed into an *E. coli* plasmid construct into which DNA homologous to a section of DNA of the MVA has been inserted. Separately, the DNA sequence to be inserted can be ligated to a promoter. The promoter-gene linkage can be positioned in the plasmid construct so that the promoter-gene linkage is flanked on both ends by DNA homologous to a DNA sequence flanking a region of MVA DNA containing a non-essential locus. The resulting plasmid construct can be amplified by propagation within *E. coli* bacteria and isolated. The isolated plasmid containing the DNA gene sequence to be inserted can be transfected into a cell culture, e.g., of chicken embryo fibroblasts (CEFs), at the same time the culture is infected with MVA. Recombination between homologous MVA DNA in the plasmid and the viral genome, respectively, can generate an MVA modified by the presence of foreign DNA sequences.

According to a preferred embodiment, a cell of a suitable cell culture as, e.g., CEF cells, can be infected with a poxvirus. The infected cell can be, subsequently, transfected with a first plasmid vector comprising a foreign or heterologous gene or genes, preferably under the transcriptional control of a poxvirus expression control element. As explained above, the plasmid vector also comprises sequences capable of directing the insertion of the exogenous sequence into a selected part of the poxviral genome. Optionally, the plasmid vector also contains a cassette comprising a marker and/or selection gene operably linked to a poxviral promoter.

Suitable marker or selection genes are, e.g., the genes encoding the green fluorescent protein, β-galactosidase, neomycin-phosphoribosyltransferase or other markers. The use of selection or marker cassettes simplifies the identification and isolation of the generated recombinant poxvirus. However, a recombinant poxvirus can also be identified by PCR technology. Subsequently, a further cell can be infected with the recombinant poxvirus obtained as described above and transfected with a second vector comprising a second foreign or heterologous gene or genes. In case, this gene shall be introduced into a different insertion site of the poxviral genome, the second vector also differs in the poxvirus-homologous sequences directing the integration of the second foreign gene or genes into the genome of the poxvirus. After homologous recombination has occurred, the recombinant virus comprising two or more foreign or heterologous genes can be isolated. For introducing additional foreign genes into the recombinant virus, the steps of infection and transfection can be repeated by using the recombinant virus isolated in previous steps for infection and by using a further vector comprising a further foreign gene or genes for transfection.

Alternatively, the steps of infection and transfection as described above are interchangeable, i.e., a suitable cell can at first be transfected by the plasmid vector comprising the foreign gene and, then, infected with the poxvirus. As a further alternative, it is also possible to introduce each foreign gene into different viruses, co-infect a cell with all the obtained recombinant viruses and screen for a recombinant including all foreign genes. A third alternative is ligation of DNA genome and foreign sequences in vitro and reconstitution of the recombined vaccinia virus DNA genome using a helper virus. A fourth alternative is homologous recombination in *E. coli* or another bacterial species between a vaccinia virus genome, such as MVA, cloned as a bacterial artificial chromosome (BAC) and a linear foreign sequence flanked with DNA sequences homologous to sequences flanking the desired site of integration in the vaccinia virus genome.

The heterologous HBV gene (e.g., a HBV core antigen, a HBV pol antigen, and/or a HBV core-HBV-pol fusion protein) may be under the control of (i.e., operably linked to) one or more poxvirus promoters. In an embodiment of the application, the poxvirus promoter is a Pr7.5 promoter, a hybrid early/late promoter, or a PrS promoter, a PrS5E promoter, a synthetic or natural early or late promoter, or a cowpox virus ATI promoter.

Compositions, Immunogenic Combinations, and Vaccines

The application also relates to compositions, immunogenic combinations, more particularly kits, and vaccines comprising one or more HBV antigens, polynucleotides, and/or vectors encoding one more HBV antigens according to the application. Any of the HBV antigens, polynucleotides (including RNA and DNA), and/or vectors of the application described herein can be used in the compositions, immunogenic combinations or kits, and vaccines of the application.

In a general aspect, the application provides a composition comprising an isolated or non-naturally occurring nucleic acid molecule (DNA or RNA) encoding a truncated HBV core antigen consisting of an amino acid sequence that is at least 90% identical to SEQ ID NO: 2 or a HBV polymerase antigen comprising an amino acid sequence that is at least 90% identical to SEQ ID NO: 4, a vector comprising the isolated or non-naturally occurring nucleic acid molecule, and/or an isolated or non-naturally occurring polypeptide encoded by the isolated or non-naturally occurring nucleic acid molecule.

In an embodiment of the application, a composition comprises an isolated or non-naturally occurring nucleic acid molecule (DNA or RNA) encoding a truncated HBV core antigen consisting of an amino acid sequence that is at least 90% identical to SEQ ID NO: 2, preferably 100% identical to SEQ ID NO: 2.

In an embodiment of the application, a composition comprises an isolated or non-naturally occurring nucleic acid molecule (DNA or RNA) encoding a HBV pol antigen comprising an amino acid sequence that is at least 90% identical to SEQ ID NO: 4, preferably 100% identical to SEQ ID NO: 4.

In an embodiment of the application, a composition comprises an isolated or non-naturally occurring nucleic acid molecule (DNA or RNA) comprising a polynucleotide sequence encoding a truncated HBV core antigen consisting of an amino acid sequence that is at least 90% identical to SEQ ID NO: 2, preferably 100% identical to SEQ ID NO: 2; and an isolated or non-naturally occurring nucleic acid molecule (DNA or RNA) comprising a polynucleotide sequence encoding a HBV pol antigen comprising an amino acid sequence that is at least 90% identical to SEQ ID NO: 4, preferably 100% identical to SEQ ID NO: 4. The coding sequences for the truncated HBV core antigen and the HBV Pol antigen can be present in the same isolated or non-naturally occurring nucleic acid molecule (DNA or RNA), or in two different isolated or non-naturally occurring nucleic acid molecules (DNA or RNA).

In an embodiment of the application, a composition comprises a viral vector comprising a polynucleotide encoding a truncated HBV core antigen consisting of an amino acid sequence that is at least 90% identical to SEQ ID NO: 2, preferably 100% identical to SEQ ID NO: 2.

In an embodiment of the application, a composition comprises a viral vector comprising a polynucleotide encoding a HBV pol antigen comprising an amino acid sequence that is at least 90% identical to SEQ ID NO: 4, preferably 100% identical to SEQ ID NO: 4.

In an embodiment of the application, a composition comprises a viral vector comprising a polynucleotide encoding a truncated HBV core antigen consisting of an amino acid sequence that is at least 90% identical to SEQ ID NO: 2, preferably 100% identical to SEQ ID NO: 2; and a viral vector comprising a polynucleotide encoding a HBV pol antigen comprising an amino acid sequence that is at least 90% identical to SEQ ID NO: 4, preferably 100% identical to SEQ ID NO: 4. The vector comprising the coding sequence for the truncated HBV core antigen and the vector comprising the coding sequence for the HBV pol antigen can be the same vector, or two different vectors.

In an embodiment of the application, a composition comprises a viral vector comprising a polynucleotide encoding a fusion protein comprising a truncated HBV core antigen consisting of an amino acid sequence that is at least 90% identical to SEQ ID NO: 2, preferably 100% identical to SEQ ID NO: 2, operably linked to a HBV Pol antigen comprising an amino acid sequence that is at least 90% identical to SEQ ID NO: 4, preferably 100% identical to SEQ ID NO: 4, or vice versa. Preferably, the fusion protein further comprises a linker that operably links the truncated HBV core antigen to the HBV Pol antigen, or vice versa. Preferably, the linker has the amino acid sequence of (AlaGly)n, wherein n is an integer of 2 to 5.

In an embodiment of the application, a composition comprises an isolated or non-naturally occurring truncated HBV core antigen consisting of an amino acid sequence that is at least 90% identical to SEQ ID NO: 2, preferably 100% identical to SEQ ID NO: 2.

In an embodiment of the application, a composition comprises an isolated or non-naturally occurring HBV Pol antigen comprising an amino acid sequence that is at least 90% identical to SEQ ID NO: 4, preferably 100% identical to SEQ ID NO: 4.

In an embodiment of the application, a composition comprises an isolated or non-naturally occurring truncated HBV core antigen consisting of an amino acid sequence that is at least 90% identical to SEQ ID NO: 2, preferably 100% identical to SEQ ID NO: 2; and an isolated or non-naturally occurring HBV Pol antigen comprising an amino acid sequence that is at least 90% identical to SEQ ID NO: 4, preferably 100% identical to SEQ ID NO: 4.

In an embodiment of the application, a composition comprises an isolated or non-naturally occurring fusion protein comprising a truncated HBV core antigen consisting of an amino acid sequence that is at least 90% identical to SEQ ID NO: 2, preferably 100% identical to SEQ ID NO: 2, operably linked to a HBV Pol antigen comprising an amino acid sequence that is at least 90% identical to SEQ ID NO: 4, preferably 100% identical to SEQ ID NO: 4, or vice versa. Preferably, the fusion protein further comprises a linker that operably links the truncated HBV core antigen to the HBV Pol antigen, or vice versa. Preferably, the linker has the amino acid sequence of (AlaGly)n, wherein n is an integer of 2 to 5.

In another general aspect, the application relates to an immunogenic combination or a kit comprising polynucleotides expressing a truncated HBV core antigen and an HBV pol antigen according to embodiments of the application. Any polynucleotides and/or vectors encoding HBV core and pol antigens of the application described herein can be used in the immunogenic combinations or kits of the application.

According to embodiments of the application, the polynucleotides in a vaccine combination or kit can be linked or separate, such that the HBV antigens expressed from such polynucleotides are fused together or produced as separate proteins, whether expressed from the same or different polynucleotides. In one embodiment, the first and second polynucleotides are present in separate viral vectors used in combination either in the same or separate compositions, such that the expressed proteins are also separate proteins, but used in combination. In another embodiment, the HBV antigens encoded by the first and second polynucleotides can be expressed from the same viral vector, such that an HBV core-pol fusion antigen is produced. Optionally, the core and pol antigens can be joined or fused together by a short linker. Alternatively, the HBV antigens encoded by the first and second polynucleotides can be expressed independently from a single vector using a using a ribosomal slippage site (also known as cis-hydrolase site) between the core and pol antigen coding sequences. This strategy results in a bicistronic expression vector in which individual core and pol antigens are produced from a single mRNA transcript. The core and pol antigens produced from such a bicistronic expression vector can have additional N or C-terminal residues, depending upon the ordering of the coding sequences on the mRNA transcript. Examples of ribosomal slippage sites that can be used for this purpose include, but are not limited to, the FA2 slippage site from foot-and-mouth disease virus (FMDV). Another possibility is that the HBV antigens encoded by the first and second polynucleotides can be expressed independently from two separate vectors, one encoding the HBV core antigen and one encoding the HBV pol antigen.

In a preferred embodiment, the first and second polynucleotides are present in separate viral vectors. Preferably, the separate vectors are present in the same composition.

In a particular embodiment of the application, an immunogenic combination or kit comprises: a first vector, preferably a DNA plasmid or a viral vector, comprising a polynucleotide encoding a truncated HBV core antigen consisting of an amino acid sequence that is at least 90% identical to SEQ ID NO: 2, preferably 100% identical to SEQ ID NO: 2; and a second vector, preferably a DNA plasmid or a viral vector, comprising a polynucleotide encoding a HBV polymerase antigen comprising an amino acid sequence that is at least 98% identical to SEQ ID NO: 4, preferably 100% identical to SEQ ID NO: 4.

In one particular embodiment of the application, the first vector is a first DNA plasmid and the second vector is a second DNA plasmid. Each of the first and second DNA plasmids comprises an origin of replication, preferably a pUC ORI of SEQ ID NO: 21, and an antibiotic resistance cassette, preferably comprising a codon optimized Kan$^r$ (Kanamycin resistance) gene having a polynucleotide sequence that is at least 90% identical to SEQ ID NO: 22, preferably under control of a bla promoter, for instance the bla promoter shown in SEQ ID NO: 24. Each of the first and second DNA plasmids independently further comprises at least one of a promoter sequence, enhancer sequence, and a polynucleotide sequence encoding a signal peptide sequence operably linked to the first polynucleotide sequence or the second polynucleotide sequence. Preferably, each of the first and second DNA plasmids comprises an upstream sequence operably linked to the first polynucleotide or the second polynucleotide, wherein the upstream sequence comprises, from 5' end to 3' end, a promoter sequence of SEQ ID NO: 7, an enhancer sequence of SEQ ID NO: 8, and a polynucleotide sequence encoding a signal peptide sequence having the amino acid sequence of SEQ ID NO: 6. Each of the first and second DNA plasmids can also comprise a polyadenylation signal located downstream of the coding sequence of the HBV antigen, such as the bGH polyadenylation signal of SEQ ID NO: 9.

In one particular embodiment of the application, the first vector is a first viral vector and the second vector is a second viral vector. Preferably, each of the first and second viral vector is an adenoviral vector, more preferably an Ad26 or Ad35 vector, comprising an expression cassette including the polynucleotide encoding the HBV pol antigen or the truncated HBV core antigen of the application; an upstream sequence operably linked to the polynucleotide encoding the HBV antigen comprising, from 5' end to 3' end, a promoter sequence, preferably a CMV promoter sequence of SEQ ID NO: 7, an enhancer sequence, preferably an ApoAI gene fragment sequence of SEQ ID NO: 15 or a triple enhancer sequence of SEQ ID NO: 8, and a polynucleotide sequence encoding a signal peptide sequence, preferably a cystatin S signal having the amino acid sequence of SEQ ID NO: 6 or an immunoglobulin secretion signal having the amino acid sequence of SEQ ID NO: 11; and a downstream sequence operably linked to the polynucleotide encoding the HBV antigen comprising a polyadenylation signal, preferably a SV40 polyadenylation signal of SEQ ID NO: 16.

In a particular embodiment of the application, the first vector is a first viral vector and the second vector is a second viral vector. Preferably, each of the first and second viral vector is a MVA vector comprising an expression cassette including the polynucleotide encoding the HBV pol antigen and/or the truncated HBV core antigen of the application; an upstream sequence operably linked to the polynucleotide encoding the HBV antigen comprising, from 5' end to 3' end, a promoter sequence, preferably a PrMVA13.5 long promoter sequence of SEQ ID NO: 25 or a PrHyb promoter sequence of SEQ ID NO: 26, and a polynucleotide sequence encoding a signal peptide sequence, preferably a cystatin S signal having the amino acid sequence of SEQ ID NO: 6 or an immunoglobulin secretion signal having the amino acid sequence of SEQ ID NO: 11; and a downstream sequence operably linked to the polynucleotide encoding the HBV antigen comprising a polyadenylation signal or an early termination signal, wherein the early termination signal has a nucleotide sequence of SEQ ID NO:28, or wherein the polyadenylation signal is selected from an SV40 polyadenylation signal having a polynucleotide sequence of SEQ ID NO: 16 or a bGH polyadenylation signal having a polynucleotide sequence of SEQ ID NO: 9, preferably the downstream sequence operably linked to the polynucleotide encoding the HBV antigen is an early termination signal having a nucleotide sequence of SEQ ID NO: 28.

In an embodiment of the application, provided is a vaccine combination comprising (a) a first composition comprising an immunologically effective amount of an adenovirus vector comprising a first polynucleotide sequence encoding an HBV polymerase antigen comprising an amino acid sequence that is at least 98% identical to SEQ ID NO:4, wherein the HBV polymerase antigen does not have reverse transcriptase activity and RNase H activity; and (b) a second composition comprising an immunologically effective amount of a Modified Vaccinia Ankara (MVA) vector comprising a second polynucleotide sequence encoding an HBV polymerase antigen comprising an amino acid sequence that is at least 98% identical to SEQ ID NO: 4, wherein the HBV polymerase antigen does not have reverse transcriptase activity and RNase H activity; wherein the first composition is administered to the human subject for priming the immune response, and the second composition is administered to the human subject one or more times for boosting the immune response.

In an embodiment of the application, provided is a vaccine combination comprising (a) a first composition comprising an immunologically effective amount of a Modified Vaccinia Ankara (MVA) vector comprising a first polynucleotide sequence encoding an HBV polymerase antigen comprising an amino acid sequence that is at least 98% identical to SEQ ID NO:4, wherein the HBV polymerase antigen does not have reverse transcriptase activity and RNase H activity; and (b) a second composition comprising an immunologically effective amount of an adenovirus vector comprising a second polynucleotide sequence encoding an HBV polymerase antigen comprising an amino acid sequence that is at least 98% identical to SEQ ID NO: 4, wherein the HBV polymerase antigen does not have reverse transcriptase activity and RNase H activity; wherein the first composition is administered to the human subject for priming the immune response, and the second composition is administered to the human subject one or more times for boosting the immune response.

In those embodiments of the application in which an immunogenic combination comprises a first viral vector and a second viral vector, the amount of each of the first and second vectors is not particularly limited. For example, the first viral vector and the second viral vector can be present in a ratio of 10:1 to 1:10, by weight, such as 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, or 1:10, by weight. Preferably, the first and second viral vectors are present in a ratio of 1:1, by weight.

Compositions and immunogenic combinations of the application can comprise additional polynucleotides or vectors encoding additional HBV antigens and/or additional HBV antigens or immunogenic fragments thereof. However, in particular embodiments, the compositions and immunogenic combinations of the application do not comprise certain antigens.

In a particular embodiment, a composition or immunogenic combination or kit of the application does not comprise a HBsAg or a polynucleotide sequence encoding the HBsAg.

In another particular embodiment, a composition or immunogenic combination or kit of the application does not comprise a HBV L protein or a polynucleotide sequence encoding the HBV L protein.

In yet another particular embodiment, a composition or immunogenic combination of the application does not comprise a HBV envelope protein or a polynucleotide sequence encoding the HBV envelope protein.

Compositions and immunogenic combinations of the application can also comprise a pharmaceutically acceptable carrier. A pharmaceutically acceptable carrier is non-toxic and should not interfere with the efficacy of the active ingredient. Pharmaceutically acceptable carriers can include one or more excipients such as binders, disintegrants, swelling agents, suspending agents, emulsifying agents, wetting agents, lubricants, flavorants, sweeteners, preservatives, dyes, solubilizers and coatings. The precise nature of the carrier or other material can depend on the route of administration, e.g., intramuscular, intradermal, subcutaneous, oral, intravenous, cutaneous, intramucosal (e.g., gut), intranasal or intraperitoneal routes. For liquid injectable preparations, for example, suspensions and solutions, suitable carriers and additives include water, glycols, oils, alcohols, preservatives, coloring agents and the like. For solid oral preparations, for example, powders, capsules, caplets, gelcaps and tablets, suitable carriers and additives include starches, sugars, diluents, granulating agents, lubricants, binders, disintegrating agents and the like. For nasal sprays/inhalant mixtures, the aqueous solution/suspension can comprise water, glycols, oils, emollients, stabilizers, wetting agents, preservatives, aromatics, flavors, and the like as suitable carriers and additives.

Compositions and immunogenic combinations of the application can be formulated in any matter suitable for administration to a subject to facilitate administration and improve efficacy, including, but not limited to, oral (enteral) administration and parenteral injections. The parenteral injections include intravenous injection or infusion, subcutaneous injection, intradermal injection, and intramuscular injection. Compositions of the application can also be formulated for other routes of administration including transmucosal, ocular, rectal, long acting implantation, sublingual administration, under the tongue, from oral mucosa bypassing the portal circulation, inhalation, or intranasal.

In a preferred embodiment of the application, compositions and immunogenic combinations of the application are formulated for parental injection, preferably subcutaneous, intradermal injection, or intramuscular injection, more preferably intramuscular injection.

According to embodiments of the application, compositions and immunogenic combinations for administration will typically comprise a buffered solution in a pharmaceutically acceptable carrier, e.g., an aqueous carrier such as buffered saline and the like, e.g., phosphate buffered saline (PBS). The compositions and immunogenic combinations can also contain pharmaceutically acceptable substances as required to approximate physiological conditions such as pH adjusting and buffering agents. In a typical embodiment, a composition or immunogenic combination of the application comprising plasmid DNA can contain phosphate buffered saline (PBS) as the pharmaceutically acceptable carrier. The plasmid DNA can be present in a concentration of, e.g., 0.5 mg/mL to 5 mg/mL, such as 0.5 mg/mL 1, mg/mL, 2 mg/mL, 3 mg/mL, 4 mg/mL, or 5 mg/mL, preferably at 1 mg/mL.

Compositions and immunogenic combinations of the application can be formulated as a vaccine (also referred to as an "immunogenic composition") according to methods well known in the art. Such compositions can include adjuvants to enhance immune responses. The optimal ratios of each component in the formulation can be determined by techniques well known to those skilled in the art in view of the present disclosure.

In an embodiment of the application, an adjuvant is included in a composition or immunogenic combination of the application, or co-administered with a composition or immunogenic combination of the application. Use of an adjuvant is optional, and may further enhance immune responses when the composition is used for vaccination purposes. Adjuvants suitable for co-administration or inclusion in compositions in accordance with the application should preferably be ones that are potentially safe, well tolerated and effective in humans. An adjuvant can be a small molecule or antibody including, but not limited to, immune checkpoint inhibitors (e.g., anti-PD1, anti-RIM-3, etc.), toll-like receptor inhibitors, RIG-1 inhibitors, IL-15 superagonists (Altor Bioscience), mutant IRF3 and IRF7 genetic adjuvants, STING agonists (Aduro), FLT3L genetic adjuvant, IL-12 genetic adjuvant, and IL-7-hyFc.

Embodiments of the application also relate to methods of making compositions and immunogenic combinations of the application. According to embodiments of the application, a method of producing a composition or immunogenic combination comprises mixing an isolated polynucleotide encoding an HBV antigen, vector, and/or polypeptide of the application with one or more pharmaceutically acceptable carriers. One of ordinary skill in the art will be familiar with conventional techniques used to prepare such compositions.

Methods of Inducing/Enhancing an Immune Response

In another general aspect, the application relates to a method of inducing an immune response against hepatitis B virus (HBV) in a subject in need thereof, comprising administering to the subject an immunologically effective amount of a composition or immunogenic composition of the application. Any of the compositions and immunogenic combinations of the application described herein can be used in the methods of the application.

The application provides an improved method of priming and boosting an immune response to a HBV antigenic protein or immunogenic polypeptide thereof in a human subject using an MVA vector in combination with an adenoviral vector.

According to a general aspect of the application, a method of enhancing an immune response in a human subject comprises:
 a. administering to the human subject a first composition comprising an immunologically effective amount of an adenovirus vector of the application; and
 b. administering to the human subject a second composition comprising an immunologically effective amount of a MVA vector of the application;
 to thereby obtain an enhanced immune response against the HBV antigen in the human subject.

According to another general aspect of the application, a method of enhancing an immune response in a human subject comprises:
 a. administering to the human subject a first composition comprising an immunologically effective amount of a MVA vector of the application; and
 b. administering to the human subject a second composition comprising an immunologically effective amount of an adenovirus vector of the application;
 to thereby obtain an enhanced immune response against the HBV antigen in the human subject.

According to another general aspect of the application, a method of enhancing an immune response in a human subject comprises:
 a. administering to the human subject a first composition comprising an immunologically effective amount of a first plasmid comprising a first non-naturally occurring nucleic acid comprising a first polynucleotide sequence encoding an HBV pol antigen of the application, and an immunologically effective amount of a second plasmid comprising a second non-naturally occurring nucleic acid comprising a second polynucleotide sequence encoding a truncated HBV core antigen of the application; and b. administering to the human subject a second composition comprising an immunologically effective amount of a MVA vector of the application;

to thereby obtain an enhanced immune response against the HBV antigen in the human subject.

According to another general aspect of the application, a method of enhancing an immune response in a human subject comprises:

a. administering to the human subject a first composition comprising an immunologically effective amount of a MVA vector of the application; and b. administering to the human subject a second composition comprising an immunologically effective amount of a first plasmid comprising a first non-naturally occurring nucleic acid comprising a first polynucleotide sequence encoding an HBV pol antigen of the application, and an immunologically effective amount of a second plasmid comprising a second non-naturally occurring nucleic acid comprising a second polynucleotide sequence encoding a truncated HBV core antigen of the application;

to thereby obtain an enhanced immune response against the HBV antigen in the human subject.

The first composition is administered to the human subject in need thereof to prime the immune response, and the second composition is administered to the human subject in need thereof to boost the immune response. Priming and boosting the immune response can, for example, enhance the immune response.

According to embodiments of the application, the enhanced immune response comprises an enhanced antibody response against the HBV antigenic protein in the human subject.

Preferably, the enhanced immune response further comprises an enhanced CD4+ response or an enhanced CD8+ T cell response against the HBV antigenic protein in the human subject. The enhanced CD4+ T cell response generated by a method according to an embodiment of the application can be, for example, an increase or induction of a dominant CD4+ T cell response against the HBV antigenic protein, and/or an increase or induction of polyfunctional CD4+ T cells specific to the HBV antigenic protein in the human subject. The polyfunctional CD4+ T cells express more than one cytokine, such as two or more of IFN-gamma, IL-2 and TNF-alpha. The enhanced CD8+ T cell response generated by a method according to an embodiment of the application can be, for example, an increase or induction of polyfunctional CD8+ T cells specific to the HBV antigenic protein in the human subject.

More preferably, the enhanced immune response resulting from a method according to an embodiment of the application comprises an enhanced CD4+ T cell response, an enhanced antibody response and an enhanced CD8+ T cell response, against the HBV antigenic protein in the human subject.

As used herein, the term "infection" refers to the invasion of a host by a disease causing agent. A disease causing agent is considered to be "infectious" when it is capable of invading a host, and replicating or propagating within the host. Examples of infectious agents include viruses, e.g., HBV and certain species of adenovirus, prions, bacteria, fungi, protozoa and the like. "HBV infection" specifically refers to invasion of a host organism, such as cells and tissues of the host organism, by HBV.

According to embodiments of the application, "inducing an immune response" when used with reference to the methods described herein encompasses causing a desired immune response or effect in a subject in need thereof against HBV or an HBV infection. "Inducing an immune response" also encompasses providing a therapeutic immunity for treating against a pathogenic agent, i.e., HBV. As used herein, the term "therapeutic immunity" or "therapeutic immune response" means that the HBV-infected vaccinated subject is able to control an infection with the pathogenic agent, i.e., HBV, against which the vaccination was done. In one embodiment, "inducing an immune response" means producing an immunity in a subject in need thereof, e.g., to provide a therapeutic effect against a disease, such as HBV infection. In an embodiment of the application, "inducing an immune response" refers to causing or improving cellular immunity, e.g., T cell response, against HBV. In an embodiment of the application, "inducing an immune response" refers to causing or improving a humoral immune response against HBV. In an embodiment of the application, "inducing an immune response" refers to causing or improving a cellular and a humoral immune response against HBV.

Typically, the administration of compositions and immunogenic combinations according to embodiments of the application will have a therapeutic aim to generate an immune response against HBV after HBV infection or development of symptoms characteristic of HBV infection, i.e., for therapeutic vaccination.

As used herein, "an immunogenically effective amount" or "immunologically effective amount" means an amount of a composition, polynucleotide, vector, or antigen sufficient to induce a desired immune effect or immune response in a subject in need thereof. In one embodiment, an immunologically effective amount means an amount sufficient to induce an immune response in a subject in need thereof. In another embodiment, an immunologically effective amount means an amount sufficient to produce immunity in a subject in need thereof, e.g., provide a therapeutic effect against a disease such as HBV infection. An immunologically effective amount can vary depending upon a variety of factors, such as the physical condition of the subject, age, weight, health, etc.; the particular application, e.g., providing protective immunity or therapeutic immunity; and the particular disease, e.g., viral infection, for which immunity is desired. An immunologically effective amount can readily be determined by one of ordinary skill in the art in view of the present disclosure.

In particular embodiments of the application, an immunologically effective amount refers to the amount of a composition or immunogenic combination which is sufficient to achieve one, two, three, four, or more of the following effects: (i) reduce or ameliorate the severity of an HBV infection or a symptom associated therewith; (ii) reduce the duration of an HBV infection or symptom associated therewith; (iii) prevent the progression of an HBV infection or symptom associated therewith; (iv) cause regression of an HBV infection or symptom associated therewith; (v) prevent the development or onset of an HBV infection, or symptom associated therewith; (vi) prevent the recurrence of an HBV infection or symptom associated therewith; (vii) reduce hospitalization of a subject having an HBV infection; (viii) reduce hospitalization length of a subject having an HBV infection; (ix) increase the survival of a subject with an HBV infection; (x) eliminate an HBV infection in a subject; (xi) inhibit or reduce HBV replication in a subject; and/or (xii) enhance or improve the prophylactic or therapeutic effect(s) of another therapy.

In other particular embodiments, an immunologically effective amount is an amount sufficient to reduce HBsAg levels consistent with evolution to clinical seroconversion; achieve sustained HBsAg clearance associated with reduction of infected hepatocytes by a subject's immune system; induce HBV-antigen specific activated T-cell populations; and/or achieve persistent loss of HBsAg within 12 months. Examples of a target index include lower HBsAg below a threshold of 500 copies of HBsAg IU and/or higher CD8 counts.

As general guidance, an immunologically effective amount when used with reference to a viral vector can range from about $1\times10^7$ viral particles per dose to about $1\times10^{12}$ viral particles per dose. An immunologically effective amount can be about $1\times10^{10}$, about $2\times10^{10}$, about $3\times10^{10}$, about $4\times10^{10}$, about $5\times10^{10}$, about $6\times10^{10}$, about $7\times10^{10}$, about $8\times10^{10}$, about $9\times10^{10}$, about $1\times10^{11}$, about $2\times10^{11}$, about $3\times10^{11}$, about $4\times10^{11}$, about $5\times10^{11}$, or about $1\times10^{12}$ viral particles per dose. An immunologically effective amount can be from one vector or from multiple vectors. An immunologically effective amount can be administered in a single composition, or in multiple compositions, such as 1, 2, 3, 4, 5, 6, 7, 8, 9, or 10 compositions (e.g., tablets, capsules or injectables), wherein the administration of the multiple capsules or injections collectively provides a subject with an immunologically effective amount. It is also possible to administer an immunologically effective amount to a subject, and subsequently administer another dose of an immunologically effective amount to the same subject, in a so-called prime-boost regimen. This general concept of a prime-boost regimen is well known to the skilled person in the vaccine field. Further booster administrations can optionally be added to the regimen, as needed.

According to embodiments of the application, an immunogenic combination comprising two viral vectors, e.g., a first viral vector encoding an HBV core antigen and second viral vector encoding an HBV pol antigen can be administered to a subject by mixing both viral vectors and delivering the mixture to a single anatomic site. Alternatively, two separate immunizations each delivering a single expression vector can be performed. In such embodiments, whether both viral vectors are administered in a single immunization as a mixture of in two separate immunizations, the first viral vector and the second viral vector can be administered in a ratio of 10:1 to 1:10, by weight, such as 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, or 1:10, by weight. Preferably, the first and second viral vectors are administered in a ratio of 1:1, by weight.

In some embodiments, a subject to be treated according to the methods of the application is an HBV-infected subject, particular a subject having chronic HBV infection. Acute HBV infection is characterized by an efficient activation of the innate immune system complemented with a subsequent broad adaptive response (e.g., HBV-specific T-cells, neutralizing antibodies), which usually results in successful suppression of replication or removal of infected hepatocytes. In contrast, such responses are impaired or diminished due to high viral and antigen load, e.g., HBV envelope proteins are produced in abundance and can be released in sub-viral particles in 1,000-fold excess to infectious virus.

Chronic HBV infection is described in phases characterized by viral load, liver enzyme levels (necroinflammatory activity), HBeAg, or HBsAg load or presence of antibodies to these antigens. cccDNA levels stay relatively constant at approximately 10 to 50 copies per cell, even though viremia can vary considerably. The persistence of the cccDNA species leads to chronicity. More specifically, the phases of chronic HBV infection include: (i) the immune-tolerant phase characterized by high viral load and normal or minimally elevated liver enzymes; (ii) the immune activation HBeAg-positive phase in which lower or declining levels of viral replication with significantly elevated liver enzymes are observed; (iii) the inactive HBsAg carrier phase, which is a low replicative state with low viral loads and normal liver enzyme levels in the serum that may follow HBeAg seroconversion; and (iv) the HBeAg-negative phase in which viral replication occurs periodically (reactivation) with concomitant fluctuations in liver enzyme levels, mutations in the pre-core and/or basal core promoter are common, such that HBeAg is not produced by the infected cell.

As used herein, "chronic HBV infection" refers to a subject having the detectable presence of HBV for more than 6 months. A subject having a chronic HBV infection can be in any phase of chronic HBV infection. In preferred embodiments, a chronic HBV infection referred to herein follows the definition published by the Centers for Disease Control and Prevention (CDC), according to which a chronic HBV infection is characterized by the following laboratory criteria: (i) negative for IgM antibodies to hepatitis B core antigen (IgM anti-HBc) and positive for hepatitis B surface antigen (HBsAg), hepatitis B e antigen (HBeAg), or nucleic acid test for hepatitis B virus DNA, or (ii) positive for HBsAg or nucleic acid test for HBV DNA, or positive for HBeAg two times at least 6 months apart.

According to particular embodiments, an immunogenically effective amount refers to the amount of a composition or immunogenic combination which is sufficient to treat chronic HBV infection.

In some embodiments, a subject having chronic HBV infection is undergoing nucleoside analog (NUC) treatment, and is NUC-suppressed. As used herein, "NUC-suppressed" refers to a subject having an undetectable viral level of HBV and stable alanine aminotransferase (ALT) levels for at least six months. Examples of nucleoside/nucleotide analog treatment include HBV polymerase inhibitors, such as entacavir and tenofovir. Preferably, a subject having chronic HBV infection does not have advanced hepatic fibrosis or cirrhosis. Such subject would typically have a METAVIR score of less than 3 and a fibroscan result of less than 9 kPa. The METAVIR score is a scoring system that is commonly used to assess the extent of inflammation and fibrosis by histopathological evaluation in a liver biopsy of patients with hepatitis B. The scoring system assigns two standardized numbers: one reflecting the degree of inflammation and one reflecting the degree of fibrosis.

It is believed that elimination or reduction of chronic HBV may allow early disease interception of severe liver disease, including virus-induced cirrhosis and hepatocellular carcinoma. Thus, the methods of the application can also be used as therapy to treat HBV-induced diseases. Examples of HBV-induced diseases include, but are not limited to cirrhosis, cancer (e.g., hepatocellular carcinoma), and fibrosis, particularly advanced fibrosis characterized by a METAVIR score of 3 or higher. In such embodiments, an immunogenically effective amount is an amount sufficient to achieve persistent loss of HBsAg within 12 months and significant decrease in clinical disease (e.g., cirrhosis, hepatocellular carcinoma, etc.).

Methods according to embodiments of the application further comprise administering to the subject in need thereof another immunogenic agent (such as another HBV antigen or other antigen) or another anti-HBV agent (such as a nucleoside analog or other anti-HBV agent) in combination with a composition of the application.

Methods of Delivery

Compositions and immunogenic combinations of the application can be administered to a subject by any method known in the art in view of the present disclosure, including, but not limited to, parenteral administration (e.g., intramuscular, subcutaneous, intravenous, or intradermal injection), oral administration, transdermal administration, and nasal administration. Preferably, compositions and immunogenic combinations are administered parenterally (e.g., by intramuscular injection or intradermal injection) or transdermally.

In some embodiments of the application in which a composition or immunogenic combination comprises one or more viral vectors, administration can be by injection through the skin, e.g., intramuscular or intradermal injection, preferably intramuscular injection. Intramuscular injection can be combined with electroporation, i.e., application of an electric field to facilitate delivery of the DNA plasmids to cells. As used herein, the term "electroporation" refers to the use of a transmembrane electric field pulse to induce microscopic pathways (pores) in a bio-membrane. During in vivo electroporation, electrical fields of appropriate magnitude and duration are applied to cells, inducing a transient state of enhanced cell membrane permeability, thus enabling the cellular uptake of molecules unable to cross cell membranes on their own. Creation of such pores by electroporation facilitates passage of biomolecules, such as plasmids, oligonucleotides, siRNAs, drugs, etc., from one side of a cellular membrane to the other. In vivo electroporation for the delivery of DNA vaccines has been shown to significantly increase plasmid uptake by host cells, while also leading to mild-to-moderate inflammation at the injection site. As a result, transfection efficiency and immune response are significantly improved (e.g., up to 1,000 fold and 100 fold respectively) with intradermal or intramuscular electroporation, in comparison to conventional injection.

In a typical embodiment, electroporation is combined with intramuscular injection. However, it is also possible to combine electroporation with other forms of parenteral administration, e.g., intradermal injection, subcutaneous injection, etc.

Administration of a composition, immunogenic combination or vaccine of the application via electroporation can be accomplished using electroporation devices that can be configured to deliver to a desired tissue of a mammal a pulse of energy effective to cause reversible pores to form in cell membranes. The electroporation device can include an electroporation component and an electrode assembly or handle assembly. The electroporation component can include one or more of the following components of electroporation devices: controller, current waveform generator, impedance tester, waveform logger, input element, status reporting element, communication port, memory component, power source, and power switch. Electroporation can be accomplished using an in vivo electroporation device. Examples of electroporation devices and electroporation methods that can facilitate delivery of compositions and immunogenic combinations of the application, particularly those comprising DNA plasmids, include CELLECTRA® (Inovio Pharmaceuticals, Blue Bell, Pa.), Elgen electroporator (Inovio Pharmaceuticals, Inc.) Tri-Grid™ delivery system (Ichor Medical Systems, Inc., San Diego, Calif. 92121) and those described in U.S. Pat. Nos. 7,664,545, 8,209,006, 9,452,285, 5,273,525, 6,110,161, 6,261,281, 6,958,060, and 6,939,862, 7,328,064, 6,041,252, 5,873,849, 6,278,895, 6,319,901, 6,912,417, 8,187,249, 9,364,664, 9,802,035, 6,117,660, and International Patent Application Publication WO2017172838, all of which are herein incorporated by reference in their entireties. Also contemplated by the application for delivery of the compositions and immunogenic combinations of the application are use of a pulsed electric field, for instance as described in, e.g., U.S. Pat. No. 6,697,669, which is herein incorporated by reference in its entirety.

In other embodiments of the application in which a composition or immunogenic combination comprises one or more DNA plasmids, the method of administration is transdermal. Transdermal administration can be combined with epidermal skin abrasion to facilitate delivery of the DNA plasmids to cells. For example, a dermatological patch can be used for epidermal skin abrasion. Upon removal of the dermatological patch, the composition or immunogenic combination can be deposited on the abraised skin.

Methods of delivery are not limited to the above described embodiments, and any means for intracellular delivery can be used. Other methods of intracellular delivery contemplated by the methods of the application include, but are not limited to, liposome encapsulation, nanoparticles, etc.

Adjuvants

In some embodiments of the application, a method of inducing an immune response against HBV further comprises administering an adjuvant. The terms "adjuvant" and "immune stimulant" are used interchangeably herein, and are defined as one or more substances that cause stimulation of the immune system. In this context, an adjuvant is used to enhance an immune response to HBV antigens and antigenic HBV polypeptides of the application.

According to embodiments of the application, an adjuvant can be present in an immunogenic combination or composition of the application, or administered in a separate composition. An adjuvant can be, e.g., a small molecule or an antibody. Examples of adjuvants suitable for use in the application include, but are not limited to, immune checkpoint inhibitors (e.g., anti-PD1, anti-RIM-3, etc.), toll-like receptor inhibitors, RIG-1 inhibitors, IL-15 superagonists (Altor Bioscience), mutant IRF3 and IRF7 genetic adjuvants, STING agonists (Aduro), FLT3L genetic adjuvant, IL-12 genetic adjuvant, and IL-7-hyFc.

Compositions and immunogenic combinations of the application can also be administered in combination with at least one other anti-HBV agent. Examples of anti-HBV agents suitable for use with the application include, but are not limited to small molecules, antibodies, and/or CAR-T therapies that function as capsid inhibitors, TLR inhibitors, cccDNA inhibitors, HBV polymerase inhibitors (e.g., entecavir and tenofovir), and/or immune checkpoint inhibitors, etc. Such anti-HBV agents can be administered with the compositions and immunogenic combinations of the application simultaneously or sequentially.

Methods of Prime/Boost Immunization

Embodiments of the application also contemplate administering an immunologically effective amount of a composition or immunogenic combination to a subject, and subsequently administering another dose of an immunologically effective amount of a composition or immunogenic combination to the same subject, in a so-called prime-boost regimen Thus, in one embodiment, a composition or immunogenic combination of the application is a primer vaccine used for priming an immune response. In another embodiment, a composition or immunogenic combination of the application is a booster vaccine used for boosting an immune response. The priming and boosting vaccines according to embodiments of the application can be used in the methods of the application described herein. This general concept of a prime-boost regimen is well known to the skilled person in the vaccine field. Any of the compositions and immunogenic combinations of the application described herein can be used as priming and/or boosting vaccines for priming and/or boosting an immune response against HBV.

According to embodiments of the application, a composition or immunogenic combination of the application can be administered at least once for priming immunization. The composition or immunogenic combination can be re-administered for boosting immunization. Further booster administrations of the composition or vaccine combination can optionally be added to the regimen, as needed. An adjuvant can be present in a composition of the application used for boosting immunization, present in a separate composition to be administered together with the composition or immunogenic combination of the application for the boosting immunization, or administered on its own as the boosting immunization. In those embodiments in which an adjuvant is included in the regimen, the adjuvant is preferably used for boosting immunization.

An illustrative and non-limiting example of a prime-boost regimen includes administering a single dose of an immunologically effective amount of a composition or immunogenic combination of the application to a subject to prime the immune response; and subsequently administering another dose of an immunologically effective amount of a composition or immunogenic combination of the application to boost the immune response, wherein the boosting immunization is first administered about one to twelve weeks (1 to 12), about two to twelve weeks (2 to 12), about two to ten weeks (2 to 10), about two to six weeks (2 to 6), preferably about four weeks after the priming immunization is initially administered, preferably about eight weeks after the priming immunization is initially administered. In an embodiment of the application, the boosting immunization is administered at least one week after the priming immunization. In an embodiment of the application, the boosting immunization is administered at least two weeks after the priming immunization. Optionally, about 10 to 14 weeks, preferably 12 weeks, after the priming immunization is initially administered, a further boosting immunization of the composition or immunogenic combination, or other adjuvant, is administered.

Kits

The application also provides a kit comprising an immunogenic combination of the application. A kit can comprise the first polynucleotide and the second polynucleotide in separate compositions, or a kit can comprise the first polynucleotide and the second polynucleotide in a single composition. A kit can further comprise one or more adjuvants or immune stimulants, and/or other anti-HBV agents.

The ability to induce or stimulate an anti-HBV immune response upon administration in an animal or human organism can be evaluated either in vitro or in vivo using a variety of assays which are standard in the art. For a general description of techniques available to evaluate the onset and activation of an immune response, see for example Coligan et al. (1992 and 1994, Current Protocols in Immunology; ed. J Wiley & Sons Inc, National Institute of Health). Measurement of cellular immunity can be performed by measurement of cytokine profiles secreted by activated effector cells including those derived from CD4+ and CD8+ T-cells (e.g. quantification of IL-10 or IFN gamma-producing cells by ELISPOT), by determination of the activation status of immune effector cells (e.g. T cell proliferation assays by a classical [3H] thymidine uptake), by assaying for antigen-specific T lymphocytes in a sensitized subject (e.g. peptide-specific lysis in a cytotoxicity assay, etc.).

The ability to stimulate a cellular and/or a humoral response can be determined by antibody binding and/or competition in binding (see for example Harlow, 1989, Antibodies, Cold Spring Harbor Press). For example, titers of antibodies produced in response to administration of a composition providing an immunogen can be measured by enzyme-linked immunosorbent assay (ELISA). The immune responses can also be measured by neutralizing antibody assay, where a neutralization of a virus is defined as the loss of infectivity through reaction/inhibition/neutralization of the virus with specific antibody. The immune response can further be measured by Antibody-Dependent Cellular Phagocytosis (ADCP) Assay.

EMBODIMENTS

The i application provides also the following non-limiting embodiments.

Embodiment 1 is a Modified Vaccinia Ankara (MVA) vector comprising a non-naturally occurring nucleic acid molecule comprising a first polynucleotide sequence encoding an HBV polymerase antigen comprising an amino acid sequence that is at least 98% identical to SEQ ID NO:4.

Embodiment 2 is the MVA vector of embodiment 1, wherein the HBV polymerase antigen does not have reverse transcriptase activity and RNase H activity.

Embodiment 3 is the MVA vector of embodiment 1 or 2, wherein the HBV polymerase antigen is capable of inducing an immune response in a mammal against at least two HBV genotypes, preferably the HBV polymerase antigen is capable of inducing a T cell response in a mammal against at least HBV genotypes B, C, and D, and more preferably the HBV polymerase antigen is capable of inducing a CD8 T cell response in a human subject against at least HBV genotypes A, B, C, and D.

Embodiment 4 is the MVA vector of any one of embodiments 1-3, wherein the HBV polymerase antigen comprises the amino acid sequence of SEQ ID NO: 4.

Embodiment 5 is the MVA vector of any one of embodiments 1-4, further comprising a polynucleotide sequence encoding a signal sequence operably linked to the HBV polymerase antigen.

Embodiment 6 is the MVA vector of embodiment 5, wherein the signal sequence comprises the amino acid sequence of SEQ ID NO: 6 or SEQ ID NO: 11, preferably the signal sequence is encoded by the polynucleotide sequence of SEQ ID NO: 5 or SEQ ID NO: 10.

Embodiment 7 is the MVA vector of any one of embodiments 1-6, wherein the first polynucleotide sequence is at least 90% identical to SEQ ID NO: 3.

Embodiment 8 is the MVA vector of embodiment 7, wherein the first polynucleotide sequence comprises the polynucleotide sequence of SEQ ID NO: 3.

Embodiment 9 is the MVA vector of any one of embodiments 1-8, further comprising a second polynucleotide sequence encoding a truncated HBV core antigen consisting of the amino acid sequence of SEQ ID NO: 2.

Embodiment 10 is the MVA vector of embodiment 9, wherein the second polynucleotide sequence is at least 90% identical to SEQ ID NO: 1.

Embodiment 11 is the MVA vector of embodiment 10, wherein the second polynucleotide sequence comprises the polynucleotide sequence of SEQ ID NO: 1.

Embodiment 12 is the MVA vector of any one of embodiments 9-11, wherein the second polynucleotide sequence further comprises a polynucleotide sequence encoding a signal sequence operably linked to the truncated HBV core antigen.

Embodiment 13 is the MVA vector of embodiment 12, wherein the signal sequence comprises the amino acid sequence of SEQ ID NO: 6 or SEQ ID NO: 11, preferably the signal sequence is encoded by the polynucleotide sequence of SEQ ID NO: or SEQ ID NO: 10.

Embodiment 14 is the MVA vector of any one of embodiments 9-13, wherein the first and second polynucleotide sequences encode a fusion protein comprising the truncated HBV core antigen operably linked to the HBV polymerase antigen.

Embodiment 15 is the MVA vector of embodiment 14, wherein the fusion protein comprises the truncated HBV core antigen operably linked to the HBV polymerase antigen via a linker.

Embodiment 16 is the MVA vector of embodiment 15, wherein the linker comprises the amino acid sequence of (AlaGly)n, and n is an integer of 2 to 5, preferably the linker is encoded by a polynucleotide sequence comprising SEQ ID NO: 14.

Embodiment 17 is the MVA vector of embodiment 16, wherein the fusion protein comprises the amino acid sequence of SEQ ID NO: 12.

Embodiment 18 is the MVA vector of any one of embodiments 14-17, wherein the fusion protein further comprises a signal sequence, preferably the signal sequence comprises the amino acid sequence of SEQ ID NO: 6 or SEQ ID NO: 11, more preferably the signal sequence is encoded by the polynucleotide sequence of SEQ ID NO: 5 or SEQ ID NO: 10.

Embodiment 19 is the MVA vector of any one of embodiments 1-18 further comprising at least one promoter sequence, optionally one or more additional regulatory sequences, preferably the at least one promoter sequence comprises the polynucleotide sequence of SEQ ID NO: 25 and/or SEQ ID NO: 26, and the additional regulatory sequence is selected from the group consisting of an enhancer sequence of SEQ ID NO: 8 or SEQ ID NO: 15, and a polyadenylation signal sequence of SEQ ID NO: 9 or SEQ ID NO: 16.

Embodiment 20 is the MVA vector of any one of embodiments 1-19, wherein the non-naturally occurring nucleic acid molecule does not encode a HBV antigen selected from the group consisting of a Hepatitis B surface antigen (HBsAg), a HBV envelope (Env) antigen, and a HBV L protein antigen.

Embodiment 21 is an MVA vector comprising a first non-naturally occurring nucleic acid molecule comprising a first polynucleotide sequence encoding an HBV polymerase antigen comprising the amino acid sequence of SEQ ID NO: 4, wherein the first polynucleotide sequence further encodes a signal sequence comprising the amino acid sequence of SEQ ID NO: 6, and wherein the first polynucleotide sequence further comprises a promoter sequence comprising the polynucleotide sequence of SEQ ID NO: 26, and a second non-naturally occurring nucleic acid molecule comprising a second polynucleotide sequence encoding a truncated HBV core antigen consisting of the amino acid sequence of SEQ ID NO: 2, wherein the second polynucleotide sequence further encodes a signal sequence comprising the amino acid sequence of SEQ ID NO: 11, and wherein the second polynucleotide sequence further comprises a promoter sequence comprising the polynucleotide sequence of SEQ ID NO: 25.

Embodiment 22 is a composition comprising the MVA vector of any one of embodiments 1-21 and a pharmaceutically acceptable carrier.

Embodiment 23 is a method of enhancing an immune response in a human subject, the method comprising (a) administering to the human subject a first composition comprising an immunologically effective amount of an adenovirus vector comprising a non-naturally occurring nucleic acid molecule comprising a first polynucleotide sequence encoding an HBV polymerase antigen comprising an amino acid sequence that is at least 98% identical to SEQ ID NO:4; and (b) administering to the human subject a second composition comprising an immunologically effective amount of the MVA vector of any one of embodiments 1-21; to thereby obtain an enhanced immune response against the HBV antigen in the human subject.

Embodiment 24 is the method of embodiment 23, wherein the HBV polymerase antigen of the first composition does not have reverse transcriptase activity and RNase H activity.

Embodiment 25 is the method of embodiment 23 or 24, wherein the first composition is for priming the immune response and the second composition is for boosting the immune response.

Embodiment 26 is the method of any one of embodiments 23-25, wherein the HBV polymerase antigen of the first composition is capable of inducing an immune response in the human subject against at least two HBV genotypes, preferably the HBV polymerase antigen is capable of inducing a T cell response in the human subject against at least HBV genotypes B, C, and D, and more preferably the HBV polymerase antigen is capable of inducing a CD8 T cell response in the human subject against at least HBV genotypes A, B, C, and D.

Embodiment 27 is the method of any one of embodiments 23-26, wherein the HBV polymerase antigen of the first composition comprises the amino acid sequence of SEQ ID NO: 4.

Embodiment 28 is the method of any one of embodiments 23-27, further comprising a polynucleotide sequence encoding a signal sequence operably linked to the HBV polymerase antigen of the first composition.

Embodiment 29 is the method of embodiment 28, wherein the signal sequence comprises the amino acid sequence of SEQ ID NO: 6 or SEQ ID NO: 11, preferably the signal sequence is encoded by the polynucleotide sequence of SEQ ID NO: 5 or SEQ ID NO: 10.

Embodiment 30 is the method of any one of embodiments 23-29, wherein the first polynucleotide sequence of the first composition is at least 90% identical to SEQ ID NO: 19.

Embodiment 31 is the method of embodiment 30, wherein the first polynucleotide sequence of the first composition comprises the polynucleotide sequence of SEQ ID NO: 19.

Embodiment 32 is the method of any one of embodiments 23-31, wherein the nucleic acid molecule of the adenovirus in the first composition further comprises a second polynucleotide sequence encoding a truncated HBV core antigen consisting of the amino acid sequence of SEQ ID NO: 2.

Embodiment 33 is the method of embodiment 32, wherein the second polynucleotide sequence of the first composition is at least 90% identical to SEQ ID NO: 17.

Embodiment 34 is the method of embodiment 33, wherein the second polynucleotide sequence of the first composition comprises the polynucleotide sequence of SEQ ID NO: 17.

Embodiment 35 is the method of any one of embodiments 32-34, wherein the first and second polynucleotide sequences of the first composition encode a fusion protein comprising the truncated HBV core antigen operably linked to the HBV polymerase antigen.

Embodiment 36 is the method of embodiment 35, wherein the fusion protein of the first composition comprises the truncated HBV core antigen operably linked to the HBV polymerase antigen via a linker.

Embodiment 37 is the method of embodiment 36, wherein the linker of the first composition comprises the amino acid sequence of (AlaGly)n, and n is an integer of 2 to 5, preferably the linker is encoded by a polynucleotide sequence comprising SEQ ID NO: 14.

Embodiment 38 is the method of embodiment 37, wherein the fusion protein of the first composition comprises the amino acid sequence of SEQ ID NO: 12.

Embodiment 39 is the method of any one of embodiments 35-38, wherein the fusion protein of the first composition further comprises a signal sequence, preferably the signal sequence comprises the amino acid sequence of SEQ ID NO: 6 or SEQ ID NO: 11, more preferably the signal sequence is encoded by the polynucleotide sequence of SEQ ID NO: 5 or SEQ ID NO: 10.

Embodiment 40 is the method of any one of embodiments 23-39, wherein the non-naturally occurring nucleic acid molecule of the first composition further comprises a promoter sequence, optionally one or more additional regulatory sequences, preferably the promoter sequence comprises the polynucleotide sequence of SEQ ID NO: 7, and the additional regulatory sequence is selected from the group consisting of an enhancer sequences of SEQ ID NO: 8 or SEQ ID NO: 15, and a polyadenylation signal sequence of SEQ ID NO: 16.

Embodiment 41 is the method of any one of embodiments 23-40, wherein the non-naturally occurring nucleic acid molecule of the first composition does not encode a HBV antigen selected from the group consisting of a Hepatitis B surface antigen (HBsAg), a HBV envelope (Env) antigen, and a HBV L protein antigen.

Embodiment 42 is the method of any one of claims 23-41, wherein the enhanced immune response comprises an enhanced antibody response against the HBV antigen in the human subject.

Embodiment 43 is the method of embodiment 42, wherein the enhanced immune response comprises an enhanced CD8+ T cell response against the HBV antigen in the human subject.

Embodiment 44 is the method of embodiment 42 or 43, wherein the enhanced immune response comprises an enhanced CD4+ T cell response against the HBV antigen in the human subject.

Embodiment 45 is the method of any one of embodiments 23-44, wherein the adenovirus vector is an rAd26 or rAd35 vector.

Embodiment 46 is the method of any one of embodiments 23-45, wherein step (b) is conducted 1-12 weeks after step (a).

Embodiment 47 is the method of any one of embodiments 23-45, wherein step (b) is conducted 2-12 weeks after step (a).

Embodiment 48 is the method of any one of embodiments 23-45, wherein step (b) is conducted at least 1 week after step (a).

Embodiment 49 is the method of any one of embodiments 23-45, wherein step (b) is conducted at least 2 weeks after step (a).

Embodiment 50 is a vaccine combination comprising (a) a first composition comprising an immunologically effective amount of an adenovirus vector comprising a first polynucleotide sequence encoding an HBV polymerase antigen comprising an amino acid sequence that is at least 98% identical to SEQ ID NO:4; and (b) a second composition comprising an immunologically effective amount of a Modified Vaccinia Ankara (MVA) vector comprising a second polynucleotide sequence encoding an HBV polymerase antigen comprising an amino acid sequence that is at least 98% identical to SEQ ID NO: 4; wherein the first composition is administered to the human subject for priming the immune response, and the second composition is administered to the human subject one or more times for boosting the immune response.

Embodiment 51 is the vaccine combination of embodiment 50, wherein the HBV polymerase antigen of the first and second composition does not have reverse transcriptase activity and RNase H activity.

Embodiment 52 is the vaccine combination of embodiment 50 or 51, wherein the HBV polymerase antigen of the first and second composition is capable of inducing an immune response in a mammal against at least two HBV genotypes, preferably the HBV polymerase antigen is capable of inducing a T cell response in a mammal against at least HBV genotypes B, C, and D, and more preferably the HBV polymerase antigen is capable of inducing a CD8 T cell response in a human subject against at least HBV genotypes A, B, C, and D.

Embodiment 53 is the vaccine combination of any one of embodiments 50-52, wherein the HBV polymerase antigen of the first and second composition comprises the amino acid sequence of SEQ ID NO: 4.

Embodiment 54 is the vaccine combination of any one of embodiments 50-53, further comprising a polynucleotide sequence encoding a signal sequence operably linked to the HBV polymerase antigen of the first and second composition.

Embodiment 55 is the vaccine combination of embodiment 54, wherein the signal sequence comprises the amino acid sequence of SEQ ID NO: 6 or SEQ ID NO: 11, preferably the signal sequence is encoded by the polynucleotide sequence of SEQ ID NO: 5 or SEQ ID NO: 10.

Embodiment 56 is the vaccine combination of any one of embodiments 50-55, wherein the first and second polynucleotide sequence is at least 90% identical to SEQ ID NO: 3.

Embodiment 57 is the vaccine combination of embodiment 56, wherein the first and second polynucleotide sequence comprises the polynucleotide sequence of SEQ ID NO: 3.

Embodiment 58 is the vaccine combination of any one of embodiments 50-57, wherein the adenovirus vector of the first composition further comprises a third polynucleotide sequence and the MVA vector of the second composition further comprises a fourth polynucleotide sequence, wherein the third and fourth polynucleotide sequence encode a truncated HBV core antigen consisting of the amino acid sequence of SEQ ID NO: 2.

Embodiment 59 is the vaccine combination of embodiment 58, wherein the third and fourth polynucleotide sequence is at least 90% identical to SEQ ID NO: 1.

Embodiment 60 is the vaccine combination of embodiment 59, wherein the third and fourth polynucleotide sequence comprises the polynucleotide sequence of SEQ ID NO: 1.

Embodiment 61 is a vaccine combination comprising (a) a first composition comprising an immunologically effective amount of a Modified Vaccinia Ankara (MVA) vector comprising a first polynucleotide sequence encoding an HBV polymerase antigen comprising an amino acid sequence that is at least 98% identical to SEQ ID NO:4; and (b) a second composition comprising an immunologically effective amount of an adenovirus vector comprising a second polynucleotide sequence encoding an HBV polymerase antigen comprising an amino acid sequence that is at least 98% identical to SEQ ID NO:4; wherein the first composition is administered to the human subject for priming the immune response, and the second composition is administered to the human subject one or more times for boosting the immune response.

Embodiment 62 is the vaccine combination of embodiment 61, wherein the HBV polymerase antigen of the first and second composition does not have reverse transcriptase activity and RNase H activity.

Embodiment 63 is the vaccine combination of embodiment 61 or 62, wherein the HBV polymerase antigen of the first and second composition is capable of inducing an immune response in a mammal against at least two HBV genotypes, preferably the HBV polymerase antigen is capable of inducing a T cell response in a mammal against at least HBV genotypes B, C, and D, and more preferably the HBV polymerase antigen is capable of inducing a CD8 T cell response in a human subject against at least HBV genotypes A, B, C, and D.

Embodiment 64 is the vaccine combination of any one of embodiments 61-63, wherein the HBV polymerase antigen of the first and second composition comprises the amino acid sequence of SEQ ID NO: 4.

Embodiment 65 is the vaccine combination of any one of embodiments 61-64, further comprising a polynucleotide sequence encoding a signal sequence operably linked to the HBV polymerase antigen of the first and second composition.

Embodiment 66 is the vaccine combination of embodiment 65, wherein the signal sequence comprises the amino acid sequence of SEQ ID NO: 6 or SEQ ID NO: 11, preferably the signal sequence is encoded by the polynucleotide sequence of SEQ ID NO: or SEQ ID NO: 10.

Embodiment 67 is the vaccine combination of any one of embodiments 61-66, wherein the first and second polynucleotide sequence is at least 90% identical to SEQ ID NO: 3.

Embodiment 68 is the vaccine combination of embodiment 67, wherein the first and second polynucleotide sequence comprises the polynucleotide sequence of SEQ ID NO: 3.

Embodiment 69 is the vaccine combination of any one of embodiments 61-68, wherein the MVA vector of the first composition further comprises a third polynucleotide sequence and the adenovirus vector of the second composition further comprises a fourth polynucleotide sequence, wherein the third and fourth polynucleotide sequence encode a truncated HBV core antigen consisting of the amino acid sequence of SEQ ID NO: 2.

Embodiment 70 is the vaccine combination of embodiment 69, wherein the third and fourth polynucleotide sequence is at least 90% identical to SEQ ID NO: 1.

Embodiment 71 is the vaccine combination of embodiment 70, wherein the third and fourth polynucleotide sequence comprises the polynucleotide sequence of SEQ ID NO: 1.

Embodiment 72 is the vaccine combination of any one of embodiments 50-71, which is a kit.

Embodiment 73 is a method of enhancing an immune response in a human subject, the method comprising (a) administering to the human subject a first composition comprising an immunologically effective amount of a first plasmid comprising a first non-naturally occurring nucleic acid molecule comprising a first polynucleotide sequence encoding an HBV polymerase antigen comprising an amino acid sequence that is at least 98% identical to SEQ ID NO: 4 and a second plasmid comprising a second non-naturally occurring nucleic acid molecule comprising a second polynucleotide sequence encoding a truncated HBV core antigen consisting of the amino acid sequence of SEQ ID NO: 2; and (b) administering to the human subject a second composition comprising an immunologically effective amount of the MVA vector of any one of embodiments 1-21; to thereby obtain an enhanced immune response against the HBV antigen in the human subject.

Embodiment 74 is the method of embodiment 73, wherein the HBV polymerase antigen of the first composition does not have reverse transcriptase activity and RNase H activity.

Embodiment 75 is the method of embodiment 73 or 74, wherein the first composition is for priming the immune response and the second composition is for boosting the immune response.

Embodiment 76 is the method of any one of embodiments 73-75, wherein the HBV polymerase antigen of the first composition is capable of inducing an immune response in the human subject against at least two HBV genotypes, preferably the HBV polymerase antigen is capable of inducing a T cell response in the human subject against at least HBV genotypes B, C, and D, and more preferably the HBV polymerase antigen is capable of inducing a CD8 T cell response in the human subject against at least HBV genotypes A, B, C, and D.

Embodiment 77 is the method of any one of embodiments 73-76, wherein the HBV polymerase antigen of the first composition comprises the amino acid sequence of SEQ ID NO: 4.

Embodiment 78 is the method of any one of embodiments 73-77, further comprising a polynucleotide sequence encoding a signal sequence operably linked to the HBV polymerase antigen of the first composition.

Embodiment 79 is the method of embodiment 78, wherein the signal sequence comprises the amino acid sequence of SEQ ID NO: 6 or SEQ ID NO: 11, preferably the signal sequence is encoded by the polynucleotide sequence of SEQ ID NO: 5 or SEQ ID NO: 10.

Embodiment 80 is the method of any one of embodiments 73-79, wherein the first polynucleotide sequence of the first composition is at least 90% identical to SEQ ID NO: 20.

Embodiment 81 is the method of embodiment 80, wherein the first polynucleotide sequence of the first composition comprises the polynucleotide sequence of SEQ ID NO: 20.

Embodiment 82 is the method of embodiments 73-81, wherein the second polynucleotide sequence of the first composition is at least 90% identical to SEQ ID NO: 18.

Embodiment 83 is the method of embodiment 82, wherein the second polynucleotide sequence of the first composition comprises the polynucleotide sequence of SEQ ID NO: 18.

Embodiment 84 is the method of any one of embodiments 73-83, wherein the first and second polynucleotide sequences of the first composition further comprise a promoter sequence, optionally one or more additional regulatory sequences, preferably the promoter sequence comprises the polynucleotide sequence of SEQ ID NO: 7, and the additional regulatory sequence is selected from the group consisting of an enhancer sequence of SEQ ID NO: 8 or SEQ ID NO: 15, and a polyadenylation signal sequence of SEQ ID NO: 16.

Embodiment 85 is the method of any one of claims 73-84, wherein the enhanced immune response comprises an enhanced antibody response against the HBV antigen in the human subject.

Embodiment 86 is the method of embodiment 85, wherein the enhanced immune response comprises an enhanced CD8+ T cell response against the HBV antigen in the human subject.

Embodiment 87 is the method of embodiment 85 or 86, wherein the enhanced immune response comprises an enhanced CD4+ T cell response against the HBV antigen in the human subject.

Embodiment 88 is the method of any one of embodiments 73-87, wherein step (b) is conducted 1-12 weeks after step (a).

Embodiment 89 is the method of any one of embodiments 73-87, wherein step (b) is conducted 2-12 weeks after step (a).

Embodiment 90 is the method of any one of embodiments 73-87, wherein step (b) is conducted at least 1 week after step (a).

Embodiment 91 is the method of any one of embodiments 73-87, wherein step (b) is conducted at least 2 weeks after step (a).

Embodiment 92 is a method of enhancing an immune response in a human subject, the method comprising (a) administering to the human subject a first composition comprising an immunologically effective amount of the MVA vector of any one of embodiments 1-21; and (b) administering to the human subject a second composition comprising an immunologically effective amount of a first plasmid comprising a non-naturally occurring nucleic acid molecule comprising a first polynucleotide sequence encoding an HBV polymerase antigen comprising an amino acid sequence that is at least 98% identical to SEQ ID NO: 4 and a second plasmid comprising a non-naturally occurring nucleic acid molecule comprising a second polynucleotide sequence encoding a truncated HBV core antigen consisting of the amino acid sequence of SEQ ID NO: 2; to thereby obtain an enhanced immune response against the HBV antigen in the human subject.

Embodiment 93 is the method of embodiment 92, wherein the HBV polymerase antigen of the second composition does not have reverse transcriptase activity and RNase H activity.

Embodiment 94 is the method of embodiment 92 or 93, wherein the first composition is for priming the immune response and the second composition is for boosting the immune response.

Embodiment 95 is the method of any one of embodiments 92-94, wherein the HBV polymerase antigen of the second composition is capable of inducing an immune response in the human subject against at least two HBV genotypes, preferably the HBV polymerase antigen is capable of inducing a T cell response in the human subject against at least HBV genotypes B, C, and D, and more preferably the HBV polymerase antigen is capable of inducing a CD8 T cell response in the human subject against at least HBV genotypes A, B, C, and D.

Embodiment 96 is the method of any one of embodiments 92-95, wherein the HBV polymerase antigen of the second composition comprises the amino acid sequence of SEQ ID NO: 4.

Embodiment 97 is the method of any one of embodiments 92-96, further comprising a polynucleotide sequence encoding a signal sequence operably linked to the HBV polymerase antigen of the second composition.

Embodiment 98 is the method of embodiment 97, wherein the signal sequence comprises the amino acid sequence of SEQ ID NO: 6 or SEQ ID NO: 11, preferably the signal sequence is encoded by the polynucleotide sequence of SEQ ID NO: 5 or SEQ ID NO: 10.

Embodiment 99 is the method of any one of embodiments 92-98, wherein the first polynucleotide sequence of the second composition is at least 90% identical to SEQ ID NO: 20.

Embodiment 100 is the method of embodiment 99, wherein the first polynucleotide sequence of the second composition comprises the polynucleotide sequence of SEQ ID NO: 20.

Embodiment 101 is the method of embodiments 92-100, wherein the second polynucleotide sequence of the second composition is at least 90% identical to SEQ ID NO: 18.

Embodiment 102 is the method of embodiment 101, wherein the second polynucleotide sequence of the second composition comprises the polynucleotide sequence of SEQ ID NO: 18.

Embodiment 103 is the method of any one of embodiments 92-102, wherein the first and second polynucleotide sequences of the second composition further comprise a promoter sequence, optionally one or more additional regulatory sequences, preferably the promoter sequence comprises the polynucleotide sequence of SEQ ID NO:7, and the additional regulatory sequence is selected from the group consisting of an enhancer sequence of SEQ ID NO: 8 or SEQ ID NO: 15, and a polyadenylation signal sequence of SEQ ID NO: 16.

Embodiment 104 is the method of any one of claims 92-103, wherein the enhanced immune response comprises an enhanced antibody response against the HBV antigen in the human subject.

Embodiment 105 is the method of embodiment 104, wherein the enhanced immune response comprises an enhanced CD8+ T cell response against the HBV antigen in the human subject.

Embodiment 106 is the method of embodiment 104 or 105, wherein the enhanced immune response comprises an enhanced CD4+ T cell response against the HBV antigen in the human subject.

Embodiment 107 is the method of any one of embodiments 92-106, wherein step (b) is conducted 1-12 weeks after step (a).

Embodiment 108 is the method of any one of embodiments 92-106, wherein step (b) is conducted 2-12 weeks after step (a).

Embodiment 109 is the method of any one of embodiments 92-106, wherein step (b) is conducted at least 1 week after step (a).

Embodiment 110 is the method of any one of embodiments 92-106, wherein step (b) is conducted at least 2 weeks after step (a).

Embodiment 111 is the method of any one of embodiments 92-106, wherein step (b) is conducted at least 4 weeks after step (a).

Embodiment 112 is the method of any one of embodiments 92-106, wherein step (b) is conducted at least 8 weeks after step (a).

Embodiment 113 is the method of any one of embodiments 92-106, wherein step (b) is conducted at least 12 weeks after step (a).

EXAMPLES

The following examples of the application are to further illustrate the nature of the application. It should be understood that the following examples do not limit the invention and the scope of the invention is to be determined by the appended claims.

Example 1: Generation of HBV Core and Pol Antigen Sequences

T-cell epitopes on the hepatitis core protein are considered important for elimination of hepatitis B infection and hepatitis B viral proteins, such as polymerase, may serve to improve the breadth of the response. Thus, hepatitis B core and polymerase proteins were selected as antigens for the design of a therapeutic hepatitis B virus (HBV) vaccine.

Derivation of HBV Core and Polymerase Antigen Consensus Sequences

HBV pol and core antigen consensus sequences were generated based on HBV genotypes B, C, and D. Different HBV sequences were obtained from different sources and aligned separately for core and polymerase proteins. Original sequence alignments for all subtypes (A to H) were subsequently limited to HBV genotypes, B, C, and D. Consensus sequences were defined for each protein alignment in each subtype separately and in all joint BCD sequences. In variable alignment positions, the most frequent amino acid was used in the consensus sequence.

Optimization of HBV Core Antigen

The HBV core antigen consensus sequence was optimized by making two deletions contained in the native viral protein. The first deletion was a deletion of the N-terminal extension of the core protein constituting the pre-core "zinc finger" portion, because reports in the literature have indicated that the virus utilizes this sequence to induce tolerance to viral proteins in infected individuals. The second deletion was a deletion of thirty-four amino acids corresponding to the C-terminal highly positively charged segment, which is required for pre-genome encapsidation and productive viral positive-strand DNA synthesis in the viral life-cycle.

Optimization of the HBV Pol Antigen

The HBV pol antigen consensus sequence was optimized by changing four residues to remove reverse transcriptase and RNAseH enzymatic activities. In particular, the aspartate residues (D) were changed to asparagine residues (N) in the "YXDD" motif of the reverse transcriptase domain to eliminate any coordination function, and thus nucleotide/metal ion binding. Additionally, the first aspartate residue (D) was changed to an asparagine residue (N) and the first glutamate residue (E) was changed to a glutamine residue (A) in the "DEDD" motif of the RNAseH domain to eliminate Mg2+ coordination. Additionally, the sequence of the HBV pol antigen was codon optimized to scramble the internal open reading frames for the envelope proteins, including the S protein and versions of the S protein with the N-terminal extensions pre-S1 and pre-S2. As a result, open reading frames for the envelope proteins (pre-S1, pre-S2, and S protein) and the X protein were removed.

Selection of Signal Peptide for Efficient Protein Secretion

Three different signal peptides introduced in frame at the N-terminus of the HBV core antigen were evaluated: (1) Ig heavy chain gamma signal peptide SPIgG (BAA75024.1); (2) the Ig heavy chain epsilon signal peptide SPIgE (AAB59424.1); and (3) the Cystatin S precursor signal peptide SPCS (NP_0018901.1). Signal peptide cleavage sites were optimized in silico for core fusion using the Signal P prediction program. Secretion efficiency was determined by analyzing core protein levels in the supernatant. Western blot analysis of core antigen secretion using the three different signal peptides fused at the N-terminus demonstrated that the Cystatin S signal peptide resulted in the most efficient protein secretion.

Example 2: Generation of Adenoviral Vectors Expressing a Fusion of Truncated HBV Core Antigen with HBV Pol Antigen An adenovirus vector was created to express a fusion protein of a truncated HBV core antigen and a HBV pol antigen from a single open reading frame. Additional configurations for the expression of the two proteins (e.g., the truncated HBV core antigen and the HBV pol antigen), e.g. using two separate expression cassettes, or using a 2A-like sequence to separate the two sequences, can also be envisaged.

Design of Expression Cassettes for Adenoviral Vectors

Figure 2A:
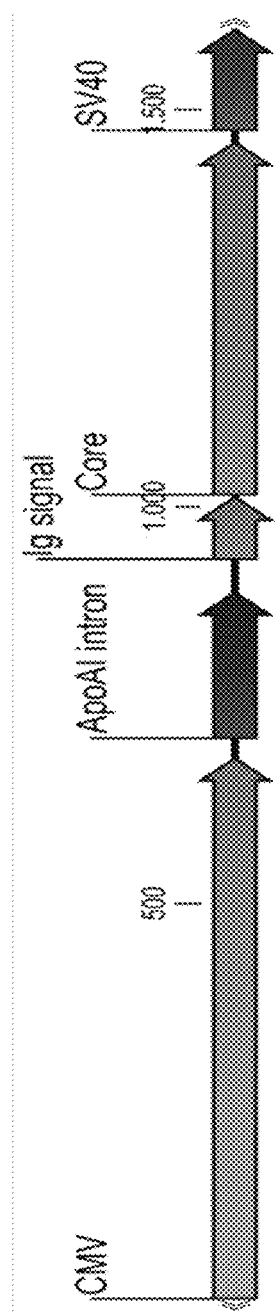
FIGS. 2A-2C show the schematic representations of the expression cassettes in adenoviral and MVA vectors according to embodiments of the application.
Figure 2B:
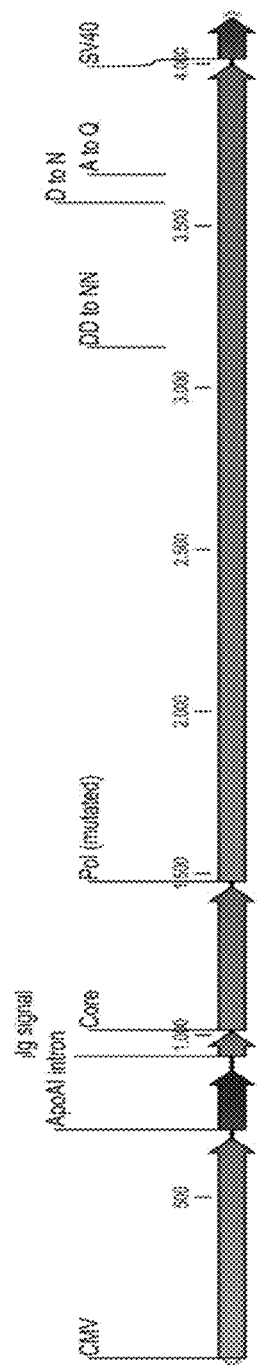

The expression cassettes (diagrammed in FIG. 2A and FIG. 2B) comprise the CMV promoter (SEQ ID NO:7), an intron (SEQ ID NO: 15) (a fragment derived from the human ApoAI gene—GenBank accession X01038 base pairs 295-523, harboring the ApoAI second intron), followed by the optimized coding sequence—either core alone or the core and polymerase fusion protein preceded by a human immunoglobulin secretion signal coding sequence (SEQ ID NO: 10), and followed by the SV40 polyadenylation signal (SEQ ID NO:16).

A secretion signal was included because of past experience showing improvement in the manufacturability of some adenoviral vectors harboring secreted transgenes, without influencing the elicited T-cell response (mouse experiments).

The last two residues of the Core protein (VV) and the first two residues of the Polymerase protein (MP) if fused results in a junction sequence (VVMP) that is present on the human dopamine receptor protein (D3 isoform), along with flanking homologies.

The interjection of an AGAG linker between the core and the polymerase sequences eliminates this homology and returned no further hits in a Blast of the human proteome.

Example 3: Generation of MVA Vectors Expressing a HBV Core Antigen and a HBV Pol Antigen An MVA vector has been designed to encode each of the HBV Core and Pol coding sequences of the application. Each of the HBV Core and Pol coding sequences were inserted into an MVA vector at IGR44/45, each under the control of a separate promoter. Additional configurations for the expression of the two proteins, e.g. using a single expression cassette wherein the Core and Pol antigen comprise a fusion protein, or alternatively utilizing a 2A-like sequence to separate the two sequences, can also be envisaged. Further, additional and/or alternative insertions sites in the MVA vector can also be envisaged, e.g., inserting each of the HBV Core and Pol coding sequences into the same or different insertion sites.

Design of Expression Cassettes for MVA Vectors

Figure 2C:
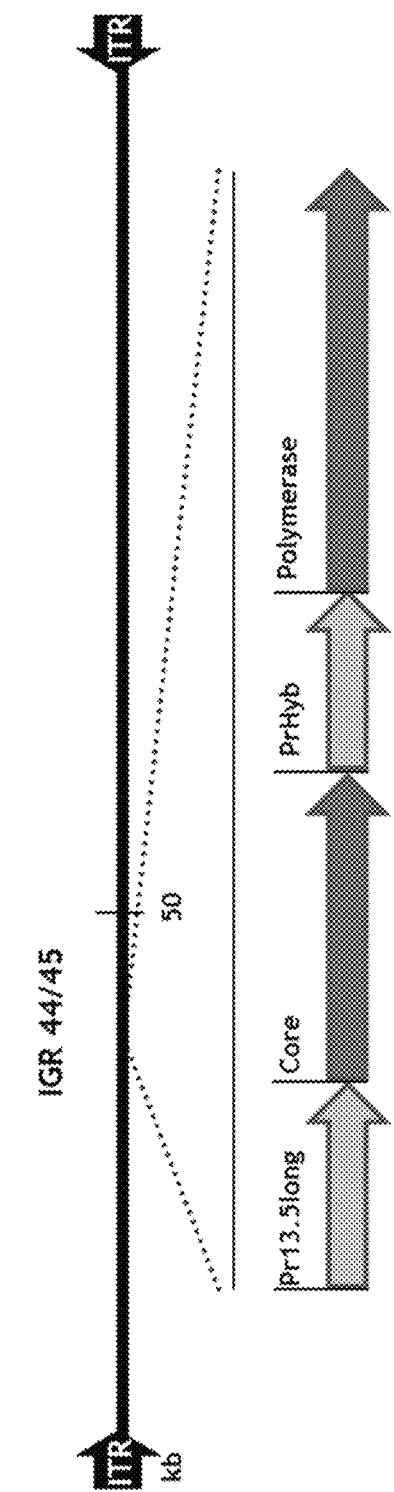

The expression cassettes (diagrammed in FIG. 2C) are comprised of the Pr13.5 long promoter (SEQ ID NO: 25) adjacent to and directing expression of the HBV Core antigen and the PrHyb promoter (SEQ ID NO: 26) adjacent to and directing expression of the HBV Pol antigen. The HBV core coding sequence comprises SEQ ID NO: 1 and the HBV Pol coding sequence comprises SEQ ID NO: 3. Each of SEQ ID NOs: 1 and 3 were modified by eliminating negative cis-acting sites and by adjusting the GC content. Furthermore, each of SEQ ID NOs: 1 and 3 were codon optimized for human codon usage without affecting the amino acid sequence. Each of SEQ ID NOs: 1 and 3 comprises an additional early termination signals (TTTTTNT (SEQ ID NO: 28)) arranged adjacent to the stop codon.

Example 4: Immunogenicity of Combinations of HBV Adenoviral Vectors and HBV MVA Vectors in Mice Materials and Methods
Vector Design:
Two adenoviral vectors expressing either Core alone (an HBV core antigen having the amino acid sequence of SEQ ID NO: 2), or Polymerase (an HBV pol antigen having the amino acid sequence of SEQ ID NO: 4) in addition to Core as a fusion protein expressed from a single open reading frame were used. For this, sequences were designed in silico to provide a consensus for the B, C and D genotypes of the hepatitis B virus. The expression cassettes comprise the CMV promoter, an ApoAI intron, a human immunoglobulin secretion signal, followed by the coding sequence—either Core alone or the Core and Polymerase fusion protein and a SV40 polyadenylation signal.

The recombinant MVA vector is comprised of poxvirus promoter Pr13.5 (SEQ ID NO:25) linked to the core coding sequence (nucleotide sequence of SEQ ID NO: 1, and polypeptide sequence of SEQ ID NO:2) and PrHyb (SEQ ID NO: 26) linked to a nucleotide sequence encoding for polymerase (nucleotide sequence of SEQ ID NO: 3, and polypeptide sequence of SEQ ID NO: 4), both followed by a transcription termination sequence of TTTTTNT (SEQ ID NO: 28). The core coding sequence comprises an N-terminal immunoglobulin secretion tag (SEQ ID NO: 11), and the polymerase coding sequence comprises an N-terminal cystatin S signal sequence (SEQ ID NO:6). See, e.g., FIG. 2C.

In Vivo Immunogenicity Study in Mice:
To evaluate the in vivo immunogenicity of the combination of HBV adenoviral vectors and HBV MVA, F1 mice (C57BL/6×Balb/C) were prime-boost immunized intramuscularly with different vector combinations. These immunogenicity studies focused on determining the cellular immune responses elicited by the HBV antigens Core and Polymerase.

Antigen-specific responses were analyzed and quantified by IFN-γ enzyme-linked immunospot (ELISPOT) and intracellular cytokine production (TNF-alpha, IL-2 and IFN-γ) was detected by flow cytometry. In these assays, isolated splenocytes of immunized animals were incubated with peptide pools covering the Core protein, the Pol protein, or the small peptide leader and junction sequence (2 μg/ml of each peptide). In addition a MVA specific peptide (2 g/ml) was used. The pools consist of 15-mer peptides that overlap by 11 residues matching the genotypes ABCD consensus sequence of the Core and Pol adenoviral vectors. The large 94 kDa HBV Pol protein was split in the middle into two peptide pools. In ELISPOT, IFN-γ release by a single antigen-specific T-cell was visualized by appropriate antibodies and subsequent chromogenic detection as a colored spot on the microplate referred to as spot-forming cell (SFC). In ICS, the percentage of cytokine-releasing cells in a particular population (CD3-positive, CD4-positive or CD8-positive cells) was determined.

Results
Evaluation of Immunogenicity of HBV Adenoviral Vectors and HBV MVA Combinations in Mice:
The purpose of the study was to evaluate the immune response induced by the combination of HBV adenoviral vectors and HBV MVA after IM delivery into F1 mice. The administration to F1 mice was performed as summarized in Table 1. Animals received one HBV adenoviral vector immunization followed by a HBV MVA immunization 8 weeks later. Splenocytes were collected one week after the last immunization.

TABLE 1

Mouse Immunization Experimental Design

| Group | N | Prime Day 0 | R | Dose (vp) | Boost Day 56 | Route | Dose TCID50 | Endpt Day |
|---|---|---|---|---|---|---|---|---|
| 1 | 4 | Core Pol fusion + Core | IM | $10^8$ | — | — | — | 63 |
| 2 | 4 | Core Pol fusion + Core | IM | $10^9$ | — | — | — | 63 |
| 3 | 4 | Core Pol fusion + Core | IM | $10^{10}$ | — | — | — | 63 |
| 4 | 4 | Core Pol fusion + Core | IM | $10^8$ | MVA | IM | $8.9 \times 10^7$ | 63 |
| 5 | 4 | Core Pol fusion + Core | IM | $10^9$ | MVA | IM | $8.9 \times 10^7$ | 63 |
| 6 | 4 | Core Pol fusion + Core | IM | $10^{10}$ | MVA | IM | $8.9 \times 10^7$ | 63 |
| 7 | 4 | Core Pol fusion | IM | $10^8$ | — | — | — | 63 |
| 8 | 4 | Core Pol fusion | IM | $10^9$ | — | — | — | 63 |
| 9 | 4 | Core Pol fusion | IM | $10^{10}$ | — | — | — | 63 |
| 10 | 4 | Core Pol fusion | IM | $10^8$ | MVA | IM | $8.9 \times 10^7$ | 63 |
| 11 | 4 | Core Pol fusion | IM | $10^9$ | MVA | IM | $8.9 \times 10^7$ | 63 |
| 12 | 4 | Core Pol fusion | IM | $10^{10}$ | MVA | IM | $8.9 \times 10^7$ | 63 |
| 13 | 4 | Empty Vector | IM | $10^{10}$ | EV | IM | — | 63 |

Figure 3:
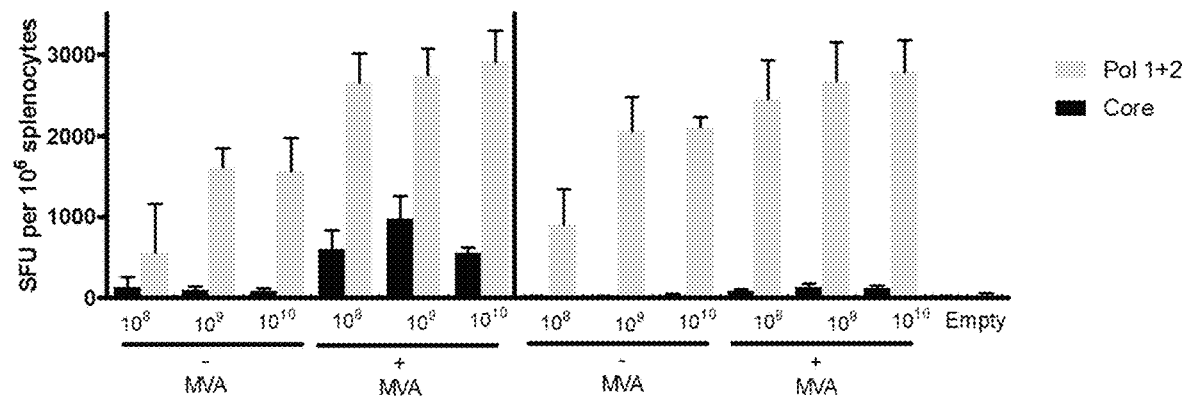
FIG. 3 shows a graph of ELISPOT responses of F1 mice immunized with different combinations of HBV adenoviral vectors and HBV MVA; HBV core or polymerase peptide pools used to stimulate splenocytes isolated from the various vaccinated animal groups are indicated in black (core) and grey (pol). Pol1 and pol2 responses were summed; the X-axis shows the adenovector dose and the presence or absence of the MVA boost; the number of responsive T-cells are indicated on the y-axis expressed as spot forming cells (SFC) per $10^6$ splenocytes.

IM: intramuscular;
vp: viral particles;
TCID50: 50% tissue culture infective dose;
MVA: Modified Vaccinia Ankara HBV adenoviral vectors alone and in combination with HBV MVA vector, gave rise to Pol specific T cell responses in mice. Low-level core responses were induced by Core pol fusion+core adenoviral vectors and these responses where amplified by boosting with HBV MVA vector. The combination of Core pol fusion adenovector and HBV MVA vector also induced core responses (FIG. 3).

Figure 4:
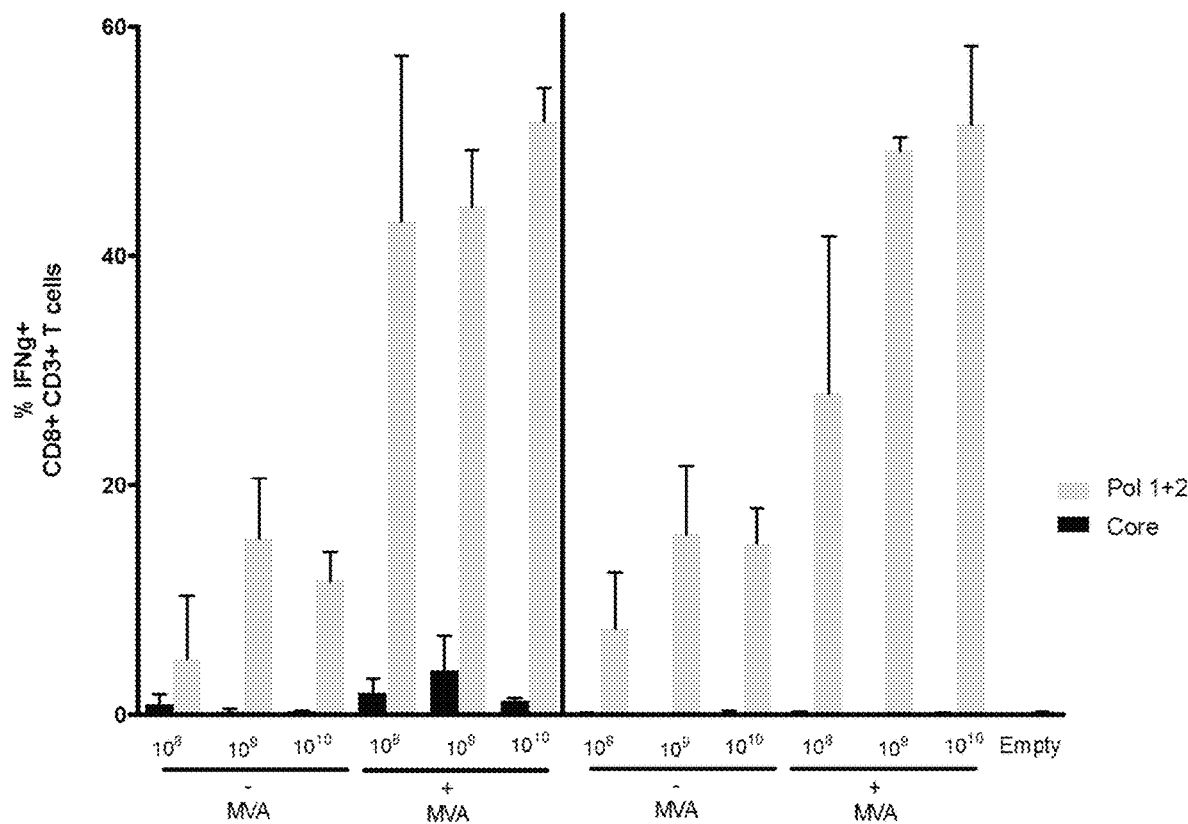
FIG. 4 shows a graph of intracellular cytokine staining (ICS) responses of F1 mice immunized with different combinations of HBV adenoviral vectors and HBV MVA; HBV core and polymerase peptide pools used to stimulate splenocytes isolated from the various vaccinated animal groups are indicated in black (core) and grey (pol); Pol1 and pol2 responses were summed; the X-axis shows the adenovirus vector dose and the presence or absence of the MVA boost. The percentages of CD8(+) T cells positive for IFN γ are shown on the y-axis.
Figure 5:
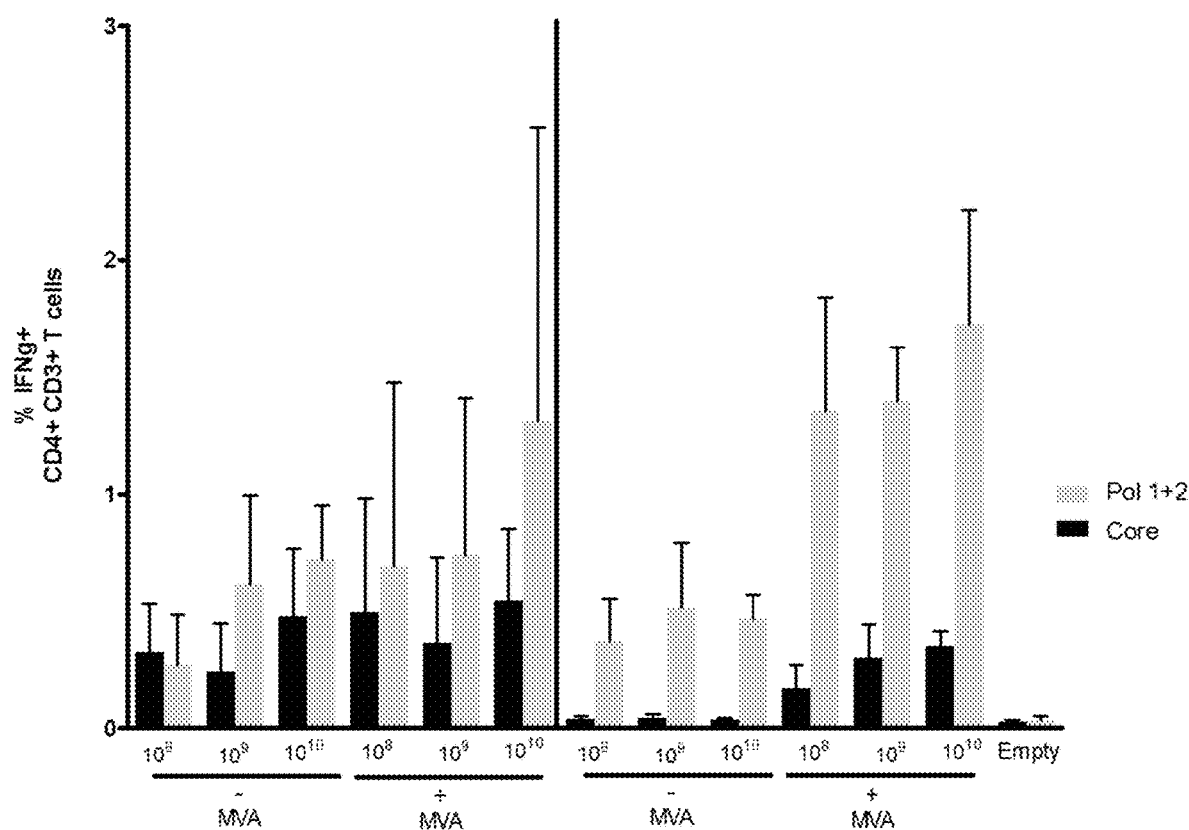
FIG. 5 shows a graph of ICS responses of F1 mice immunized with different combinations of HBV adenoviral vectors and HBV MVA vectors; HBV core and polymerase peptide pools used to stimulate splenocytes isolated from the various vaccinated animal groups are indicated in black (core) and grey (pol); Pol1 and pol2 responses were summed; the X-axis shows the adenoviral vector dose and the presence or absence of the MVA boost; the percentages of CD4(+) T cells positive for IFN γ are shown on the y-axis.

Pol responses are primarily mediated by CD8(+) T cells, whereas Core responses primarily involve CD4(+) T cells (FIGS. 4 and 5). The combination of Core pol fusion+core adenovectors and HBV MVA also induced CD8(+) T cell driven core responses (FIG. 4).

Conclusion:

The combination of HBV adenoviral vectors and HBV MVA vectors gives rise to T cell responses against core and pol in F1 mice.

Example 5: Immunogenicity of Combinations of HBV Adenoviral Vectors and HBV MVA Vectors in Non-Human Primates (NHPs)

In Vivo Immunogenicity Study in NHPs:

To evaluate the in vivo immunogenicity of the combination of HBV adenoviral vectors and HBV MVA vectors, Mauritian cynomolgus monkeys were prime-boost-boost immunized intramuscularly with different vector combinations. These immunogenicity studies focused on determining the cellular immune responses elicited by the HBV core and polymerase antigens.

Antigen-specific responses were analyzed and quantified by IFN-γ enzyme-linked immunospot (ELISPOT) and intracellular cytokine production (TNF-alpha, IL-2 and IFN-γ) was detected by flow cytometry. In these assays, PBMCs of immunized animals were incubated with peptide pools covering the Core protein or the Pol protein (2 μg/ml of each peptide). The pools consist of 15-mer peptides that overlap by 11 residues matching the genotypes ABCD consensus sequence of the Core and Pol adenoviral vectors. The large 94 kDa HBV Pol protein was split in the middle into two peptide pools. In ELISPOT, IFN-γ release by a single antigen-specific T-cell was visualized by appropriate antibodies and subsequent chromogenic detection as a colored spot on the microplate referred to as spot-forming cell (SFC). In intracellular cytokine staining (ICS), the percentage of cytokine-releasing cells in a particular population (CD3-positive, CD4-positive or CD8-positive cells) was determined.

Results

Evaluation of Immunogenicity of HBV Adenoviral Vectors and HBV MVA Vectors Combinations in NHPs:

The purpose of the study was to evaluate the immune response induced by the combination of HBV adenoviral vectors and HBV MVA vectors after IM delivery into Mauritian cynomolgus monkeys. The administration to NHPs was performed as summarized in Table 2. Animals received one HBV adenoviral vector immunization followed by a HBV MVA vector immunization 8 weeks later and again followed by a HBV adenoviral vector immunization 8 weeks later. PBMCs were collected two weeks after each immunization.

TABLE 2

NHP Immunization Experimental Design

| Group | N | Prime Day 0 | R | Dose per vector (vp) | Boost Day 56 | R | Dose TCID50 | Boost Day 112 | Dose (vp) | R |
|---|---|---|---|---|---|---|---|---|---|---|
| 1 | 8 | Core Pol fusion | IM | $5*10^{10}$ | MVA | IM | $5*10^{8}$ | Core Pol fusion | $1*10^{11}$ | IM |
| 2 | 8 | Core Pol fusion + Core | IM | $5*10^{10}$ | MVA | IM | $5*10^{8}$ | Core Pol fusion | $1*10^{11}$ | IM |

Figure 6:
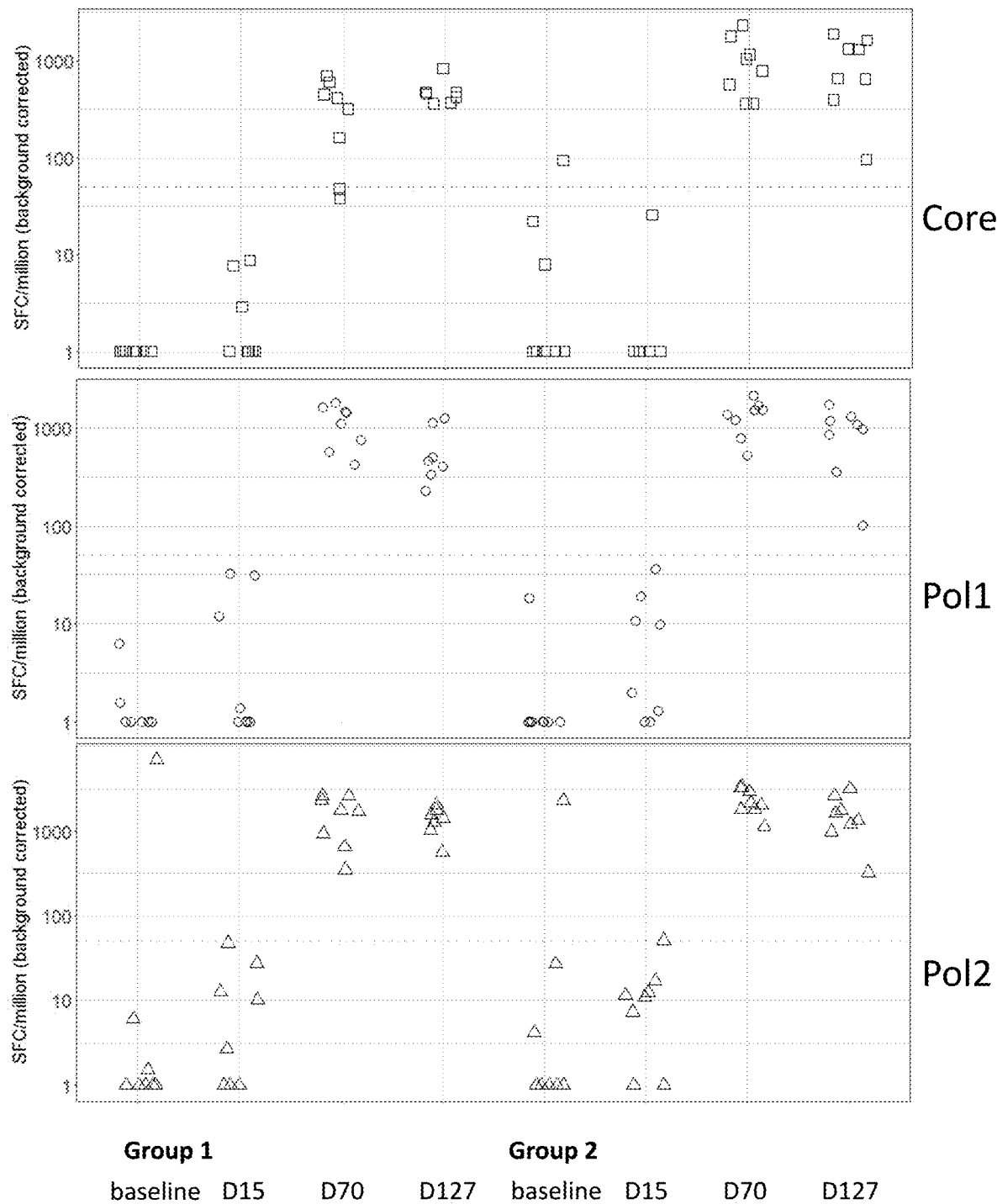
FIG. 6 shows a graph of ELISPOT responses of NHPs immunized with different combinations of HBV adenoviral vectors and HBV MVA vectors; HBV core or polymerase peptide pools used to stimulate PBMCs isolated from the various vaccinated animal groups are indicated in squares (core), circles (pol1) and triangles (pol2); the X-axis shows the different experimental groups and timepoints. The number of responsive T-cells are indicated on the y-axis expressed as spot forming cells (SFC) per $10^6$ splenocytes; background (medium+DMSO stimulation) subtracted data is shown.

IM: intramuscular;
vp: viral particles;
TCID50: 50% tissue culture infective dose;
MVA: Modified Vaccinia Ankara Core pol fusion adenoviral vector alone and Core pol fusion+core adenoviral vectors in combination with HBV MVA vector, gave rise to robust Pol and Core specific T cell responses in NHPs. Further boosting with a Core pol fusion adenoviral vector did not further increase the response (FIG. 6).

Figure 7A:
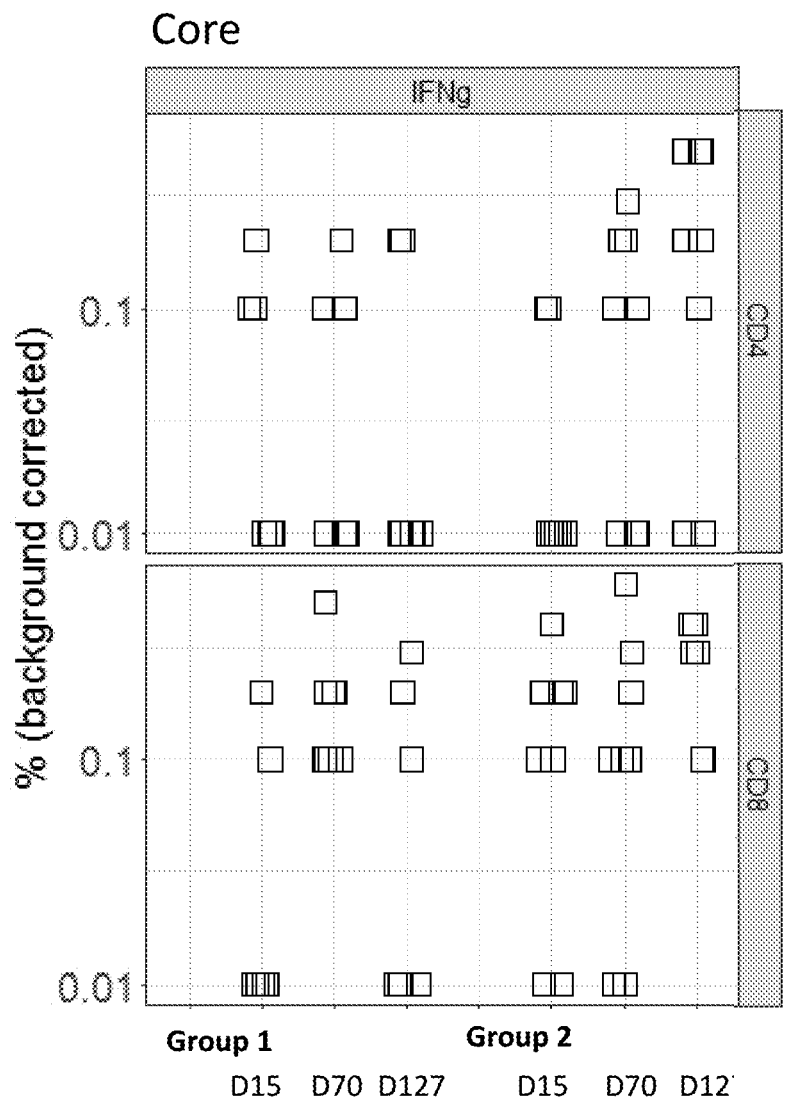
FIGS. 7A, 7B and 7C show graphs of ICS responses of NHPs immunized with different combinations of HBV adenoviral vectors and HBV MVA vectors; HBV core and polymerase peptide pools used to stimulate PBMCs isolated from the various vaccinated animal groups are indicated in squares (core), circles (pol1) and triangles (pol2); the X-axis shows the different experimental groups and time points; the percentages of CD4(+) and CD8(+) T cells positive for IFN γ are shown on the y-axis; background (medium+DMSO stimulation) subtracted data is shown.
Figure 7B:
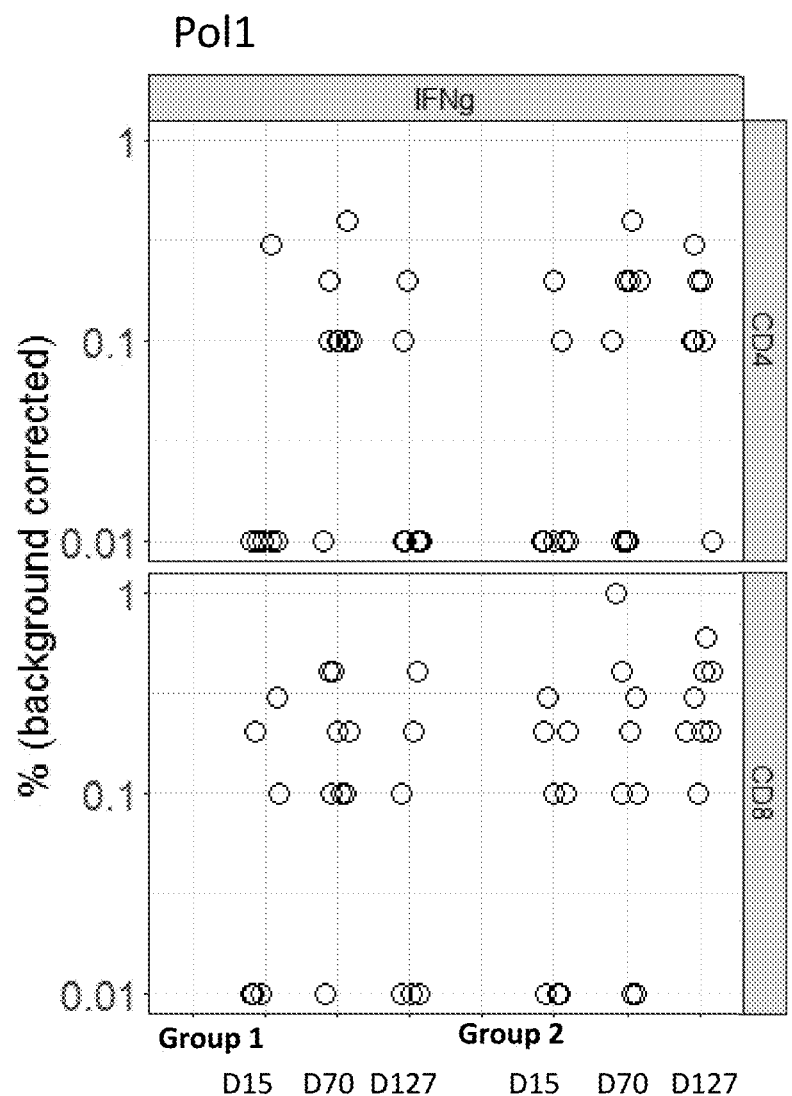
Figure 7C:
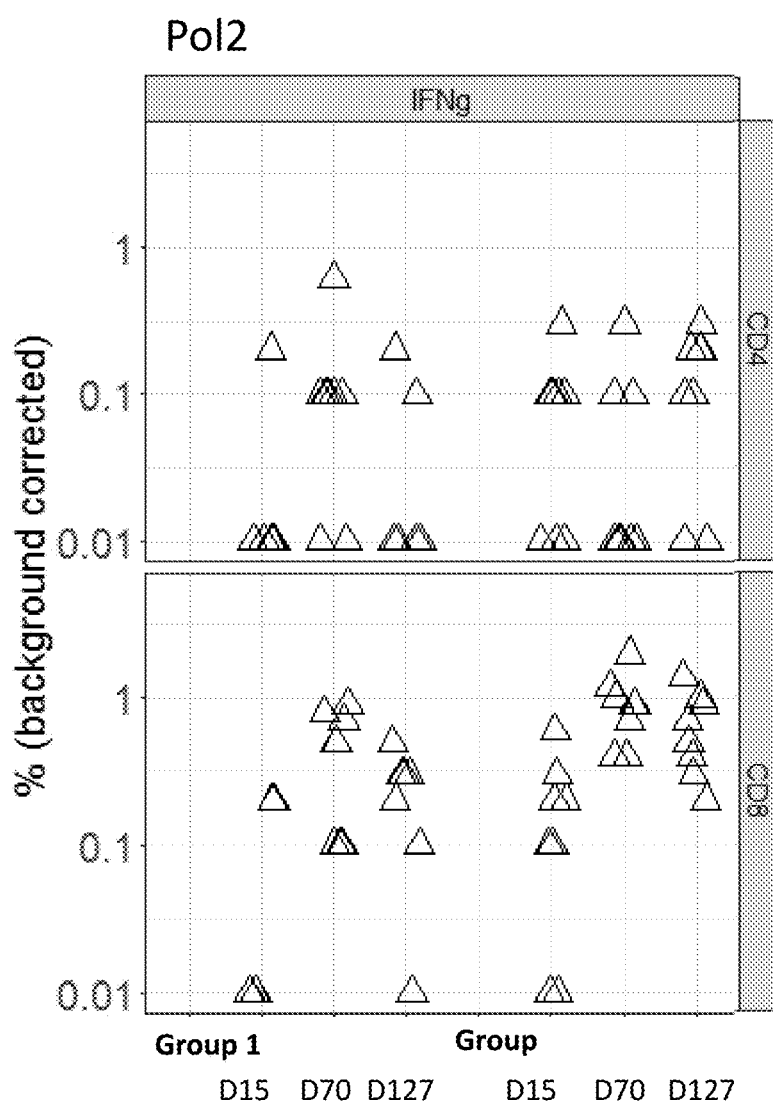

Core and Pol responses in NHPs are mediated by both CD4(+) and CD8(+) T cells. The combination of Core pol fusion adenovectors+core adenovectors (used as a prime) and HBV MVA (used as a boost) induced the highest CD4(+) Core specific and CD8(+) Pol specific T cell IFN-γ responses (FIG. 7).

These results demonstrate that the combination of HBV adenoviral vectors and HBV MVA vectors gave rise to robust T cell responses against the core and pol antigens in NHPs.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

REFERENCES

1. Cohen et al. "Is chronic hepatitis B being undertreated in the United States?" J. Viral Hepat. (2011) 18(6), 377-83.
2. Obeng-Adjei et al. "DNA vaccine cocktail expressing genotype A and C HBV surface and consensus core antigens generates robust cytotoxic and antibody responses and mice and Rhesus macaques" Cancer Gene Therapy (2013) 20, 652-662.
3. World Health Organization, Hepatitis B: Fact sheet No. 204 [Internet] 2015 March. Available from http://www.who.nt/mediacentre/factsheets/fs204/en/.
4. Belloni et al. "IFN-α inhibits HBV transcription and replication in cell culture and in humanized mice by targeting the epigenetic regulation of the nuclear cccDNA minichromosome" J. Clin. Invest. (2012) 122(2), 529-537.
5. Michel et al. "Therapeutic vaccines and immune-based therapies for the treatment of chronic hepatitis B: perspectives and challenges." J. Hepatol. (2011) 54(6), 1286-1296.

It is claimed:

1. A Modified Vaccinia Ankara (MVA) vector comprising a non-naturally occurring nucleic acid molecule comprising a first polynucleotide sequence encoding an HBV polymerase antigen comprising an amino acid sequence that is at least 98% identical to SEQ ID NO: 4.

2. The MVA vector of claim 1, wherein the HBV polymerase antigen comprises the amino acid sequence of SEQ ID NO: 4.

3. The MVA vector of claim 1, wherein the first polynucleotide sequence comprises the polynucleotide sequence of SEQ ID NO: 3.

4. A composition comprising the MVA vector of claim 1 and a pharmaceutically acceptable carrier.

5. The MVA vector of claim 1, wherein the HBV polymerase antigen is capable of inducing an immune response in a mammal against at least two HBV genotypes.

6. The MVA vector of claim 1, wherein the HBV polymerase antigen is capable of inducing a T cell response in a mammal against at least HBV genotypes B, C and D.

7. The MVA vector of claim 1, wherein the HBV polymerase antigen is capable of inducing a CD8 T cell response in a human subject against at least HBV genotypes A, B, C, and D.

8. The MVA vector of claim 1, further comprising a polynucleotide sequence encoding a signal sequence operably linked to the HBV polymerase antigen.

9. The MVA vector of claim 8, wherein the signal sequence comprises the amino acid sequence of SEQ ID NO: 6 or SEQ ID NO: 11.

10. The MVA vector of claim 8, wherein the signal sequence is encoded by the polynucleotide sequence of SEQ ID NO: 5 or SEQ ID NO: 10.

11. The MVA vector of claim 1, wherein the first polynucleotide sequence is at least 90% identical to SEQ ID NO: 3.

12. The MVA vector of claim 1, wherein the first polynucleotide sequence is at least 90% identical to SEQ ID NO: 19.

13. The MVA vector of claim 12, wherein the first polynucleotide sequence comprises the polynucleotide sequence of SEQ ID NO: 19.

14. The MVA vector of claim 1, wherein the first polynucleotide sequence is at least 90% identical to SEQ ID NO: 20.

15. The MVA vector of claim 14, wherein the first polynucleotide sequence comprises the polynucleotide sequence of SEQ ID NO: 20.

16. The MVA vector of claim 1, wherein the HBV polymerase antigen does not have reverse transcriptase activity and RNase H activity.

17. The MVA vector of claim 16, wherein the HBV polymerase comprises an amino acid sequence that is at least 99% identical to SEQ ID NO: 4.

18. The MVA vector of claim 16, wherein the HBV polymerase comprises the amino acid sequence of SEQ ID NO: 4.

19. The MVA vector of claim 16, wherein the HBV polymerase antigen is capable of inducing a T cell response in a mammal against at least HBV genotypes B, C and D.

20. The MVA vector of claim 16, wherein the HBV polymerase antigen is capable of inducing a CD8 T cell response in a human subject against at least HBV genotypes A, B, C, and D.

* * * * *

SEQUENCE LISTING

<160> NUMBER OF SEQ ID NOS: 28

<210> SEQ ID NO 1
<211> LENGTH: 447
<212> TYPE: DNA
<213> ORGANISM: Artificial Sequence
<220> FEATURE:
<223> OTHER INFORMATION: HBV core

<400> SEQUENCE: 1

```
atggacatcg atccctacaa ggagttcggt gccagcgtgg aactgctgag cttcctgccc     60
agcgacttct tcccttccat cagagacctg ctggacactg ccagcgcact gtacagagag    120
gctctggaaa gccctgagca ctgcagccct caccacaccg ctctgagaca ggccatcctg    180
tgctggggag agctgatgaa cctggccacc tgggtcggaa gcaacctgga agatccagcc    240
agtcgcgagc tggtggtgtc ctacgtgaac gtgaacatgg gcttgaagat ccggcagctc    300
ctgtggttcc acatcagctg cctgaccttc ggacgggaaa ccgtgctgga atacctggtg    360
tcctttggcg tgtggatccg gacacctcca gcctacagac tcccaacgc tcctatcctg     420
agcaccctgc ctgagacaac cgtggtg                                        447
```

<210> SEQ ID NO 2
<211> LENGTH: 149
<212> TYPE: PRT
<213> ORGANISM: Artificial Sequence
<220> FEATURE:
<223> OTHER INFORMATION: HBV core

<400> SEQUENCE: 2

```
Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val
145
```

<210> SEQ ID NO 3
<211> LENGTH: 2529
<212> TYPE: DNA
<213> ORGANISM: Artificial Sequence
<220> FEATURE:
<223> OTHER INFORMATION: HBV pol

```
<400> SEQUENCE: 3
atgcctctga gctaccagca ctttcggaag ctgctgctcc tggacgacga ggccggacct      60
ctggaagagg aactgcccag actggcagac gagggtctga cagaagagt ggccgaggac      120
ctgaacctgg caacctgaa cgtgtccatc ccttggaccc acaaggtcgg aaacttcacc      180
ggtctgtaca gcagcaccgt gcctgtgttc aaccctgagt ggcagacacc cagctttccc     240
aacatccatc tgcaggaaga tatcatcaac cgctgcgagc agttcgtggg acctctgacc      300
gtgaacgaga gcggagact gaagctgatc atgccagcca gattctaccc taacgtgacc     360
aagtacctgc ctctggacaa gggcatcaag ccctactacc ctgagcacct ggtcaaccac     420
tacttccaga ccagacacta cctgcacacc ctgtggaagg ccggcatcct gtacaagaga     480
gagacaacca gaagcgccag cttctgcggc agcccttaca ctgggagca ggaactccag     540
cacggacgcc tggtgttcca gaccagcacc agacacggcg acgagagctt ttgccagcag     600
agcagcggca tcctgagcag atctcctgtg gtccttgcc tgcagagcca gctgaggaag     660
tccagactgg gcctgcagcc tcagcaggga catctggcta cggcagca gggcagaagc      720
ggcagcatca gagccagagt gcaccctacc accagacggc ctttcggcgt ggaacctagc     780
ggctctggcc acaccaccaa caccgcctct agctccagct cctgcctgca ccagtcagcc     840
gtgcggaagg ctgcctacag ccacctgagc accagcaaga gacacagcag ctccggacac     900
gctgtcgagc tgcacaacat ccctcccaac agcgccagaa ccagagcga gggtcctgtg     960
ttcagctgtt ggtggctgca gttccggaac agcaagccct gcagcgacta ctgcctgagc    1020
cacatcgtga acctgctgga agattgggga ccttgcaccg agcacggcga gcaccacatc    1080
cggatcccta gaacaccagc cagagtgaca ggaggcgtgt cctcgtgga caagaaccct     1140
cacaacacca ccgagagcag actggtggtg gacttcagcc agttctccag aggcaacacc    1200
agagtgtcct ggcccaagtt cgccgttccc aacctgcagt ccctgaccaa cctgctgagc    1260
agcaacctga ctggctgag cctggacgtg tccgctgcct tctaccatct gcctctgcac    1320
cctgcagcca tgcctcatct gctcgttggc agcagcggac tgtccagata cgtggctcgg    1380
ctgtccagca ctctcggat catcaaccac cagcacggca ccatgcagaa cctgcacgac     1440
agctgcagca gaaatctgta tgtgtccctg ctcctgctgt acaagacctt tggccggaag    1500
ctgcacctgt acagccatcc catcatcctg ggcttccgga agatccctat gggcgtggga    1560
ctgagcccat tcctgctggc ccagttcacc agcgccatct gcagcgtcgt gcggagagcc    1620
ttccctcact gcctggcctt cagctacatg aacaacgtgg tgctgggcgc caagagcgtg    1680
cagcacctgg aatccctgtt taccgccgtg accaacttcc tgctgtccct gggcatccac    1740
ctgaatccca caagaccaa gagatgggga tacagcctga acttcatggg ctacgtgatc    1800
ggcagctggg gcacactgcc tcaggaacac atcgtccaga agatcaaaga gtgcttccgc    1860
aagcttcccg tgaacagacc catcgactgg aaagtgtgcc agcggatcgt tggactgctg    1920
ggcttttgcag ctcctttcac ccagtgcggc taccctgctc tgatgcctct gtacgcctgc    1980
atccagagca agcaggcctt caccttcagc cctacctaca aggccttcct gtgcaagcag    2040
tacctgaatc tgtaccctgt ggccagacag agaccaggcc tgtgccaggt gttcgccaat    2100
gccacaccta ccggctgggg ccttgccatt ggccaccaga gaatgagagg caccttcgtg    2160
gctcctctgc ccatccacac agcccagctg ctggctgcct gcttcgccag aagcagatcc    2220
ggagccaagc tgatcggcac cgacaactcc gtggtgctga ccggaagta caccagcttc    2280
ccttggctgc tgggctgcgc tgccaactgg atcctgcgag gcaccagctt cgtgtacgtg    2340
```

```
cctctgccc tgaaccctgc cgacgaccct tctagaggca ggctgggact gtacagacct    2400
ctgcttagac tgcccttcag acccaccacc ggacggacca gcctgtacgc cgatagccct    2460
agcgtgccca gccatctgcc cgacagagtg cacttcgcca gccctctgca tgtggcctgg    2520
agacctcca                                                            2529

<210> SEQ ID NO 4
<211> LENGTH: 843
<212> TYPE: PRT
<213> ORGANISM: Artificial Sequence
<220> FEATURE:
<223> OTHER INFORMATION: HBV pol

<400> SEQUENCE: 4

Met Pro Leu Ser Tyr Gln His Phe Arg Lys Leu Leu Leu Leu Asp Asp
1               5                   10                  15

Glu Ala Gly Pro Leu Glu Glu Glu Leu Pro Arg Leu Ala Asp Glu Gly
                20                  25                  30

Leu Asn Arg Arg Val Ala Glu Asp Leu Asn Leu Gly Asn Leu Asn Val
        35                  40                  45

Ser Ile Pro Trp Thr His Lys Val Gly Asn Phe Thr Gly Leu Tyr Ser
    50                  55                  60

Ser Thr Val Pro Val Phe Asn Pro Glu Trp Gln Thr Pro Ser Phe Pro
65                  70                  75                  80

Asn Ile His Leu Gln Glu Asp Ile Ile Asn Arg Cys Glu Gln Phe Val
                85                  90                  95

Gly Pro Leu Thr Val Asn Glu Lys Arg Arg Leu Lys Leu Ile Met Pro
            100                 105                 110

Ala Arg Phe Tyr Pro Asn Val Thr Lys Tyr Leu Pro Leu Asp Lys Gly
        115                 120                 125

Ile Lys Pro Tyr Tyr Pro Glu His Leu Val Asn His Tyr Phe Gln Thr
    130                 135                 140

Arg His Tyr Leu His Thr Leu Trp Lys Ala Gly Ile Leu Tyr Lys Arg
145                 150                 155                 160

Glu Thr Thr Arg Ser Ala Ser Phe Cys Gly Ser Pro Tyr Ser Trp Glu
                165                 170                 175

Gln Glu Leu Gln His Gly Arg Leu Val Phe Gln Thr Ser Thr Arg His
            180                 185                 190

Gly Asp Glu Ser Phe Cys Gln Gln Ser Ser Gly Ile Leu Ser Arg Ser
        195                 200                 205

Pro Val Gly Pro Cys Leu Gln Ser Gln Leu Arg Lys Ser Arg Leu Gly
    210                 215                 220

Leu Gln Pro Gln Gln Gly His Leu Ala Arg Arg Gln Gln Gly Arg Ser
225                 230                 235                 240

Gly Ser Ile Arg Ala Arg Val His Pro Thr Thr Arg Arg Pro Phe Gly
                245                 250                 255

Val Glu Pro Ser Gly Ser Gly His Thr Thr Asn Thr Ala Ser Ser Ser
            260                 265                 270

Ser Ser Cys Leu His Gln Ser Ala Val Arg Lys Ala Ala Tyr Ser His
        275                 280                 285

Leu Ser Thr Ser Lys Arg His Ser Ser Ser Gly His Ala Val Glu Leu
    290                 295                 300

His Asn Ile Pro Pro Asn Ser Ala Arg Ser Gln Ser Glu Gly Pro Val
305                 310                 315                 320
```

```
Phe Ser Cys Trp Trp Leu Gln Phe Arg Asn Ser Lys Pro Cys Ser Asp
                325                 330                 335

Tyr Cys Leu Ser His Ile Val Asn Leu Leu Glu Asp Trp Gly Pro Cys
            340                 345                 350

Thr Glu His Gly Glu His His Ile Arg Ile Pro Arg Thr Pro Ala Arg
        355                 360                 365

Val Thr Gly Gly Val Phe Leu Val Asp Lys Asn Pro His Asn Thr Thr
    370                 375                 380

Glu Ser Arg Leu Val Val Asp Phe Ser Gln Phe Ser Arg Gly Asn Thr
385                 390                 395                 400

Arg Val Ser Trp Pro Lys Phe Ala Val Pro Asn Leu Gln Ser Leu Thr
                405                 410                 415

Asn Leu Leu Ser Ser Asn Leu Ser Trp Leu Ser Leu Asp Val Ser Ala
            420                 425                 430

Ala Phe Tyr His Leu Pro Leu His Pro Ala Ala Met Pro His Leu Leu
        435                 440                 445

Val Gly Ser Ser Gly Leu Ser Arg Tyr Val Ala Arg Leu Ser Ser Asn
    450                 455                 460

Ser Arg Ile Ile Asn His Gln His Gly Thr Met Gln Asn Leu His Asp
465                 470                 475                 480

Ser Cys Ser Arg Asn Leu Tyr Val Ser Leu Leu Leu Leu Tyr Lys Thr
                485                 490                 495

Phe Gly Arg Lys Leu His Leu Tyr Ser His Pro Ile Ile Leu Gly Phe
            500                 505                 510

Arg Lys Ile Pro Met Gly Val Gly Leu Ser Pro Phe Leu Leu Ala Gln
        515                 520                 525

Phe Thr Ser Ala Ile Cys Ser Val Val Arg Arg Ala Phe Pro His Cys
    530                 535                 540

Leu Ala Phe Ser Tyr Met Asn Asn Val Val Leu Gly Ala Lys Ser Val
545                 550                 555                 560

Gln His Leu Glu Ser Leu Phe Thr Ala Val Thr Asn Phe Leu Leu Ser
                565                 570                 575

Leu Gly Ile His Leu Asn Pro Asn Lys Thr Lys Arg Trp Gly Tyr Ser
            580                 585                 590

Leu Asn Phe Met Gly Tyr Val Ile Gly Ser Trp Gly Thr Leu Pro Gln
        595                 600                 605

Glu His Ile Val Gln Lys Ile Lys Glu Cys Phe Arg Lys Leu Pro Val
    610                 615                 620

Asn Arg Pro Ile Asp Trp Lys Val Cys Gln Arg Ile Val Gly Leu Leu
625                 630                 635                 640

Gly Phe Ala Ala Pro Phe Thr Gln Cys Gly Tyr Pro Ala Leu Met Pro
                645                 650                 655

Leu Tyr Ala Cys Ile Gln Ser Lys Gln Ala Phe Thr Phe Ser Pro Thr
            660                 665                 670

Tyr Lys Ala Phe Leu Cys Lys Gln Tyr Leu Asn Leu Tyr Pro Val Ala
        675                 680                 685

Arg Gln Arg Pro Gly Leu Cys Gln Val Phe Ala Asn Ala Thr Pro Thr
    690                 695                 700

Gly Trp Gly Leu Ala Ile Gly His Gln Arg Met Arg Gly Thr Phe Val
705                 710                 715                 720

Ala Pro Leu Pro Ile His Thr Ala Gln Leu Leu Ala Ala Cys Phe Ala
                725                 730                 735
```

```
Arg Ser Arg Ser Gly Ala Lys Leu Ile Gly Thr Asp Asn Ser Val Val
            740                 745                 750

Leu Ser Arg Lys Tyr Thr Ser Phe Pro Trp Leu Leu Gly Cys Ala Ala
        755                 760                 765

Asn Trp Ile Leu Arg Gly Thr Ser Phe Val Tyr Val Pro Ser Ala Leu
    770                 775                 780

Asn Pro Ala Asp Asp Pro Ser Arg Gly Arg Leu Gly Leu Tyr Arg Pro
785                 790                 795                 800

Leu Leu Arg Leu Pro Phe Arg Pro Thr Thr Gly Arg Thr Ser Leu Tyr
                805                 810                 815

Ala Asp Ser Pro Ser Val Pro Ser His Leu Pro Asp Arg Val His Phe
            820                 825                 830

Ala Ser Pro Leu His Val Ala Trp Arg Pro Pro
        835                 840
```

<210> SEQ ID NO 5
<211> LENGTH: 63
<212> TYPE: DNA
<213> ORGANISM: Artificial Sequence
<220> FEATURE:
<223> OTHER INFORMATION: Cystatin S signal peptide

<400> SEQUENCE: 5

```
atggctcgac ctctgtgtac cctgctactc ctgatggcta ccctggctgg agctctggcc    60
agc                                                                  63
```

<210> SEQ ID NO 6
<211> LENGTH: 21
<212> TYPE: PRT
<213> ORGANISM: Artificial Sequence
<220> FEATURE:
<223> OTHER INFORMATION: Cystatin S signal peptide

<400> SEQUENCE: 6

```
Met Ala Arg Pro Leu Cys Thr Leu Leu Leu Met Ala Thr Leu Ala
1               5                   10                  15

Gly Ala Leu Ala Ser
            20
```

<210> SEQ ID NO 7
<211> LENGTH: 684
<212> TYPE: DNA
<213> ORGANISM: Artificial Sequence
<220> FEATURE:
<223> OTHER INFORMATION: hCMV promoter

<400> SEQUENCE: 7

```
accgccatgt tgacattgat tattgactag ttattaatag taatcaatta cggggtcatt    60
agttcatagc ccatatatgg agttccgcgt tacataactt acggtaaatg gcccgcctgg   120
ctgaccgccc aacgaccccc gcccattgac gtcaataatg acgtatgttc ccatagtaac   180
gccaataggg actttccatt gacgtcaatg ggtggagtat ttacggtaaa ctgcccactt   240
ggcagtacat caagtgtatc atatgccaag tacgccccct attgacgtca atgacggtaa   300
atggcccgcc tggcattatg cccagtacat gaccttatgg gactttccta cttggcagta   360
catctacgta ttagtcatcg ctattaccat ggtgatgcgg ttttggcagt acatcaatgg   420
gcgtggatag cggtttgact cacggggatt tccaagtctc cacccccattg acgtcaatgg   480
gagtttgttt tggcaccaaa atcaacggga ctttccaaaa tgtcgtaaca actccgcccc   540
```

```
attgacgcaa atgggcggta ggcgtgtacg gtgggaggtc tatataagca gagctcgttt      600
agtgaaccgt cagatcgcct ggagacgcca tccacgctgt tttgacctcc atagaagaca      660
ccgggaccga tccagcctcc gcgg                                             684
```

<210> SEQ ID NO 8
<211> LENGTH: 378
<212> TYPE: DNA
<213> ORGANISM: Artificial Sequence
<220> FEATURE:
<223> OTHER INFORMATION: triple enhancer

<400> SEQUENCE: 8

```
ggctcgcatc tctccttcac gcgcccgccg ccctacctga ggccgccatc cacgccggtt       60
gagtcgcgtt ctgccgcctc ccgcctgtgg tgcctcctga actgcgtccg ccgtctaggt      120
aagtttaaag ctcaggtcga gaccgggcct ttgtccggcg ctcccttgga gcctacctag      180
actcagccgg ctctccacgc tttgcctgac cctgcttgct caactctagt tctctcgtta      240
acttaatgag acagatagaa actggtcttg tagaaacaga gtagtcgcct gcttttctgc      300
caggtgctga cttctctccc ctgggctttt tcttttttct caggttgaaa agaagaagac      360
gaagaagacg aagaagac                                                    378
```

<210> SEQ ID NO 9
<211> LENGTH: 225
<212> TYPE: DNA
<213> ORGANISM: Artificial Sequence
<220> FEATURE:
<223> OTHER INFORMATION: BGH poly A

<400> SEQUENCE: 9

```
ctgtgccttc tagttgccag ccatctgttg tttgcccctc cccgtgcct tccttgaccc        60 tggaaggtgc cactcccact gtcctttcct aataaaatga ggaaattgca tcgcattgtc      120
tgagtaggtg tcattctatt ctgggggtg gggtggggca ggacagcaag ggggaggatt      180
gggaagacaa tagcaggcat gctggggatg cggtgggctc tatgg                     225
```

<210> SEQ ID NO 10
<211> LENGTH: 81
<212> TYPE: DNA
<213> ORGANISM: Artificial Sequence
<220> FEATURE:
<223> OTHER INFORMATION: Immunoglobulin secretion signal

<400> SEQUENCE: 10

```
atggagttcg gcctgtcttg ggtctttctg gtggcaatcc tgaagggcgt gcagtgtgaa       60
gtgcagctgc tggagtctgg a                                                81
```

<210> SEQ ID NO 11
<211> LENGTH: 27
<212> TYPE: PRT
<213> ORGANISM: Artificial Sequence
<220> FEATURE:
<223> OTHER INFORMATION: Immunoglobulin secretion signal

<400> SEQUENCE: 11

```
Met Glu Phe Gly Leu Ser Trp Val Phe Leu Val Ala Ile Leu Lys Gly
1               5                   10                  15

Val Gln Cys Glu Val Gln Leu Leu Glu Ser Gly
            20                  25
```

<210> SEQ ID NO 12
<211> LENGTH: 996
<212> TYPE: PRT
<213> ORGANISM: Artificial Sequence
<220> FEATURE:
<223> OTHER INFORMATION: Core-Pol fusion

<400> SEQUENCE: 12

```
Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Ala Gly Ala Gly Met Pro Leu Ser Tyr Gln His
145                 150                 155                 160

Phe Arg Lys Leu Leu Leu Leu Asp Asp Glu Ala Gly Pro Leu Glu Glu
                165                 170                 175

Glu Leu Pro Arg Leu Ala Asp Glu Gly Leu Asn Arg Arg Val Ala Glu
            180                 185                 190

Asp Leu Asn Leu Gly Asn Leu Asn Val Ser Ile Pro Trp Thr His Lys
        195                 200                 205

Val Gly Asn Phe Thr Gly Leu Tyr Ser Ser Thr Val Pro Val Phe Asn
    210                 215                 220

Pro Glu Trp Gln Thr Pro Ser Phe Pro Asn Ile His Leu Gln Glu Asp
225                 230                 235                 240

Ile Ile Asn Arg Cys Glu Gln Phe Val Gly Pro Leu Thr Val Asn Glu
                245                 250                 255

Lys Arg Arg Leu Lys Leu Ile Met Pro Ala Arg Phe Tyr Pro Asn Val
            260                 265                 270

Thr Lys Tyr Leu Pro Leu Asp Lys Gly Ile Lys Pro Tyr Tyr Pro Glu
        275                 280                 285

His Leu Val Asn His Tyr Phe Gln Thr Arg His Tyr Leu His Thr Leu
    290                 295                 300

Trp Lys Ala Gly Ile Leu Tyr Lys Arg Glu Thr Thr Arg Ser Ala Ser
305                 310                 315                 320

Phe Cys Gly Ser Pro Tyr Ser Trp Glu Gln Glu Leu Gln His Gly Arg
                325                 330                 335

Leu Val Phe Gln Thr Ser Thr Arg His Gly Asp Glu Ser Phe Cys Gln
            340                 345                 350

Gln Ser Ser Gly Ile Leu Ser Arg Ser Pro Val Gly Pro Cys Leu Gln
        355                 360                 365
```

-continued

```
Ser Gln Leu Arg Lys Ser Arg Leu Gly Leu Gln Pro Gln Gln Gly His
370                 375                 380

Leu Ala Arg Arg Gln Gln Gly Arg Ser Gly Ser Ile Arg Ala Arg Val
385                 390                 395                 400

His Pro Thr Thr Arg Arg Pro Phe Gly Val Glu Pro Ser Gly Ser Gly
                405                 410                 415

His Thr Thr Asn Thr Ala Ser Ser Ser Ser Cys Leu His Gln Ser
                420                 425                 430

Ala Val Arg Lys Ala Ala Tyr Ser His Leu Ser Thr Ser Lys Arg His
            435                 440                 445

Ser Ser Ser Gly His Ala Val Glu Leu His Asn Ile Pro Pro Asn Ser
450                 455                 460

Ala Arg Ser Gln Ser Glu Gly Pro Val Phe Ser Cys Trp Trp Leu Gln
465                 470                 475                 480

Phe Arg Asn Ser Lys Pro Cys Ser Asp Tyr Cys Leu Ser His Ile Val
                485                 490                 495

Asn Leu Leu Glu Asp Trp Gly Pro Cys Thr Glu His Gly Glu His His
                500                 505                 510

Ile Arg Ile Pro Arg Thr Pro Ala Arg Val Thr Gly Gly Val Phe Leu
            515                 520                 525

Val Asp Lys Asn Pro His Asn Thr Thr Glu Ser Arg Leu Val Val Asp
530                 535                 540

Phe Ser Gln Phe Ser Arg Gly Asn Thr Arg Val Ser Trp Pro Lys Phe
545                 550                 555                 560

Ala Val Pro Asn Leu Gln Ser Leu Thr Asn Leu Leu Ser Ser Asn Leu
                565                 570                 575

Ser Trp Leu Ser Leu Asp Val Ser Ala Ala Phe Tyr His Leu Pro Leu
            580                 585                 590

His Pro Ala Ala Met Pro His Leu Leu Val Gly Ser Ser Gly Leu Ser
            595                 600                 605

Arg Tyr Val Ala Arg Leu Ser Ser Asn Ser Arg Ile Ile Asn His Gln
610                 615                 620

His Gly Thr Met Gln Asn Leu His Asp Ser Cys Ser Arg Asn Leu Tyr
625                 630                 635                 640

Val Ser Leu Leu Leu Leu Tyr Lys Thr Phe Gly Arg Lys Leu His Leu
                645                 650                 655

Tyr Ser His Pro Ile Ile Leu Gly Phe Arg Lys Ile Pro Met Gly Val
            660                 665                 670

Gly Leu Ser Pro Phe Leu Leu Ala Gln Phe Thr Ser Ala Ile Cys Ser
            675                 680                 685

Val Val Arg Arg Ala Phe Pro His Cys Leu Ala Phe Ser Tyr Met Asn
690                 695                 700

Asn Val Val Leu Gly Ala Lys Ser Val Gln His Leu Glu Ser Leu Phe
705                 710                 715                 720

Thr Ala Val Thr Asn Phe Leu Leu Ser Leu Gly Ile His Leu Asn Pro
                725                 730                 735

Asn Lys Thr Lys Arg Trp Gly Tyr Ser Leu Asn Phe Met Gly Tyr Val
                740                 745                 750

Ile Gly Ser Trp Gly Thr Leu Pro Gln Glu His Ile Val Gln Lys Ile
            755                 760                 765

Lys Glu Cys Phe Arg Lys Leu Pro Val Asn Arg Pro Ile Asp Trp Lys
770                 775                 780
```

```
Val Cys Gln Arg Ile Val Gly Leu Leu Gly Phe Ala Ala Pro Phe Thr
785                 790                 795                 800

Gln Cys Gly Tyr Pro Ala Leu Met Pro Leu Tyr Ala Cys Ile Gln Ser
            805                 810                 815

Lys Gln Ala Phe Thr Phe Ser Pro Thr Tyr Lys Ala Phe Leu Cys Lys
            820                 825                 830

Gln Tyr Leu Asn Leu Tyr Pro Val Ala Arg Gln Arg Pro Gly Leu Cys
            835                 840                 845

Gln Val Phe Ala Asn Ala Thr Pro Thr Gly Trp Gly Leu Ala Ile Gly
            850                 855                 860

His Gln Arg Met Arg Gly Thr Phe Val Ala Pro Leu Pro Ile His Thr
865                 870                 875                 880

Ala Gln Leu Leu Ala Ala Cys Phe Ala Arg Ser Arg Ser Gly Ala Lys
                885                 890                 895

Leu Ile Gly Thr Asp Asn Ser Val Val Leu Ser Arg Lys Tyr Thr Ser
                900                 905                 910

Phe Pro Trp Leu Leu Gly Cys Ala Ala Asn Trp Ile Leu Arg Gly Thr
            915                 920                 925

Ser Phe Val Tyr Val Pro Ser Ala Leu Asn Pro Ala Asp Asp Pro Ser
930                 935                 940

Arg Gly Arg Leu Gly Leu Tyr Arg Pro Leu Leu Arg Leu Pro Phe Arg
945                 950                 955                 960

Pro Thr Thr Gly Arg Thr Ser Leu Tyr Ala Asp Ser Pro Ser Val Pro
                965                 970                 975

Ser His Leu Pro Asp Arg Val His Phe Ala Ser Pro Leu His Val Ala
            980                 985                 990

Trp Arg Pro Pro
        995

<210> SEQ ID NO 13
<211> LENGTH: 1023
<212> TYPE: PRT
<213> ORGANISM: Artificial Sequence
<220> FEATURE:
<223> OTHER INFORMATION: Core-Pol fusion

<400> SEQUENCE: 13

Met Glu Phe Gly Leu Ser Trp Val Phe Leu Val Ala Ile Leu Lys Gly
1               5                   10                  15

Val Gln Cys Glu Val Gln Leu Leu Glu Ser Gly Met Asp Ile Asp Pro
            20                  25                  30

Tyr Lys Glu Phe Gly Ala Ser Val Glu Leu Leu Ser Phe Leu Pro Ser
        35                  40                  45

Asp Phe Phe Pro Ser Ile Arg Asp Leu Leu Asp Thr Ala Ser Ala Leu
    50                  55                  60

Tyr Arg Glu Ala Leu Glu Ser Pro Glu His Cys Ser Pro His His Thr
65                  70                  75                  80

Ala Leu Arg Gln Ala Ile Leu Cys Trp Gly Glu Leu Met Asn Leu Ala
                85                  90                  95

Thr Trp Val Gly Ser Asn Leu Glu Asp Pro Ala Ser Arg Glu Leu Val
            100                 105                 110

Val Ser Tyr Val Asn Val Asn Met Gly Leu Lys Ile Arg Gln Leu Leu
        115                 120                 125

Trp Phe His Ile Ser Cys Leu Thr Phe Gly Arg Glu Thr Val Leu Glu
    130                 135                 140
```

-continued

Tyr Leu Val Ser Phe Gly Val Trp Ile Arg Thr Pro Ala Tyr Arg
145                 150                 155                 160

Pro Pro Asn Ala Pro Ile Leu Ser Thr Leu Pro Glu Thr Thr Val Val
            165                 170                 175

Ala Gly Ala Gly Met Pro Leu Ser Tyr Gln His Phe Arg Lys Leu Leu
            180                 185                 190

Leu Leu Asp Asp Glu Ala Gly Pro Leu Glu Glu Leu Pro Arg Leu
        195                 200                 205

Ala Asp Glu Gly Leu Asn Arg Arg Val Ala Glu Asp Leu Asn Leu Gly
210                 215                 220

Asn Leu Asn Val Ser Ile Pro Trp Thr His Lys Val Gly Asn Phe Thr
225                 230                 235                 240

Gly Leu Tyr Ser Ser Thr Val Pro Val Phe Asn Pro Glu Trp Gln Thr
                245                 250                 255

Pro Ser Phe Pro Asn Ile His Leu Gln Glu Asp Ile Ile Asn Arg Cys
            260                 265                 270

Glu Gln Phe Val Gly Pro Leu Thr Val Asn Glu Lys Arg Arg Leu Lys
        275                 280                 285

Leu Ile Met Pro Ala Arg Phe Tyr Pro Asn Val Thr Lys Tyr Leu Pro
290                 295                 300

Leu Asp Lys Gly Ile Lys Pro Tyr Tyr Pro Glu His Leu Val Asn His
305                 310                 315                 320

Tyr Phe Gln Thr Arg His Tyr Leu His Thr Leu Trp Lys Ala Gly Ile
                325                 330                 335

Leu Tyr Lys Arg Glu Thr Thr Arg Ser Ala Ser Phe Cys Gly Ser Pro
            340                 345                 350

Tyr Ser Trp Glu Gln Glu Leu Gln His Gly Arg Leu Val Phe Gln Thr
        355                 360                 365

Ser Thr Arg His Gly Asp Glu Ser Phe Cys Gln Gln Ser Ser Gly Ile
    370                 375                 380

Leu Ser Arg Ser Pro Val Gly Pro Cys Leu Gln Ser Gln Leu Arg Lys
385                 390                 395                 400

Ser Arg Leu Gly Leu Gln Pro Gln Gln Gly His Leu Ala Arg Arg Gln
                405                 410                 415

Gln Gly Arg Ser Gly Ser Ile Arg Ala Arg Val His Pro Thr Thr Arg
            420                 425                 430

Arg Pro Phe Gly Val Glu Pro Ser Gly Ser Gly His Thr Thr Asn Thr
        435                 440                 445

Ala Ser Ser Ser Ser Ser Cys Leu His Gln Ser Ala Val Arg Lys Ala
    450                 455                 460

Ala Tyr Ser His Leu Ser Thr Ser Lys Arg His Ser Ser Ser Gly His
465                 470                 475                 480

Ala Val Glu Leu His Asn Ile Pro Pro Asn Ser Ala Arg Ser Gln Ser
                485                 490                 495

Glu Gly Pro Val Phe Ser Cys Trp Trp Leu Gln Phe Arg Asn Ser Lys
            500                 505                 510

Pro Cys Ser Asp Tyr Cys Leu Ser His Ile Val Asn Leu Leu Glu Asp
        515                 520                 525

Trp Gly Pro Cys Thr Glu His Gly Glu His His Ile Arg Ile Pro Arg
    530                 535                 540

Thr Pro Ala Arg Val Thr Gly Gly Val Phe Leu Val Asp Lys Asn Pro
545                 550                 555                 560

```
His Asn Thr Thr Glu Ser Arg Leu Val Val Asp Phe Ser Gln Phe Ser
                565                 570                 575

Arg Gly Asn Thr Arg Val Ser Trp Pro Lys Phe Ala Val Pro Asn Leu
            580                 585                 590

Gln Ser Leu Thr Asn Leu Leu Ser Ser Asn Leu Ser Trp Leu Ser Leu
        595                 600                 605

Asp Val Ser Ala Ala Phe Tyr His Leu Pro Leu His Pro Ala Ala Met
610                 615                 620

Pro His Leu Leu Val Gly Ser Ser Gly Leu Ser Arg Tyr Val Ala Arg
625                 630                 635                 640

Leu Ser Ser Asn Ser Arg Ile Ile Asn His Gln His Gly Thr Met Gln
                645                 650                 655

Asn Leu His Asp Ser Cys Ser Arg Asn Leu Tyr Val Ser Leu Leu Leu
            660                 665                 670

Leu Tyr Lys Thr Phe Gly Arg Lys Leu His Leu Tyr Ser His Pro Ile
        675                 680                 685

Ile Leu Gly Phe Arg Lys Ile Pro Met Gly Val Gly Leu Ser Pro Phe
    690                 695                 700

Leu Leu Ala Gln Phe Thr Ser Ala Ile Cys Ser Val Val Arg Arg Ala
705                 710                 715                 720

Phe Pro His Cys Leu Ala Phe Ser Tyr Met Asn Asn Val Val Leu Gly
                725                 730                 735

Ala Lys Ser Val Gln His Leu Glu Ser Leu Phe Thr Ala Val Thr Asn
            740                 745                 750

Phe Leu Leu Ser Leu Gly Ile His Leu Asn Pro Asn Lys Thr Lys Arg
        755                 760                 765

Trp Gly Tyr Ser Leu Asn Phe Met Gly Tyr Val Ile Gly Ser Trp Gly
    770                 775                 780

Thr Leu Pro Gln Glu His Ile Val Gln Lys Ile Lys Glu Cys Phe Arg
785                 790                 795                 800

Lys Leu Pro Val Asn Arg Pro Ile Asp Trp Lys Val Cys Gln Arg Ile
                805                 810                 815

Val Gly Leu Leu Gly Phe Ala Ala Pro Phe Thr Gln Cys Gly Tyr Pro
            820                 825                 830

Ala Leu Met Pro Leu Tyr Ala Cys Ile Gln Ser Lys Gln Ala Phe Thr
        835                 840                 845

Phe Ser Pro Thr Tyr Lys Ala Phe Leu Cys Lys Gln Tyr Leu Asn Leu
    850                 855                 860

Tyr Pro Val Ala Arg Gln Arg Pro Gly Leu Cys Gln Val Phe Ala Asn
865                 870                 875                 880

Ala Thr Pro Thr Gly Trp Gly Leu Ala Ile Gly His Gln Arg Met Arg
                885                 890                 895

Gly Thr Phe Val Ala Pro Leu Pro Ile His Thr Ala Gln Leu Leu Ala
            900                 905                 910

Ala Cys Phe Ala Arg Ser Arg Ser Gly Ala Lys Leu Ile Gly Thr Asp
        915                 920                 925

Asn Ser Val Val Leu Ser Arg Lys Tyr Thr Ser Phe Pro Trp Leu Leu
    930                 935                 940

Gly Cys Ala Ala Asn Trp Ile Leu Arg Gly Thr Ser Phe Val Tyr Val
945                 950                 955                 960

Pro Ser Ala Leu Asn Pro Ala Asp Asp Pro Ser Arg Gly Arg Leu Gly
                965                 970                 975
```

Leu Tyr Arg Pro Leu Leu Arg Leu Pro Phe Arg Pro Thr Thr Gly Arg
            980                 985                 990

Thr Ser Leu Tyr Ala Asp Ser Pro  Ser Val Pro Ser His  Leu Pro Asp
        995                 1000                 1005

Arg Val  His Phe Ala Ser Pro  Leu His Val Ala Trp  Arg Pro Pro
    1010                 1015                 1020

<210> SEQ ID NO 14
<211> LENGTH: 12
<212> TYPE: DNA
<213> ORGANISM: Artificial Sequence
<220> FEATURE:
<223> OTHER INFORMATION: Linker coding sequence

<400> SEQUENCE: 14
gccggagctg gc                                                           12

<210> SEQ ID NO 15
<211> LENGTH: 248
<212> TYPE: DNA
<213> ORGANISM: Artificial Sequence
<220> FEATURE:
<223> OTHER INFORMATION: ApoA1 gene fragment

<400> SEQUENCE: 15
ttggccgtgc tcttcctgac gggtaggtgt ccoctaacct agggagccaa ccatcggggg       60
gccttctccc taaatccccg tgcccaccc tcctgggcag aggcagcagg tttctcactg       120 gcccctctc ccaccctcc aagcttggcc tttcggctca gatctcagcc cacagctggc       180
ctgatctggg tctcccctcc caccctcagg gagccaggct cggcatttcg tcgacaagct      240
tagccacc                                                                248

<210> SEQ ID NO 16
<211> LENGTH: 130
<212> TYPE: DNA
<213> ORGANISM: Artificial Sequence
<220> FEATURE:
<223> OTHER INFORMATION: SV40 polyadenylation signal

<400> SEQUENCE: 16
aacttgttta ttgcagctta taatggttac aaataaagca atagcatcac aaatttcaca      60
aataaagcat ttttttcact gcattctagt tgtggtttgt ccaaactcat caatgtatct    120
tatcatgtct                                                              130

<210> SEQ ID NO 17
<211> LENGTH: 447
<212> TYPE: DNA
<213> ORGANISM: Artificial Sequence
<220> FEATURE:
<223> OTHER INFORMATION: HBV core

<400> SEQUENCE: 17
atggacatcg acccttacaa ggagttcggc gccagcgtgg aactgctgtc ttttctgccc      60
agtgatttct tccttccat tcgagacctg ctggataccg cctctgctct gtatcggaa      120 gccctggaga gcccagaaca ctgctcccca ccataccg ctctgcgaca ggcaatcctg      180
tgctgggggg agctgatgaa cctggccaca tgggtgggat ccaatctgga ggaccccgct    240
tcacgggaac tggtggtcag ctacgtgaac gtcaatatgg gcctgaaaat ccgccagctg    300
ctgtggttcc atattagctg cctgactttt ggacgagaga ccgtgctgga atacctggtg    360

```
tccttcggcg tctggatccg cactccccct gcttatcgac cacccaacgc accaattctg    420
tccaccctgc ccgagaccac agtggtc                                        447
```

<210> SEQ ID NO 18
<211> LENGTH: 447
<212> TYPE: DNA
<213> ORGANISM: Artificial Sequence
<220> FEATURE:
<223> OTHER INFORMATION: HBV core

<400> SEQUENCE: 18

```
atggacatcg acccttacaa ggagttcggc gccagcgtgg aactgctgtc ttttctgccc     60
agtgatttct ttccttccat tcgagacctg ctggataccg cctctgctct gtatcgggaa    120
gccctggaga gcccagaaca ctgctcccca caccataccg ctctgcgaca ggcaatcctg    180
tgctgggggg agctgatgaa cctggccaca tgggtgggat cgaatctgga ggaccccgct    240
tcacgggaac tggtggtcag ctacgtgaac gtcaatatgg gcctgaaaat ccgccagctg    300
ctgtggttcc atattagctg cctgactttt ggacgagaga ccgtgctgga atacctggtg    360
tccttcggcg tctggattcg cactccccct gcttatcgac cacccaacgc accaattctg    420
tccaccctgc ccgagaccac agtggtc                                        447
```

<210> SEQ ID NO 19
<211> LENGTH: 2529
<212> TYPE: DNA
<213> ORGANISM: Artificial Sequence
<220> FEATURE:
<223> OTHER INFORMATION: HBV pol

<400> SEQUENCE: 19

```
atgcccctgt cttaccagca ctttagaaag ctgctgctgc tggacgatga agccgggcct     60
ctggaggaag agctgccaag gctggcagac gaggggctga accggagagt ggccgaagat    120
ctgaatctgg gaaacctgaa cgtgagcatc ccttggactc ataaagtcgg caacttcacc    180
gggctgtaca gctccacagt gcctgtcttc aatccagagt ggcagacacc atcctttccc    240
aacattcacc tgcaggagga catcattaat agatgcgaac agttcgtggg acctctgaca    300
gtcaacgaaa agaggcgcct gaaactgatc atgcctgcca ggttttaccc aaatgtgact    360
aagtatctgc cactggataa gggcatcaag ccttactatc agagcacct ggtgaaccat    420 tacttccaga ctagacacta tctgcatacc ctgtggaagg ccggaatcct gtacaaacga    480
gaaactaccc ggagtgcttc attttgtggc tccccatatt cttgggaaca ggagctgcag    540
catggcaggc tggtgttcca gaccagcaca cgccacgggg atgagtcctt ttgccagcag    600
tctagtggca tcctgagcag atccccgtg gggccttgtc tgcagtctca gctgcggaag    660
agtagactgg gactgcagcc acagcaggga cacctggcac gacggcagca gggaaggtct    720
ggcagtatcc gggctagagt gcatcccaca actagaaggc cttcggcgt cgagccatca    780 ggaagcggcc acaccacaaa caccgcatca agctcctcta gttgcctgca tcagtcagcc    840
gtgagaaagg ccgcttacag ccacctgtcc acatctaaaa ggcactcaag ctccgggcat    900
gctgtggagc tgcacaacat ccctccaaat tctgcacgca gtcagtcaga aggacccgtg    960
ttcagctgct ggtggctgca gtttcggaac tcaaagcctt gcagcgacta ttgtctgagc   1020
catattgtga atctgctgga ggattgggc ccttgtaccg agcacgggga acaccatatc   1080
aggattccac gaacaccagc acgagtgact ggagggggtgt tcctggtgga caagaacccc   1140
cacaatacta ccgagagccg gctggtggtc gatttcagtc agttttcaag aggcaacaca   1200
```

| | |
|---|---:|
| agggtgtcat ggcccaaatt cgccgtccct aatctgcaga gtctgactaa cctgctgtct | 1260 |
| agtaatctga gctggctgtc cctggacgtg tccgcagcct tttaccacct gcctctgcat | 1320 |
| ccagctgcaa tgccccatct gctggtgggg tcaagcggac tgagtcgcta cgtcgcccga | 1380 |
| ctgtcctcta actcacgcat cattaatcac cagcatggca ccatgcagaa cctgcacgat | 1440 |
| agctgttccc ggaatctgta cgtgtctctg ctgctgctgt ataagacatt cggcagaaaa | 1500 |
| ctgcacctgt acagccatcc tatcattctg gggtttagga agatcccaat gggagtggga | 1560 |
| ctgagcccct tcctgctggc acagtttacc tccgccattt gctctgtggt ccgccgagcc | 1620 |
| ttcccacact gtctggcttt ttcctatatg aacaatgtgg tcctgggcgc caaatccgtg | 1680 |
| cagcatctgg agtctctgtt cacagctgtc actaactttc tgctgagcct ggggatccac | 1740 |
| ctgaacccaa ataagactaa acgctggggg tacagcctga atttcatggg atatgtgatt | 1800 |
| ggatcctggg ggaccctgcc acaggagcac atcgtgcaga gatcaagga atgctttcgg | 1860 |
| aagctgcccg tcaacagacc tatcgactgg aaagtgtgcc agcggattgt cggactgctg | 1920 |
| ggcttcgccg ctccctttac ccagtgcggg tacccagcac tgatgcccct gtatgcctgt | 1980 |
| atccagtcta agcaggcttt cacctttagt cctacataca aggcattcct gtgcaaacag | 2040 |
| tacctgaacc tgtatccagt ggcaaggcag cgacctggac tgtgccaggt ctttgcaaat | 2100 |
| gccactccta ccggctgggg gctggctatc ggacatcagc gaatgcgggg cacattcgtg | 2160 |
| gcccccctgc ctattcacac tgctcagctg ctggcagcct gctttgctag atctaggagt | 2220 |
| ggagcaaagc tgatcggcac cgacaatagt gtggtcctgt caagaaaata cacatccttc | 2280 |
| ccatggctgc tgggatgtgc tgcaaactgg attctgaggg gcaccagctt cgtgtacgtc | 2340 |
| ccctcagccc tgaatcctgc tgacgatcca tcccgcgggc gactgggact gtaccgacct | 2400 |
| ctgctgagac tgcccttcag gcctacaact ggccggacat ctctgtatgc cgattccaca | 2460 |
| agcgtgccct cacacctgcc tgacagagtc cactttgctt caccccctgca cgtcgcttgg | 2520 |
| cggcctcca | 2529 |

<210> SEQ ID NO 20
<211> LENGTH: 2529
<212> TYPE: DNA
<213> ORGANISM: Artificial Sequence
<220> FEATURE:
<223> OTHER INFORMATION: HBV pol

<400> SEQUENCE: 20

| | |
|---|---:|
| atgcccctgt cttaccagca ctttagaaag cttctgctgc tggacgatga agccgggcct | 60 |
| ctggaggaag agctgccaag gctggcagac gaggggctga accggagagt ggccgaagat | 120 |
| ctgaatctgg gaaacctgaa cgtgagcatc ccttggactc ataaagtcgg caacttcacc | 180 |
| gggctgtaca gctccacagt gcctgtcttc aatccagagt ggcagacacc atcctttccc | 240 |
| aacattcacc tgcaggagga catcattaat agatgcgaac agttcgtggg acctctgaca | 300 |
| gtcaacgaaa agaggcgcct gaaactgatc atgcctgcca ggttttaccc aaatgtgact | 360 |
| aagtatctgc cactggataa gggcatcaag ccttactatc cagagcacct ggtgaaccat | 420 |
| tacttccaga ctagacacta tctgcatacc ctgtggaagg ccggaatcct gtacaaacga | 480 |
| gaaactaccc ggagtgcttc attttgtggc tccccatatt cttgggaaca ggagctgcag | 540 |
| catggcaggc tggtgttcca gaccagcaca cgccacgggg atgagtcctt ttgccagcag | 600 |
| tctagtggca tcctgagcag atcccccgtg gggccttgtc tgcagtctca gctgcggaag | 660 |
| agtagactgg gactgcagcc acagcaggga cacctggcac gacggcagca gggaaggtct | 720 |

```
ggcagtatcc gggctagagt gcatcccaca actagaaggc ctttcggcgt cgagccatca    780
ggaagcggcc acaccacaaa caccgcatca agctcctcta gttgcctgca tcagtcagcc    840
gtgagaaagg ccgcttacag ccacctgtcc acatctaaaa ggcactcaag ctccgggcat    900
gctgtggagc tgcacaacat ccctccaaat tctgcacgca gtcagtcaga aggacccgtg    960
ttcagctgct ggtggctgca gtttcggaac tcaaagcctt gcagcgacta ttgtctgagc   1020
catattgtga atctgctgga ggattggggc ccttgtaccg agcacgggga acaccatatc   1080
aggattccac gaacaccagc acgagtgact ggaggggtgt tcctggtgga caagaacccc   1140
cacaatacta ccgagagccg gctggtggtc gatttcagtc agttttcaag aggcaacaca   1200
agggtgtcat ggcccaaatt cgccgtccct aatctgcaga gtctgactaa cctgctgtct   1260
agtaatctga gctggctgtc cctggacgtg tccgcagcct tttaccacct gcctctgcat   1320
ccagctgcaa tgccccatct gctggtgggg tcaagcggac tgagtcgcta cgtcgcccga   1380
ctgtcctcta actcacgcat cattaatcac cagcatggca ccatgcagaa cctgcacgat   1440
agctgttccc ggaatctgta cgtgtctctg ctgctgctgt ataagacatt cggcagaaaa   1500
ctgcacctgt acagccatcc tatcattctg ggtttagga agatcccaat gggagtggga   1560
ctgagcccct tcctgctggc acagtttacc tccgccattt gctctgtggt ccgccgagcc   1620
ttcccacact gtctggcttt ttcctatatg aacaatgtgg tcctgggcgc caaatccgtg   1680
cagcatctgg agtctctgtt cacagctgtc actaactttc tgctgagcct ggggatccac   1740
ctgaacccaa ataagactaa cgctgggggg tacagcctga atttcatggg atatgtgatt   1800
ggatcctggg ggaccctgcc acaggagcac atcgtgcaga agatcaagga atgctttcgg   1860
aagctgcccg tcaacagacc tatcgactgg aaagtgtgcc agcggattgt cggactgctg   1920
ggcttcgccg ctcccttttac ccagtgcggg tacccagcac tgatgcccct gtatgcctgt   1980
atccagtcta agcaggcttt cacctttagt cctacataca aggcattcct gtgcaaacag   2040
tacctgaacc tgtatccagt ggcaaggcag cgacctggac tgtgccaggt ctttgcaaat   2100
gccactccta ccggctgggg gctggctatc ggacatcagc gaatgcgggg cacattcgtg   2160
gccccctgc ctattcacac tgctcagctg ctggcagcct gctttgctag atctaggagt   2220
ggagcaaagc tgatcggcac cgacaatagt gtggtcctgt caagaaaata cacatccttc   2280
ccatggctgc tgggatgtgc tgcaaactgg attctgaggg gcaccagctt cgtgtacgtc   2340
ccctcagccc tgaatcctgc tgacgatcca tcccgcgggc gactgggact gtaccgacct   2400
ctgctgagac tgcccttcag gcctacaact ggcggacat ctctgtatgc cgattccacca   2460
agcgtgccct cacacctgcc tgacagagtc cactttgctt caccccttgca cgtcgcttgg   2520
cggcctcca                                                          2529
```

<210> SEQ ID NO 21
<211> LENGTH: 671
<212> TYPE: DNA
<213> ORGANISM: Artificial Sequence
<220> FEATURE:
<223> OTHER INFORMATION: pUC Ori

<400> SEQUENCE: 21

```
cccgtagaaa agatcaaagg atcttcttga atcctttttt ttctgcgcgt aatctgctgc     60
ttgcaaacaa aaaaaccgct accagcggtg gtttgtttgc cggatcaaga gctaccaact    120
ctttttccga aggtaactgg cttcagcaga gcgcagatac caaatactgt tcttctagtg    180
tagccgtagt taggccacca cttcaagaac tctgtagcac cgcctacata cctcgctctg    240
```

```
ctaatcctgt taccagtggc tgctgccagt ggcgataagt cgtgtcttac cgggttggac    300
tcaagacgat agttaccgga taaggcgcag cggtcgggct gaacgggggg ttcgtgcaca    360
cagcccagct tggagcgaac gacctacacc gaactgagat acctacagcg tgagctatga    420
gaaagcgcca cgcttcccga agggagaaag gcggacaggt atccggtaag cggcagggtc    480
ggaacaggag agcgcacgag ggagcttcca ggggaaacg cctggtatct ttatagtcct     540
gtcgggtttc gccacctctg acttgagcgt cgattttgt gatgctcgtc agggggcgg      600 agcctatgga aaaacgccag caacgcggcc ttttacggt tcctggcctt tgctggcct     660 tttgctcaca t                                                         671

<210> SEQ ID NO 22
<211> LENGTH: 795
<212> TYPE: DNA
<213> ORGANISM: Artificial Sequence
<220> FEATURE:
<223> OTHER INFORMATION: Kan resistance

<400> SEQUENCE: 22
atgattgagc aagatggtct tcacgctggc tcgccagctg cgtgggtgga acgcctgttt     60
ggttatgatt gggcgcagca gactattgga tgttccgacg cggctgtatt tcggctgtct   120
gctcagggtc gccccgtgct gtttgtgaag acggatttgt ctggcgcatt aaatgagtta   180
caggacgagg cggctcgtct gagttggttg gccaccaccg gcgtgccctg cgccgcagtg   240
ctggatgtcg tgacagaagc aggccgcgat tggctccttc tcggcgaagt gccgggccag   300
gacctgctca gcagccactt ggcaccggca gaaaaagttt ctatcatggc cgacgccatg   360
cgtcgtcttc acactctcga tccggccacg tgcccctttg accaccaggc caagcatcgt   420
attgaacgtg cgcgtactcg gatggaagca ggtttagtag accaggacga tttggatgag   480
gaacatcaag gcctggcccc ggctgaactg tttgcgcgct aaaagcgtc gatgccagat    540 ggcgaagatt tggtagtcac ccatggagat gcgtgtttgc caaacatcat ggttgaaaat   600
ggccgcttct caggctttat tgactgtggg cgcctgggtg ttgccgaccg ctatcaagat   660
attgcgctcg caactcgtga catcgctgaa gagctgggcg gagaatgggc tgaccgtttc   720
ctggtactgt atggcattgc agcgcccgat tcccaacgca tcgcattta tcgtctgctg   780 gatgagtttt tctaa                                                    795

<210> SEQ ID NO 23
<211> LENGTH: 264
<212> TYPE: PRT
<213> ORGANISM: Artificial Sequence
<220> FEATURE:
<223> OTHER INFORMATION: Kan resistance

<400> SEQUENCE: 23

Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80
```

```
Leu Asp Val Val Thr Glu Ala Gly Arg Asp Trp Leu Leu Leu Gly Glu
            85                  90                  95

Val Pro Gly Gln Asp Leu Leu Ser Ser His Leu Ala Pro Ala Glu Lys
        100                 105                 110

Val Ser Ile Met Ala Asp Ala Met Arg Arg Leu His Thr Leu Asp Pro
    115                 120                 125

Ala Thr Cys Pro Phe Asp His Gln Ala Lys His Arg Ile Glu Arg Ala
130                 135                 140

Arg Thr Arg Met Glu Ala Gly Leu Val Asp Gln Asp Leu Asp Glu
145                 150                 155                 160

Glu His Gln Gly Leu Ala Pro Ala Glu Leu Phe Ala Arg Leu Lys Ala
                165                 170                 175

Ser Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260
```

```
<210> SEQ ID NO 24
<211> LENGTH: 99
<212> TYPE: DNA
<213> ORGANISM: Artificial Sequence
<220> FEATURE:
<223> OTHER INFORMATION: bla promoter

<400> SEQUENCE: 24
acccctattt gtttattttt ctaaatacat tcaaatatgt atccgctcat gagacaataa    60
ccctgataaa tgcttcaata atattgaaaa aggaagagt                           99

<210> SEQ ID NO 25
<211> LENGTH: 124
<212> TYPE: DNA
<213> ORGANISM: Artificial Sequence
<220> FEATURE:
<223> OTHER INFORMATION: PrMVA13.5 Long Promoter

<400> SEQUENCE: 25
taaaaataga aactataatc atataatagt gtaggttggt agtattgctc ttgtgactag    60
agactttagt taaggtactg taaaaataga aactataatc atataatagt gtaggttggt   120
agta                                                                124

<210> SEQ ID NO 26
<211> LENGTH: 227
<212> TYPE: DNA
<213> ORGANISM: Artificial Sequence
<220> FEATURE:
<223> OTHER INFORMATION: PrHyb Promoter

<400> SEQUENCE: 26
gttttgaaaa ttttttttata ataaatatcc ggtaaaaatt gaaaaactat tctaatttat    60
tgcacggtcc ggtaaaaatt gaaaaactat tctaatttat tgcacggtcc ggtaaaaatt   120
```

-continued

```
gaaaaactat tctaatttat tgcacggtcc ggtaaaaatt gaaaaactat tctaatttat      180
tgcacggtcc ggtaaaaatt gaaaaactat tctaatttat tgcacgg                    227

<210> SEQ ID NO 27
<211> LENGTH: 81
<212> TYPE: DNA
<213> ORGANISM: Artificial Sequence
<220> FEATURE:
<223> OTHER INFORMATION: Immunoglobulin Secretion Tag

<400> SEQUENCE: 27
atggaattcg gcctgagctg ggtgttcctg gtggccatcc tgaagggagt gcagtgcgag       60
gtgcagctgc tggaaagcgg t                                                 81

<210> SEQ ID NO 28
<211> LENGTH: 7
<212> TYPE: DNA
<213> ORGANISM: Artificial Sequence
<220> FEATURE:
<223> OTHER INFORMATION: Transcription Termination Sequence
<220> FEATURE:
<221> NAME/KEY: n
<222> LOCATION: (6)..(6)
<223> OTHER INFORMATION: n, wherein n can be any nucleotide

<400> SEQUENCE: 28 tttttnt                                                                  7
```